(12) United States Patent
Ogino et al.

(10) Patent No.: US 7,994,331 B2
(45) Date of Patent: Aug. 9, 2011

(54) HETEROCYCLE-SUBSTITUTED BENZIMIDAZOLE DERIVATIVE

(75) Inventors: Yoshio Ogino, Tsukuba (JP); Katsumasa Nonoshita, Tsukuba (JP); Teruyuki Nishimura, Ushiku (JP); Jun-ichi Eiki, Tsuchiura (JP)

(73) Assignee: MSD K.K. (JP)

( * ) Notice: Subject to any disclaimer, the term of this patent is extended or adjusted under 35 U.S.C. 154(b) by 701 days.

(21) Appl. No.: 11/988,592

(22) PCT Filed: Jul. 12, 2006

(86) PCT No.: PCT/JP2006/314307
§ 371 (c)(1), (2), (4) Date: Jan. 10, 2008

(87) PCT Pub. No.: WO2007/007910
PCT Pub. Date: Jan. 18, 2007

(65) Prior Publication Data
US 2010/0087360 A1  Apr. 8, 2010

(30) Foreign Application Priority Data
Jul. 13, 2005  (JP) .................. 2005-204438

(51) Int. Cl.
*C07D 413/14* (2006.01)
*A61K 31/44* (2006.01)
(52) U.S. Cl. .................... 546/271.4; 514/338
(58) Field of Classification Search ............... None
See application file for complete search history.

(56) References Cited

U.S. PATENT DOCUMENTS

| | | |
|---|---|---|
| 6,187,805 B1 | 2/2001 | Pineiro et al. |
| 6,316,468 B1 | 11/2001 | Maxey et al. |
| 6,433,188 B1 | 8/2002 | Corbett et al. |
| 6,441,184 B1 | 8/2002 | Corbett et al. |
| 6,448,399 B1 | 9/2002 | Corbett et al. |
| 6,518,273 B1 | 2/2003 | Chapman et al. |
| 6,545,155 B2 | 4/2003 | Corbett et al. |
| 6,723,725 B1 | 4/2004 | Bottcher et al. |
| 7,253,286 B2 | 8/2007 | Funahashi et al. |
| 7,301,036 B2 | 11/2007 | Parmee et al. |
| 2002/0103199 A1 | 8/2002 | Corbett et al. |
| 2002/0103241 A1 | 8/2002 | Corbett et al. |
| 2002/0107396 A1 | 8/2002 | Corbett et al. |
| 2002/0111372 A1 | 8/2002 | Corbett et al. |
| 2004/0053908 A1 | 3/2004 | Funahashi et al. |
| 2005/0153980 A1 | 7/2005 | Schadt et al. |
| 2006/0063811 A1 | 3/2006 | Hoelzemann et al. |
| 2006/0160824 A1 | 7/2006 | Heinrich et al. |
| 2006/0160832 A1 | 7/2006 | Funahashi et al. |
| 2006/0247259 A1 | 11/2006 | Funahashi et al. |
| 2007/0093544 A1 | 4/2007 | Parmee et al. |
| 2007/0099933 A1 | 5/2007 | Heinrich et al. |
| 2007/0105930 A1 | 5/2007 | Parmee et al. |
| 2008/0070928 A1 | 3/2008 | Nonoshita et al. |
| 2008/0125429 A1 * | 5/2008 | Hashimoto et al. ......... 514/234.5 |

FOREIGN PATENT DOCUMENTS

| | | |
|---|---|---|
| CA | 2586056 | 5/2006 |
| EP | 1 810 969 | 7/2007 |
| JP | 2004-67629 | 3/2004 |
| JP | 2004-517087 | 6/2004 |
| WO | WO 02/32872 | 4/2002 |
| WO | WO 02/39989 | 5/2002 |
| WO | WO 2003/087086 | 10/2003 |
| WO | WO 2004/014300 | 2/2004 |
| WO | WO 2004/026248 | 4/2004 |
| WO | WO 2004/100875 | 11/2004 |
| WO | WO 2004/113325 | 12/2004 |
| WO | WO 2004/113326 | 12/2004 |
| WO | WO 2005/054193 | 6/2005 |
| WO | WO 2005/063738 | 7/2005 |
| WO | WO 2005/065680 | 7/2005 |
| WO | WO 2006/014262 | 2/2006 |
| WO | WO 2006/049304 | 5/2006 |
| WO | WO 2006/074789 | 7/2006 |
| WO | WO 2007/019675 | 2/2007 |
| WO | WO 2007/021629 | 2/2007 |
| WO | WO 2007/061763 | 5/2007 |
| WO | WO 2007/121578 | 11/2007 |

* cited by examiner

*Primary Examiner* — Kamal Saeed
*Assistant Examiner* — Nyeemah A Grazier
(74) *Attorney, Agent, or Firm* — Heidi M. Struse; Richard C. Billups

(57) ABSTRACT

A compound represented by the formula (I) or a pharmaceutically acceptable salt thereof: (I) wherein $X_1$ to $X_4$ independently represent a carbon atom or the like; the ring A represents a 5- to 6-membered heteroaryl having 1 to 4 heteroatoms independently selected from the group consisting of a nitrogen atom, a sulfur atom and an oxygen atom; $X_5$ represents an oxygen atom or the like; X represents a carbon atom or the like; Het represents a 5- or 6-membered aliphatic heterocycle; $R^1$ represents an aryl or the like; $R^2$ represents a formyl group or the like; and $R^3$ represents a —$C_{1-6}$ alkyl or the like. The compound or salt has a glucokinase activation effect and is useful as a therapeutic agent for diabetes.

9 Claims, No Drawings

HETEROCYCLE-SUBSTITUTED BENZIMIDAZOLE DERIVATIVE

CROSS-REFERENCE TO RELATED APPLICATIONS

This application is a U.S. National Phase application under 35 U.S.C. §371 of PCT Application No. PCT/JP2006/314307, filed Jul. 12, 2006, which published as WO 2007/007910 A1 on Jan. 18, 2007, and claims priority under 35 U.S.C. §365(b) from Japanese patent application No. JP2005-204438, filed Jul. 13, 2005.

TECHNICAL FIELD

The present invention relates to a glucokinase activator comprising, as the active ingredient thereof, a hetero ring-substituted benzimidazole derivative. Further, it relates to a novel hetero ring-substituted benzimidazole derivative.

BACKGROUND ART

Glucokinase (GK) (ATP: D-hexose 6-phosphotransferase, EC 2.7.1.1) is one (hexokinase IV) of four mammal hexokinases. Hexokinase is a first-stage enzyme in glycolysis and catalyzes a reaction from glucose to glucose hexaphosphate. In its expression, glucokinase is limited essentially in liver and pancreas beta cells, and it controls the rate-limiting step of glucose metabolism in these cells thereby playing an important role in systemic saccharometabolism. Glucokinase in liver and that in pancreas beta cells differ from each other in point of the N-terminal 15-amino acid sequence owing to the difference in splicing therebetween, but they are the same in point of the enzymatic property. The enzymatic activity of the other three hexokinases (I, II, III) except glucokinase is saturated at a glucose concentration of at most 1 mM, but Km of glucokinase to glucose is 8 mM and is near to a physiological blood-glucose level. Thus, glucokinase-mediated intracellular glucose metabolism is accelerated in response to glucose level changes by postprandial glucose level increase (10-15 mM) from normal glucose (5 mM).

Since ten years ago, a hypothesis that glucokinase may act as a glucose sensor in pancreas beta cells and liver has been proposed (for example, see Garfinkel D. et al., Computer modeling identifies glucokinase as glucose sensor of pancreatic beta-cells; American Journal Physiology, Vol. 247 (3Pt2), 1984, pp. 527-536). A result of recent glucokinase gene-manipulated mice has clarified that glucokinase actually plays an important role in systemic glucose homeostasis. Mice in which the glucokinase gene was disrupted die soon after their birth (for example, see Grupe A. et al., Transgenic knockouts reveal a critical requirement for pancreatic beta cell glucokinase in maintaining glucose homeostasis; Cell, Vol. 83, 1995, pp. 69-78); but on the other hand, normal or diabetic mice in which glucokinase was excessively expressed have a lowered blood-glucose level (for example, see Ferre T. et al., Correction of diabetic alterations by glucokinase; Proceedings of the National Academy of Sciences of the U.S.A., Vol. 93, 1996, pp. 7225-7230). With the increase in glucose concentration therein, the reaction of pancreas beta cells and that of liver cells are both toward the reduction in a blood-glucose level, though differing from each other. Pancreas beta cells come to secrete more insulin, and liver takes up glucose to store it as glycogen therein and simultaneously reduces glucose release.

To that effect, the change in enzymatic activity of glucokinase plays an important role in mammal glucose homeostasis via liver and pancreas beta cells. In a juvenile diabetic case that is referred to as MODY2 (maturity-onset diabetes of the young), mutation of a glucokinase gene has been found, and the glucokinase activity reduction causes the blood-glucose level increase (for example, see Vionnet N. et al., Nonsense mutation in the glucokinase gene causes early-onset non-insulin-dependent diabetes mellitus; Nature Genetics, Vol. 356, 1992, pp. 721-722). On the other hand, a pedigree having mutation of increasing glucokinase activity has been found, and those of the family line show low blood-glucose level symptoms (for example, see Glaser B. et al., Familial hyperinsulinism caused by an activating glucokinase mutation; New England Journal Medicine, Vol. 338, 1998, pp. 226-230).

From these, glucokinase acts as a glucose sensor and plays an important role in glucose homeostasis also in humans. On the other hand, blood-glucose level control by utilizing a glucokinase sensor system may be possible in many type-II diabetes patients. A glucokinase-activating substance may be expected to have an insulin secretion promoting effect in pancreas beta cells and have a glucose take-up accelerating and glucose release inhibiting activity in liver, and therefore it may be useful as a remedy for type-II diabetes patients.

Recently, it has become clarified that pancreas beta cell-type glucokinase is limitedly expressed locally in rat brains, especially in ventromedial hypothalamus (VMH) thereof. About 20% neurocytes in VMH are referred to as glucose-responsive neutrons, and heretofore it has been considered they may play an important role in body weight control. When glucose is administered to a rat brain, then it reduces the amount of ingestion; but when glucose metabolism is retarded through intracerebral administration of glucosamine, a glucose analogue, then it causes hyperphagia. From an electrophysiological experiment, it is admitted that glucose-responsive neurons are activated in accordance with a physiological glucose concentration change (5 to 20 mM), but when glucose metabolisms is inhibited by glucosamine or the like, then their activity is retarded. In the glucose concentration-sensitive system in VHM, a glucokinase-mediated mechanism is anticipated like the insulin secretion in pancreas beta cells. Accordingly, there may be a possibility that a substance for glucokinase activation in VHM, in addition to liver and pancreas beta cells, may be effective not only for blood-glucose level correction but also for solution of obesity that is problematic in many type-II diabetes patients.

From the above description, a compound having a glucokinase activation effect is useful for remedies and/or preventives for diabetes, or for remedies and/or preventives for chronic complications of diabetes such as retinopathy, nephropathy, neurosis, ischemic cardiopathy, arteriosclerosis, and further for remedies and/or preventives for obesity.

As a compound that is structurally similar to the benzimidazole derivative (I) of the invention, for example, disclosed is a compound represented by the following formula (e.g., see WO2002/032872):

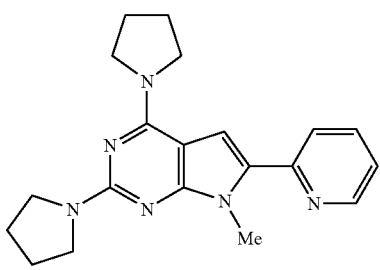

The compound of the above formula is common to the compound of the present invention in that they have one pyrrole group and have pyridine, but the basic skeleton of the above compound is a pyrrolo[2,3-d]pyrimidine skeleton and differs from the basic skeleton in the present invention. Further, the diseases to which the above formula is directed are subarachnoid hemorrhage and ischemic attack after it, and differ from those to which the compound of the invention is directed.

DISCLOSURE OF THE INVENTION

An object of the present invention is to provide a remedy and/or a preventive for diabetes, which bonds to glucokinase to increase the activity of glucokinase, and to provide an anti-obesity agent that activates glucokinase to stimulate a satiety center thereby exhibiting its effect.

We, the present inventors have assiduously studied so as to develop a novel medicine for diabetes, which has a pharmaceutical potency over that of the above-mentioned already-existing medicines for diabetes owing to its effect different from that of the already-existing medicines and which has an additional pharmaceutical potency, and, as a result, have found that a compound represented by a formula (I) has a glucokinase-activating effect and have completed the present invention.

Specifically, the invention relates to:

(1) A compound of a formula (I):

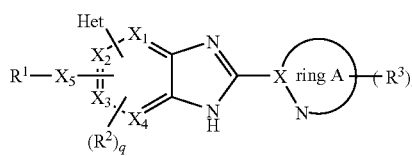

or its pharmaceutically-acceptable salt thereof, wherein:
$X_1$ to $X_4$ each represent a carbon atom or a nitrogen atom;
ring A represents a 5- or 6-membered heteroaryl having from 1 to 4 hetero atoms selected from the group consisting of a nitrogen atom, a sulfur atom and an oxygen atom, represented by a formula (II):

X represents a carbon atom or a nitrogen atom;
Het represents a 5- or 6-membered aliphatic hetero ring having at least any one of an oxygen atom or a sulfur atom in the ring and optionally having, in addition to the oxygen atom or the sulfur atom, one or two hetero atoms selected from the group consisting of a nitrogen atom, a sulfur atom and an oxygen atom in the ring;
said 5- or 6-membered aliphatic hetero ring may be mono- to tri-substituted with the same or different —$C_{1-6}$ alkyl optionally substituted with halogen or lower alkoxy, —O—$C_{1-6}$ alkyl optionally substituted with halogen or lower alkoxy, oxo or thioxo;
$X_5$ represents —O—, —S—, —S(O)—, —S(O)$_2$—, —S(O)$_2$N—, —C(O)— or —NS(O)$_2$—;
$R^1$ represents aryl, —$C_{1-6}$ alkyl or —$C_{3-7}$ cycloalkyl, or represents a 5- or 6-membered heteroaryl having from 1 to 3 hetero atoms selected from the group consisting of a nitrogen atom, a sulfur atom and an oxygen atom in the ring, or a condensed group of the heteroaryl with phenyl or pyridyl;
said $R^1$ may be substituted with from 1 to 4, the same or different $R^4$'s;
$R^2$ each independently represents formyl, —OH, —$C_{1-6}$ alkyl, —$CH_{3-a}F_a$, —$OCH_{3-a}F_a$, amino, cyano, halogen or —(CH$_2$)$_{1-6}$—OH;
$R^3$ each independently represents —$C_{1-6}$ alkyl, —(CH$_2$)$_{1-6}$—OH, —C(O)—O$C_{1-6}$ alkyl, —(CH$_2$)$_{1-6}$—O$C_{1-6}$ alkyl, —(CH$_2$)$_{1-6}$—NH$_2$, cyano, —C(O)—$C_{1-6}$ alkyl, halogen, —$C_{2-6}$ alkenyl, —O$C_{1-6}$ alkyl, —COOH or —OH;
$R^4$ each independently represents —$C_{1-6}$ alkyl optionally substituted with from 1 to 3, the same or different substituents of hydroxy, halogen, —OC(O)—$C_{1-6}$ alkyl or —O$C_{1-6}$ alkyl, wherein —OC(O)—$C_{1-6}$ alkyl may be substituted with from 1 to 3 halogens,
—$C_{3-7}$ cycloalkyl,
—$C_{2-6}$ alkenyl,
—C(O)—N(R$^{51}$)R$^{52}$
—S(O)$_2$—N(R$^{51}$)R$^{52}$,
—O—$C_{1-6}$ alky optionally substituted with halogen or N(R$^{51}$)R$^{52}$,
—S(O)$_{0-2}$—$C_{1-6}$ alkyl,
—C(O)—$C_{1-6}$ alkyl optionally substituted with halogen, amino, CN, hydroxy, —O—$C_{1-6}$ alkyl, —CH$_{3-a}$—F$_a$, —OC(O)—$C_{1-6}$ alkyl, —N(C$_{1-6}$ alkyl)C(O)O—$C_{1-6}$ alkyl, —NH—C(O)O—$C_{1-6}$ alkyl, phenyl, —N(R$^{51}$)R$^{52}$, —NH—C(O)—$C_{1-6}$ alkyl, —N(C$_{1-6}$ alkyl)-C(O)—$C_{1-6}$ alkyl or —NH—S(O)$_{0-2}$—$C_{1-6}$ alkyl,
—C(S)—$C_{3-7}$ cycloalkyl,
—C(S)—$C_{1-6}$ alkyl,
—C(O)—O—$C_{1-6}$ alkyl,
—(CH$_2$)$_{0-4}$—N(R$^{53}$)—C(O)—R$^{54}$,
—N(R$^{53}$)—C(O)—O—R$^{54}$,
—C(O)-aryl optionally substituted with halogen,
—C(O)-aromatic hetero ring,
—C(O)-aliphatic hetero ring,
hetero ring optionally substituted with —$C_{1-6}$ alkyl, said —$C_{1-6}$ alkyl may be substituted with halogen or —O—$C_{1-6}$ alkyl,
phenyl, said phenyl may be substituted with halogen, —$C_{1-6}$ alkyl, —O—$C_{1-6}$ alkyl,
halogen,
CN,
formyl,
COOH,
amino,
oxo,
hydroxy,
hydroxyamidino or
nitro;

$R^{51}$ and $R^{52}$ each independently represent a hydrogen atom or —$C_{1-6}$ alkyl, or $R^{51}$ and $R^{52}$, taken together with the nitrogen atom, form a 4- to 7-membered hetero ring;

$R^{53}$ represents a hydrogen atom or —$C_{1-6}$ alkyl;

$R^{54}$ represents —$C_{1-6}$ alkyl, or the alkyls of $R^{53}$ and $R^{54}$, taken together with —N—C(O)—, form a 4- to 7-membered, nitrogen-containing aliphatic hetero ring, or the alkyls of $R^{53}$ and $R^{54}$, taken together with —N—C(O)—O—, form a 4- to 7-membered, nitrogen-containing aliphatic hetero ring, said aliphatic hetero ring may be substituted with oxo, or said aliphatic hetero ring may have one or two double bonds in the ring;

m indicates an integer of from 0 to 2;

q indicates an integer of from 0 to 2, (2) The compound of above (1) or a pharmaceutically acceptable salt thereof, wherein: $R^1$ is aryl, or 5- or 6-membered heteroaryl having from 1 to 3 hetero atoms selected from the group consisting of a nitrogen atom, a sulfur atom and an oxygen atom in the ring, or a condensed group of the heteroaryl with phenyl or pyridyl, said $R^1$ may be substituted with from 1 to 4, the same or different $R^4$'s, (3) The compound of above (1) or a pharmaceutically acceptable salt thereof, wherein: the ring A is thiazolyl, imidazolyl, isothiazolyl, thiadiazolyl, oxadiazolyl, triazolyl, oxazolyl, isoxazolyl, pyrazinyl, pyridyl, pyridazinyl, pyrazolyl or pyrimidinyl, optionally substituted with from 1 to 3, the same or different $R^3$'s;

$R^1$ is aryl, or 5- or 6-membered heteroaryl having from 1 to 3 hetero atoms selected from the group consisting of a nitrogen atom, a sulfur atom and an oxygen atom in the ring, or a condensed group of the heteroaryl with phenyl or pyridyl, said $R^1$ may be substituted with from 1 to 4, the same or different $R^4$'s, (4) The compound of above (3) or a pharmaceutically acceptable salt thereof, wherein Het is a 5- or 6-membered aliphatic hetero ring having at least one oxygen atom in the ring and having, in addition to the oxygen atom, one or two hetero atoms selected from the group consisting of a nitrogen atom, a sulfur atom and an oxygen atom in the ring, said 5- or 6-membered aliphatic hetero ring may be substituted with —$C_{1-6}$ alkyl, —O—$C_{1-6}$ alkyl, oxo or thioxo, said —$C_{1-6}$ alkyl and —O—$C_{1-6}$ alkyl may be substituted with halogen or lower alkoxy, (5) The compound of above (3) or a pharmaceutically acceptable salt thereof, wherein Het is a 5- or 6-membered aliphatic hetero ring having at least one sulfur atom in the ring and having, in addition to the sulfur atom, one or two hetero atoms selected from the group consisting of a nitrogen atom, a sulfur atom and an oxygen atom in the ring, said 5- or 6-membered aliphatic hetero ring may be substituted with —$C_{1-6}$ alkyl, —O—$C_{1-6}$ alkyl oxo or thioxo, said —$C_{1-6}$ alkyl and —O—$C_{1-6}$ alkyl may be substituted with halogen, O—$C_{1-6}$ alkyl, (6) The compound of above (3) or a pharmaceutically acceptable salt thereof, wherein $X_1$ to $X_4$ are all carbon atoms, (7) The compound of above (3) or a pharmaceutically acceptable salt thereof, wherein $X_5$ is —O—, —S—, —S(O)— or —S(O)$_2$—, (8) The compound of above (1) or a pharmaceutically acceptable salt thereof, wherein the formula (I) is a formula (I-1):

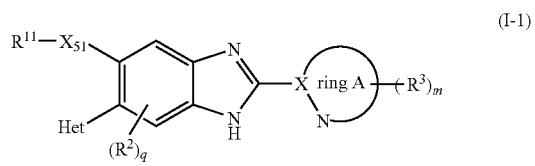

wherein:

$R^{11}$ represents phenyl, or 5- or 6-membered nitrogen-containing heteroaryl having from 1 to 4 hetero atoms selected from the group consisting of a nitrogen atom, a sulfur atom and an oxygen atom in the ring, said $R^{11}$ may be substituted with from 1 to 3, the same or different $R^4$'s;

$X_{51}$ represents —O—, —S—, —S(O)— or —S(O)$_2$—; and the other symbols have the same meanings as above, (9) The compound of above (1) or a pharmaceutically acceptable salt thereof, wherein the compound of formula (I) is:

5-(1,3-dioxolan-2-yl)-6-(4-(ethylsulfonyl)phenoxy)-2-pyridin-2-yl-1H-benzimidazole, 5-(1,3-dioxolan-2-yl)-6-((6-(ethylsulfonyl)pyridin-3-yl)oxy)-2-pyridin-2-yl-1H-benzimidazole, 5-(4-(hydroxymethyl)-1,3-dioxolan-2-yl)-6-(4-(ethylsulfonyl)phenoxy)-2-pyridin-2-yl-1H-benzimidazole, 5-(1,3-dioxan-2-yl)-6-(4-(ethylsulfonyl)phenoxy)-2-pyridin-2-yl-1H-benzimidazole, 5-(3-acetyl-1,3-oxazolidin-2-yl)-6-(4-(ethylsulfonyl)phenoxy)-2-pyridin-2-yl-1H-benzimidazole, 5-(6-(4-(ethylsulfonyl)phenoxy)-2-pyridin-2-yl-1H-benzimidazol-5-yl)tetrahydrofuran-2-ol, 5-(tetrahydrofuran-2-yl)-6-(4-(ethylsulfonyl)phenoxy)-2-pyridin-2-yl-1H-benzimidazole, 5-(tetrahydrofuran-2-yl)-6-(4-(ethylsulfonyl)phenoxy)-2-pyridin-2-yl-1H-benzimidazol enantiomer A and enantiomer B, 5-(6-(4-(ethylsulfonyl)phenoxy-2-pyrazin-2-yl-1H-benzimidazol-5-yl)tetrahydrofuran-2-ol, 5-(tetrahydrofuran-2-yl)-6-(4-(ethylsulfonyl)phenoxy)-2-pyrazin-2-yl-1H-benzimidazole, 5-(tetrahydrofuran-2-yl)-6-((6-(ethylsulfonyl)pyridin-3-yl)oxy)-2-pyridin-2-yl-1H-benzimidazole, 5-(6-((6-(ethylsulfonyl)pyridin-3-yl)oxy)-2-pyridin-2-yl-1H-benzimidazol-5-yl)tetrahydrofuran-2-ol, 5-(6-((6-(ethylsulfonyl)pyridin-3-yl)oxy)-2-pyridin-2-yl-1H-benzimidazol-5-yl)tetrahydrofuran-2-ol enantiomer A, 5-(6-((6-(ethylsulfonyl)pyridin-3-yl)oxy)-2-pyrazin-2-yl-1H-benzimidazol-5-yl)tetrahydrofuran-2-ol, 5-(tetrahydrofuran-2-yl)-6-((6-(ethylsulfonyl)pyridin-3-yl)oxy)-2-pyrazin-2-yl-1H-benzimidazole, 5-(tetrahydrofuran-2-yl)-6-(4-(methylsulfonyl)phenoxy)-2-pyridin-2-yl-1H-benzimidazole, 5-(tetrahydrofuran-2-yl)-6-(6-(5-methyl-(1,2,4)oxadiazol-3-yl)-pyridin-3-yloxy)-2-pyridin-2-yl-1H-benzimidazole, 5-(tetrahydrofuran-2-yl)-6-((6-(methylsulfonyl)pyridin-3-yl)oxy)-2-pyridin-2-yl-1H-benzimidazole, 5-(4-methyltetrahydrofuran-2-yl)-6-(4-(methylsulfonyl)phenoxy)-2-pyridin-2-yl-1H-benzimidazole, 5-(6-(4-(methylsulfonyl)phenoxy)-2-pyridin-2-yl-1H-benzimidazol-5-yl)tetrahydrofuran-2-ol, 5-(6-(4-(ethylsulfonyl)phenoxy)-2-pyridin-2-yl-1H-benzimidazol-5-yl)dihydrofuran-2(3H)-one, 5-(6-(4-(ethylsulfonyl)phenoxy)-2-pyridin-2-yl-1H-benzimidazol-5-yl)dihydrofuran-2(3H)-one enantiomer A and enantiomer B, 5-(6-(4-(ethylsulfonyl)phenoxy)-2-pyrazin-2-yl-1H-benz-
imidazol-5-yl)dihydrofuran-2(3H)-one,
5-(6-((6-methylsulfonyl)pyridin-3-yl)oxy)-2-pyridin-2-yl-
1H-benzimidazol-5-yl)dihydrofuran-2(3H)-one,
5-(6-(5-methyl-(1,2,4)oxadiazol-3-yl)-pyridin-3-yloxy)-2-
pyridin-2-yl-1H-benzimidazol-5-yl)dihydrofuran-2(3H)-
one,
5-(6-((6-(ethylsulfonyl)pyridin-3-yl)oxy)-2-pyridin-2-yl-
1H-benzimidazol-5-yl)dihydrofuran-2(3H)-one,
5-(6-((6-(ethylsulfonyl)pyridin-3-yl)oxy)-2-pyridin-2-yl-
1H-benzimidazol-5-yl)dihydrofuran-2(3H)-one enanti-
omer A and enantiomer B,
5-(6-((6-ethylsulfonyl)pyridin-3-yl)oxy)-2-pyrazin-2-yl-
1H-benzimidazol-5-yl)dihydrofuran-2(3H)-one,
5-(tetrahydro-2-thienyl)-6-(4-(ethylsulfonyl)phenoxy)-2-
pyridin-2-yl-1H-benzimidazole and 5-(1,2-dithian-3-yl)-
6-(4-(ethylsulfonyl)phenoxy)-2-pyridin-2-yl-1H-benz-
imidazole,
5-(1-oxidotetrahydro-2-thienyl)-6-(4-(ethylsulfonyl)phe-
noxy)-2-pyridin-2-yl-1H-benzimidazole and 5-(1,1-dioxi-
dotetrahydro-2-thienyl)-6-(4-(ethylsulfonyl)phenoxy)-2-
pyridin-2-yl-1H-benzimidazole,
5-(6-(4-(ethylsulfonyl)phenoxy)-2-pyridin-2-yl-1H-benz-
imidazol-5-yl)-3-methyl-1,3-oxazolidine-2,4-dione,
5-(6-((6-(ethylsulfonyl)pyridin-3-yl)oxy)-2-pyridin-2-yl-
1H-benzimidazol-5-yl)-3-methyl-1,3-oxazolidine-2,4-di-
one,
5-(6-(4-(ethylsulfonyl)phenoxy)-2-pyridin-2-yl-1H-benz-
imidazol-5-yl)-1,3-oxazolidine-2,4-dione,
5-(6-(4-(ethylsulfonyl)phenoxy)-2-pyridin-2-yl-1H-benz-
imidazol-5-yl)-2,2-dimethyl-1,3-dioxolan-4-one,
4-(6-(4-(ethylsulfonyl)phenoxy)-2-pyridin-2-yl-1H-benz-
imidazol-5-yl)-1,3-dioxolan-2-one,
3-(6-(4-(ethylsulfonyl)phenoxy)-2-pyridin-2-yl-1H-benz-
imidazol-5-yl)dihydrofuran-2(3H)-one,
3-(6-((6-(ethylsulfonyl)pyridin-3-yl)oxy)-2-pyridin-2-yl-
1H-benzimidazol-5-yl)dihydrofuran-2(3H)-one,
5-(tetrahydrofuran-3-yl)-6-((6-(ethylsulfonyl)pyridin-3-yl)
oxy)-2-pyridin-2-yl-1H-benzimidazol, or
5-(6-((6-(cyanopyridin-3-yl)oxy)-2-pyridin-2-yl-1H-benz-
imidazol-5-yl)dihydrofuran-2(3H)-one,
(10) A pharmaceutical composition for treatment, preven-
tion and/or retardation of onset of type-II diabetes, compris-
ing the following (A) to (C):
(A) a compound of any one of above (1) to (9),
(B) one or more compounds selected from the following
groups (a) to (h):
(a) any other glucokinase activator,
(b) a bis-guanide,
(c) a PPAR agonist,
(d) an insulin,
(e) a somatostatin,
(f) an α-glucosidase inhibitor,
(g) an insulin secretion promoter, and
(h) a DPP-IV (dipeptidyl peptidase IV) inhibitor,
(C) a pharmaceutically-acceptable carrier,
(11) A glucokinase activator comprising a compound or its
pharmaceutically-acceptable salt of any one of above (1) to
(9), as the active ingredient thereof,
(12) A remedy and/or a prevention for diabetes, comprising
a compound or its pharmaceutically-acceptable salt of any
one of above (1) to (9), as the active ingredient thereof,
(13) A remedy and/or a preventive for obesity, comprising
a compound or its pharmaceutically-acceptable salt of any
one of above (1) to (9), as the active ingredient thereof.

BEST MODE FOR CARRYING OUT THE
INVENTION

The meanings of the terms used in this description are described below, and the compounds of the invention are described in more detail hereinunder.

Unless otherwise specifically indicated in this description, the following groups have the meanings described below.

"Aryl" preferably means a hydrocarbon aromatic ring having from 6 to 14 carbon atoms, including, for example, phenyl, naphthyl, biphenyl, anthryl. Of those, preferred are phenyl, naphthyl and biphenyl; and more preferred is phenyl.

"$C_{1-6}$ alkyl" means a linear or branched alkyl having from 1 to 6 carbon atoms, including, for example, methyl, ethyl, propyl, isopropyl, butyl, isobutyl, sec-butyl, tert-butyl, pentyl, isoamyl, neopentyl, isopentyl, 1,1-dimethylpropyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,2,2-trimethylpropyl, 1-ethyl-2-methylpropyl.

"$C_{2-6}$ alkenyl" means a linear or branched alkenyl having from 2 to 6 carbon atoms, including, for example, allyl, 2-propenyl, 1-butenyl, 2-butenyl, 2-methyl-2-butenyl, 1-pentenyl.

"$C_{3-7}$ cycloalkyl" concretely includes cyclopropyl, cyclobutyl, cyclopentyl, cyclohexyl, cycloheptyl.

"Halogen" means fluorine, chlorine, bromine, iodine.

"—$(CH_2)_{1-6}$—OH" includes, for example, hydroxymethylene, hydroxyethylene.

"—O—$C_{1-6}$ alkyl" includes, for example, methoxy, ethoxy, propoxy or tert-butoxy.

"—$(CH_2)_{1-6}$—$OC_{1-6}$ alkyl" includes, for example, methoxymethyl, methoxyethyl, propyloxymethyl, isopropyloxymethyl.

"—$C(O)$-$_{1-6}$ alkyl" includes, for example, acetyl, ethylcarbonyl, isopropylcarbonyl, propylcarbonyl.

"—$C(O)OC_{1-6}$ alkyl" includes, for example, methoxycarbonyl, ethoxycarbonyl, tert-butoxycarbonyl.

"—$(CH_2)_{1-6}$—$NH_2$" includes, for example, aminomethyl, aminoethyl, aminopropyl.

"—NH—$C_{1-6}$ alkyl" includes, for example, methylamino, ethylamino, propylamino, 2-methylbutylamino.

"—N-di-($C_{1-6}$ alkyl)" means a group composed of the above-mentioned, same or different "$C_{1-6}$ alkyls" and N bonding to each other, and includes, for example, dimethylamino, ethylpropylamino, 2-methylbutyl-1-methylamino. The same or different $C_{1-6}$ alkyls in "—N-di-($C_{1-6}$ alkyl)", taken together with the nitrogen atom, may form a ring. Examples of the ring are piperidine, pyrrolidine.

"—$CH_{3-a}F_a$" means a group of methyl in which from 1 to 3 hydrogen atoms are substituted with a fluorine atom, and includes, for example, trifluoromethyl, difluoromethyl or fluoromethyl.

"—$OCH_{3-a}F_a$" means a group composed of the above-defined "—$CH_{3-a}F_a$" and an oxygen atom bonding to each other, and includes, for example, trifluoromethoxy, difluoromethoxy or fluoromethoxy.

a indicate an integer of from 1 to 3.

For further more concretely disclosing the compounds of the invention of formula (I):

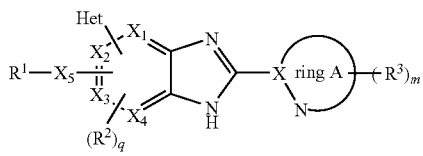

(wherein the symbols have the same meanings as above), the symbols used in the formula (I) are described with reference to their concrete examples.

$X_1$ to $X_4$ each represent a carbon atom or a nitrogen atom. Preferably, all of $X_1$ to $X_4$ are carbon atoms; or any one or two of $X_1$ to $X_4$ are nitrogen atom. More preferably, all of $X_1$ to $X_4$ are carbon atoms.

The ring A represents a 5- or 6-membered heteroaryl having from 1 to 3 hetero atoms selected from the group consisting of a nitrogen atom, a sulfur atom and an oxygen atom, represented by a formula (II):

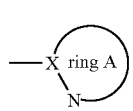

or represents a condensed group of the 5- or 6-membered heteroaryl with a phenyl ring or a pyridine ring.

X means a carbon atom or a nitrogen atom.

The ring A includes, for example, thiazolyl, imidazolyl, isothiazolyl, thiadiazolyl, oxadiazolyl, triazolyl, oxazolyl, isoxazolyl, pyrazinyl, pyridyl, pyridazinyl, pyrazolyl or pyrimidinyl. Of those, preferred are thiazolyl, thiadiazolyl, isoxazolyl, pyrazinyl, pyridyl, pyridazinyl, triazolyl, pyrazolyl; more preferred are pyridyl, pyrazinyl, thiazolyl, isoxazolyl, pyrazolyl; and even more preferred are pyridyl, pyrazolyl.

The ring A may have one or two, the same or different substituents shown in $R^3$. $R^3$ each independently represents —$C_{1-6}$ alkyl, —$(CH_2)_{1-6}$—OH, —C(O)—O$C_{1-6}$ alkyl, —$(CH_2)_{1-6}$—$C_{1-6}$ alkyl, —$(CH_2)_{1-6}$—$NH_2$, cyano, —C(O)—$C_{1-6}$ alkyl, halogen, —$C_{2-6}$ alkenyl, —O$C_{1-6}$ alkyl, —COOH or —OH.

"—$C_{1-6}$ alkyl" for $R^3$ has the same meaning as the above-defined "—$C_{1-6}$ alkyl".

"—$(CH_2)_{1-6}$—O$C_{1-6}$ alkyl" for $R^3$ has the same meaning as the above-defined "—$(CH_2)_{1-6}$—O$C_{1-6}$ alkyl".

"—C(O)—O$C_{1-6}$ alkyl" for $R^3$ has the same meaning as the above-defined "—C(O)—O$C_{1-6}$ alkyl".

"—C(O)—$C_{1-6}$ alkyl" for $R^3$ has the same meaning as the above-defined "—C(O)—$C_{1-6}$ alkyl".

"Halogen" for $R^3$ has the same meaning as the above-defined "halogen".

"—$C_{2-6}$ alkenyl" for $R^3$ has the same meaning as the above-defined "—$C_{2-6}$ alkenyl".

"—O$C_{1-6}$ alkyl" for $R^3$ has the same meaning as the above-defined "—O$C_{1-6}$ alkyl".

Het represents a 5- or 6-membered aliphatic hetero ring having at least any one of an oxygen atom or a sulfur atom in the ring and having, in addition to the oxygen atom or the sulfur atom, one or two hetero atoms selected from the group consisting of a nitrogen atom, a sulfur atom and an oxygen atom in the ring.

Preferably, Het is a 5- or 6-membered aliphatic hetero ring having at least any one of an oxygen atom or a sulfur atom in the ring and having, in addition to the oxygen atom or the sulfur atom, one hetero atom selected from the group consisting of a nitrogen atom, a sulfur atom and an oxygen atom in the ring.

Het may be mono- to tri-substituted with the same or different with —$C_{1-6}$ alkyl, —O—$C_{1-6}$ alkyl (the —$C_{1-6}$ alkyl and —O—$C_{1-6}$ alkyl may be substituted with halogen, —O—$C_{1-6}$ alkyl), oxo or thioxo.

"—$C_{1-6}$ alkyl" for the substituent has the same meaning as the above-defined "—$C_{1-6}$ alkyl".

"—O—$C_{1-6}$ alkyl" for the substituent has the same meaning as the above-defined "—O—$C_{1-6}$ alkyl".

"Halogen" for the substituent has the same meaning as the above-defined "halogen". —$C_{1-6}$ alkyl and —O—$C_{1-6}$ alkyl may be substituted with from 1 to 3, the same or different substituents of halogen such as fluorine, chlorine or bromine, or lower alkoxy such as methoxy, ethoxy or isopropoxy.

For the substituent which Het may have, mentioned are methyl, ethyl, oxo, hydroxy, alkoxy and fluorine of the above-mentioned substituents; and Het may have from 1 to 3, the same or different such substituents.

From the above, Het optionally substituted with from 1 to 3, the same or different substituents concretely includes, for example, groups of a formula (III):

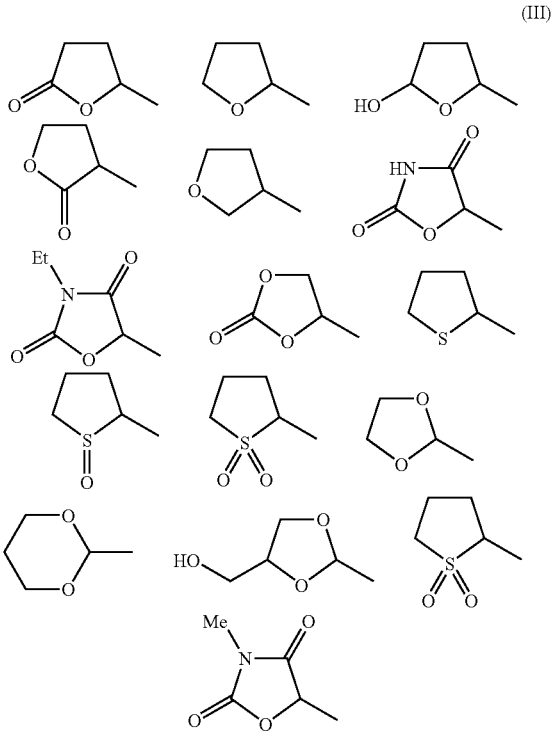

$X_5$ represents —O—, —S—, —S(O)—, —S(O)$_2$—, —S(O)$_2$N—, —C(O)— or —NS(O)$_2$—.

$X_5$ is preferably —O—, —S—, —S(O)— or —S(O)$_2$—, more preferably —O—.

$R^1$ represents aryl, —$C_{1-6}$ alkyl or —$C_{3-7}$ cycloalkyl, or represents a 5- or 6-membered heteroaryl having from 1 to 3 hetero atoms selected from the group consisting of a nitrogen atom, a sulfur atom and an oxygen atom in the ring, or a condensed group of the heteroaryl with phenyl or pyridyl, or represents a 9- or 10-membered bicyclic group having 2 or 3 nitrogen atoms in the ring.

"Aryl" for $R^1$ has the same meaning as the above-defined "aryl". Concretely, for example, it is preferably phenyl, naphthyl or biphenyl, more preferably phenyl.

"—$C_{1-6}$ alkyl" for $R^1$ has the same meaning as the above-defined "—$C_{1-6}$ alkyl", and concretely includes, for example, methyl, ethyl, propyl, isopropyl.

"—$C_{3-7}$ cycloalkyl" for $R^1$ has the same meaning as the above-defined "—$C_{3-7}$ cycloalkyl", and concretely includes, for example, cyclopropyl, cyclobutyl, cyclopentyl, cyclohexyl, cycloheptyl.

Concretely, "5- or 6-membered heteroaryl having from 1 to 3 hetero atoms selected from the group consisting of a nitrogen atom, a sulfur atom and an oxygen atom in the ring" for $R^1$ is preferably pyridyl, pyrazinyl, pyrimidinyl, more preferably pyridyl or pyrazinyl.

Of those, $R^1$ is preferably phenyl, pyridyl, pyrazinyl, pyrimidinyl, more preferably phenyl, pyridyl.

$R^1$ may be substituted with from 1 to 4, the same or different $R^4$'s, preferably may be substituted with one or two, the same or different $R^4$'s.

$R^4$ represents —$C_{1-6}$ alkyl (the alkyl may be substituted with from 1 to 3, the same or different substituents of hydroxy, halogen, —OC(O)—$C_{1-6}$ alkyl (the alkyl may be substituted with from 1 to 3 halogens) or —O$C_{1-6}$ alkyl),
—$C_{3-7}$ cycloalkyl,
—$C_{2-6}$ alkenyl,
—C(O)—N($R^{51}$)$R^{52}$,
—S(O)$_2$—N($R^{51}$)$R^{52}$,
—O—$C_{1-6}$ alkyl ($C_{1-6}$ alkyl may be substituted with halogen or N($R^{51}$)$R^{52}$),
—S(O)$_{0-2}$—$C_{1-6}$ alkyl,
—C(O)—$C_{1-6}$ alkyl ($C_{1-6}$ alkyl may be substituted with halogen, amino, CN, hydroxy, —O—$C_{1-6}$ alkyl, —$CH_{3-a}F_a$, —OC(O)—$C_{1-6}$ alkyl, —N($C_{1-6}$ alkyl)C(O)O—$C_{1-6}$ alkyl, —NH—C(O)O—$C_{1-6}$ alkyl, phenyl, —N($R^{51}$)$R^{52}$, —NH—C(O)—$C_{1-6}$ alkyl, —N($C_{1-6}$ alkyl)-C(O)—$C_{1-6}$ alkyl or —NH—S(O)$_{0-2}$—$C_{1-6}$ alkyl),
—C(S)—$C_{3-7}$ cycloalkyl,
—C(S)—$C_{1-6}$ alkyl,
—C(O)—O—$C_{1-6}$ alkyl,
—($CH_2$)$_{0-4}$—N($R^{53}$)—C(O)—$R^{54}$,
—N($R^{53}$)—C(O)—O—$R^{54}$,
—C(O)-aryl (the aryl may be substituted with halogen),
—C(O)-aromatic hetero ring,
—C(O)-aliphatic hetero ring,
hetero ring (the hetero ring may be substituted with —$C_{1-6}$ alkyl (—$C_{1-6}$ alkyl may be substituted with halogen or —O—$C_{1-6}$ alkyl)),
phenyl (the phenyl may be substituted with halogen, —$C_{1-6}$ alkyl, —O—$C_{1-6}$ alkyl),
halogen, CN, formyl, COOH, amino, oxo, hydroxy, hydroxyamidino or nitro.

"Halogen" for $R^4$ has the same meaning as the above-defined group.

"—$C_{1-6}$ alkyl" for $R^4$ means a linear or branched alkyl having from 1 to 6 carbon atoms, including, for example, methyl, ethyl, propyl, isopropyl, butyl, isobutyl, sec-butyl, tert-butyl, pentyl, isoamyl, neopentyl, isopentyl, 1,1-dimethylpropyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,2,2-trimethylpropyl, 1-ethyl-2-methylpropyl.

"—$C_{1-6}$ alkyl" may be substituted with from 1 to 3 substituents of hydroxy, —OC(O)—$C_{1-6}$ alkyl(the alkyl may be substituted with from 1 to 3 halogens) or —O—$C_{1-6}$ alkyl.

In case where "—$C_{1-6}$ alkyl" has the above-mentioned two or three substituents, they may be the same or different.

The halogen for the substituent has the same meaning as the above-defined halogen.

—OC(O)—$C_{1-6}$ alkyl for the substituent includes, for example, methylcarbonyloxy, ethylcarbonyloxy, isopropylcarbonyloxy.

—OC(O)—$C_{1-6}$ alkyl for the substituent may be substituted with from 1 to 3, the above-defined halogen atoms.

—O—$C_{1-6}$ alkyl for the substituent includes, for example, methoxy, ethoxy, propoxy, isopropoxy.

"—S(O)$_{0-2}$—$C_{1-6}$ alkyl" for $R^4$ means a group composed of —S(O)$_{0-2}$— and the above-defined —$C_{1-6}$ alkyl, and includes, for example, —S-ethyl, —S-methyl, —S-isopropyl, —S-propyl-, —S(O)$_2$-methyl, —S(O)$_2$-ethyl.

—$C_{1-6}$ alkyl in "—S(O)$_{0-2}$—$C_{1-6}$ alkyl" may be substituted with hydroxy.

"—$C_{3-8}$ cycloalkyl" for $R^4$ has the same meaning as that of the above-defined one.

"—$C_{2-6}$ alkenyl" for $R^4$ has the same meaning as that of the above-defined one.

"C(O)N($R^{51}$)$R^{52}$" for $R^4$ means a substituted or unsubstituted carbamoyl group; or means a group composed of a 4- to 7-membered aliphatic hetero ring formed by N, $R^{51}$ and $R^{52}$, and carbonyl bonding to each other.

Of "C(O)N($R^{51}$)$R^{52}$" for $R^4$, the substituted or unsubstituted carbamoyl includes, for example, carbamoyl, methylcarbamoyl, ethylcarbamoyl, isopropylcarbamoyl, propylcarbamoyl, ethylmethylcarbamoyl, dimethylcarbamoyl, isopropylmethylcarbamoyl, diisopropylcarbamoyl, diethylcarbamoyl.

Of "C(O)N($R^{51}$)$R^{52}$" for $R^4$, the 4- to 7-membered aliphatic group to be formed by N, $R^{51}$ and $R^{52}$ taken together concretely includes, for example, azetidinyl, pyrrolidinyl, piperidino, piperazinyl, morpholino. Accordingly, C(O)N($R^{51}$)$R^{52}$ includes azetidine-1-carbonyl, pyrrolidine-1-carbonyl, piperidine-1-carbonyl, piperazine-1-carbonyl, morpholine-1-carbonyl.

"—C(O)—O—$C_{1-6}$ alkyl" for $R^4$ has the same meaning as the above-defined "—C(O)—O—$C_{1-6}$ alkyl".

"—O—$C_{1-6}$ alkyl" for $R^4$ has the same meaning as the above-defined "—O—$C_{1-6}$ alkyl". —O—$C_{1-6}$ alkyl may be substituted with halogen or N($R^{51}$)$R^{52}$.

"—C(O)—$C_{1-6}$ alkyl" for $R^4$ has the same meaning as the above-defined "—C(O)—$C_{1-6}$ alkyl".

"—C(O)—$C_{1-6}$ alkyl" may be substituted with halogen, amino, —$CH_{3-a}F_a$, CN, hydroxy, —O—$C_{1-6}$ alkyl, —O—C(O)—$C_{1-6}$ alkyl, —N—($C_{1-6}$ alkyl)-C(O)O—$C_{1-6}$ alkyl, —NH—C(O)O—$C_{1-6}$ alkyl, phenyl, —N($R^{51}$)$R^{52}$, —NH—C(O)—$C_{1-6}$ alkyl, —N—($C_{1-6}$ alkyl)-C(O)—$C_{1-6}$ alkyl or —NH—S(O)$_{0-2}$—$C_{1-6}$ alkyl.

"Halogen" for the substituent has the same meaning as the above-defined halogen.

"—$CH_{3-a}F_a$" for the substituent has the same meaning as the above-defined "—$CH_{3-a}F_a$".

"—O—$C_{1-6}$ alkyl" for the substituent has the same meaning as the above-defined "—O—$C_{1-6}$ alkyl".

"—O—C(O)—$C_{1-6}$ alkyl" for the substituent has the same meaning as the above-defined "—O—C(O)—$C_{1-6}$ alkyl".

"—N—($C_{1-6}$ alkyl)-C(O)O—$C_{1-6}$ alkyl" for the substituent means a group composed of —N—($C_{1-6}$ alkyl)- and the above-defined-C(O)O—$C_{1-6}$ alkyl bonding to each other, and concretely it includes, for example, —N(Me)-C(O)O-tert-butyl.

"—NH—C(O)O—$C_{1-6}$ alkyl" for the substituent means a group composed of —NH— and the above-mentioned —C(O)O—$C_{1-6}$ alkyl bonding to each other, and concretely it includes, for example, —NH—C(O)O-methyl, —NH—C(O)O-ethyl, —NH—C(O)O-isopropyl, —NH—C(O)-propyl.

"—N($R^{51}$)$R^{52}$" for the substituent has the same meaning as the above-defined "—N($R^{51}$)$R^{52}$".

"—NH—C(O)—$C_{1-6}$ alkyl" for the substituent means a group composed of —NH—C(O)— and the above-defined —$C_{1-6}$ alkyl bonding to each other, and concretely it includes, for example, —NH—C(O)-methyl, —NH—C(O)-ethyl, —NH—C(O)-isopropyl, —NH—C(O)-propyl.

"—N—($C_{1-6}$ alkyl)-C(O)—$C_{1-6}$ alkyl" for the substituent means a group composed of "—N—($C_{1-6}$ alkyl)-C(O)— and the above-defined-$C_{1-6}$ alkyl bonding to each other, and concretely it includes, for example, —N(methyl)-C(O)-methyl, —N(Methyl)-C(O)-ethyl, —N(ethyl)-C(O)-isopropyl, —N(methyl)-C(O)-isopropyl, —N(isopropyl)-C(O)-methyl.

—NH—S(O)$_{0-2}$—$C_{1-6}$ alkyl for the substituent means a group composed of —NH— and the above-defined —S(O)$_{0-2}$—$C_{1-6}$ alkyl bonding to each other, and concretely it includes, for example, —NH—S(O)$_2$-methyl, —NH—S(O)$_2$-ethyl, —NH—S(O)$_2$-isopropyl.

"—C(O)—$C_{1-6}$ alkyl" optionally having the above-mentioned substituent on the $C_{1-6}$ alkyl concretely includes, for example, fluoromethylcarbonyl, 2,2,2-trifluoroethylcarbonyl, cyanomethylcarbonyl, hydroxymethylcarbonyl, 2-hydroxyethylcarbonyl, methoxymethylcarbonyl, aminomethylcarbonyl, N-methylaminocarbonyl, 2-phenylethylcarbonyl.

"—C(S)—$C_{1-6}$ alkyl" for $R^4$ means a group composed of —C(S)— and the above-defined "—$C_{1-6}$ alkyl" bonding to each other, and concretely it includes, for example, —C(S)-methyl, —C(S)-ethyl, —C(S)-isopropyl, —C(S)-propyl.

In "—(CH$_2$)$_{0-4}$—N($R^{53}$)—C(O)—$R^{54}$" for $R^4$, $R^{53}$ represents a hydrogen atom or —$C_{1-6}$ alkyl, and $R^{54}$ represents —$C_{1-6}$ alkyl; or in "—N($R^{53}$)—C(O)—$R^{54}$" in "—(CH$_2$)$_{0-4}$—N($R^{53}$)—C(O)—$R^{54}$", —N—C(O)— and the alkyls of $R^{53}$ and $R^{54}$, taken together, form a 4- to 7-membered nitrogen-containing aliphatic hetero ring (the hetero ring may be substituted with oxo, or may have one or two double bonds in the ring).

Concretely, "—(CH$_2$)$_{0-4}$—N($R^{53}$)—C(O)—$R^{54}$", in which $R^{53}$ is a hydrogen atom or —$C_{1-6}$ alkyl, and $R^{54}$ is —$C_{1-6}$ alkyl, includes, for example, —CH$_2$—NH—C(O)-methyl, —CH$_2$—NH—C(O)-ethyl, —CH$_2$—NH—C(O)-isopropyl, —CH$_2$—NH—C(O)-propyl, —CH$_2$—N(methyl)-C(O)-methyl, —CH$_2$—N(ethyl)-C(O)-methyl, —NH—C(O)-methyl, —NH—C(O)-ethyl, —NH—C(O)-isopropyl, —NH—C(O)-propyl, —N(methyl)-C(O)-methyl, —N(ethyl)-C(O)-methyl.

Concretely, "—(CH$_2$)$_{0-4}$—N($R^{53}$)—C(O)—$R^{54}$, in which —N—C(O)— and the $C_{1-6}$ alkyls of $R^{53}$ and $R^{54}$, taken together, form a 4- to 7-membered nitrogen-containing aliphatic hetero ring (the hetero ring may be substituted with oxo, or may have one or two double bonds in the ring), includes, for example, groups of a formula (IV):

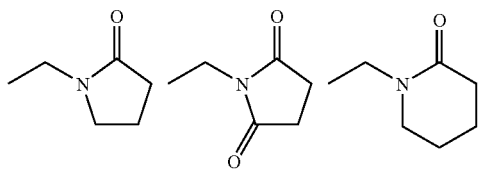

(IV)

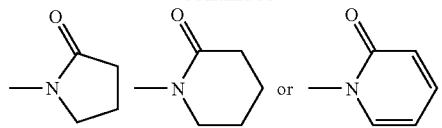

In "—N($R^{55}$)—C(O)—O—$R^{56}$" for $R^4$, $R^{55}$ represents a hydrogen atom or —$C_{1-6}$ alkyl, and $R^{56}$ represents —$C_{1-6}$ alkyl; or in "—N($R^{55}$)—C(O)—O—$R^{56}$", —N—C(O)—O— and the alkyls of $R^{55}$ and $R^{56}$, taken together, form a 4 to 7-membered nitrogen-containing aliphatic hetero ring.

Concretely, "—N($R^{55}$)—C(O)—O—$R^{56}$", in which $R^{55}$ is a hydrogen atom or —$C_{1-6}$ alkyl, and $R^{56}$ is —$C_{1-6}$ alkyl, includes, for example, —NH—C(O)—O-methyl, —NH—C(O)—O-ethyl, —NH—C(O)—O-isopropyl, —NH—C(O)—O-propyl, —N(methyl)-C(O)—O-methyl, —N(ethyl)-C(O)—O-methyl.

Concretely, "—N($R^{53}$)—C(O)—O—$R^{54}$", in which —N—C(O)—O— and the $C_{1-6}$ alkyls of $R^{55}$ and $R^{56}$, taken together, form a 4 to 7-membered nitrogen-containing aliphatic hetero ring includes, for example, groups of a formula (V):

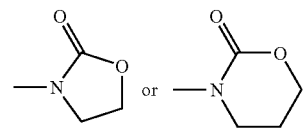

(V)

"—C(O)-aryl" for $R^4$ means a group composed of carbonyl and the above-defined aryl bonding to each other, and concretely it includes, for example, benzoyl, naphthylcarbonyl.

The aryl in "—C(O)-aryl" may be substituted with from 1 to 3, the above-defined halogen atoms.

In case where the group is substituted with 2 or 3 halogen atoms, they may be the same or different.

"—C(O)-aromatic hetero ring" for $R^4$ means a group composed of carbonyl and the above-defined, 5- or 6-membered, monocyclic aromatic hetero ring or 9- or 10-membered bicyclic aromatic hetero ring bonding to each other, and concretely it includes for example, —C(O)-pyrrolyl, —C(O)-fury, —C(O)-thienyl, —C(O)—, —C(O)-pyrazolyl, —C(O)-isoxazolyl, —C(O)-isothiazolyl, —C(O)-imidazolyl, —C(O)-oxazolyl, —C(O)-thiazolyl, —C(O)-triazolyl, —C(O)-oxadiazolyl, —C(O)-thiadiazolyl, —C(O)-tetrazolyl, —C(O)-pyridyl, —C(O)-pyrazinyl, —C(O)-pyrimidinyl, —C(O)-pyridazinyl.

"—C(O)-aliphatic hetero ring" for $R^4$ means a group composed of carbonyl and the above-defined 4- to 7-membered, monocyclic aliphatic hetero ring bonding to each other, and concretely it includes, for example, —C(O)-azetidinyl, —C(O)-pyrrolidinyl, —C(O)-piperidino, —C(O)-piperidinyl, —C(O)-azepanyl, —C(O)-piperazinyl, —C(O)-morpholino, —C(O)-thiomorpholino, —C(O)-homopiperazinyl, —C(O)-imidazolidinyl, —C(O)-pyrazolidinyl.

"Hetero ring" for $R^4$ has the same meaning as that of the ring A.

The hetero ring may be substituted with from 1 to 3 substituents of —$C_{1-6}$-alkyl, halogen or —O—$C_{1-6}$-alkyl.

In case where the group has 2 or 3 substituents, then they may be the same or different.

—$C_{1-6}$ alkyl, halogen and —O—$C_{1-6}$ alkyl for the substituent have the same meanings as those mentioned above.

"Halogen" for $R^4$ has the same meaning as the above-defined "halogen".

"Phenyl" for $R^4$ may be substituted with halogen, —$C_{1-6}$ alkyl or —O—$C_{1-6}$ alkyl.

In case where $R^1$ has 2 or 3 $R^4$'s as the substituents, the same or different $R^4$'s, taken together, may form a 4- to 6-membered ring, which concretely includes, for example, groups of a formula (VI):

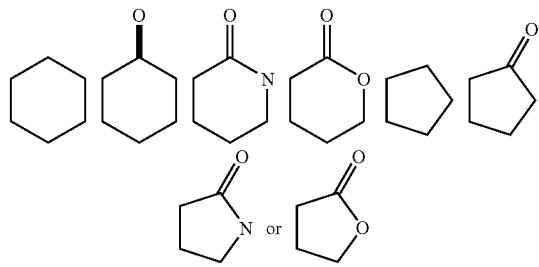

(VI)

$R^2$ each independently represents formyl, —OH, —$C_{1-6}$ alkyl, —$CH_{3-a}F_a$, —$OCH_{3-a}F_a$, amino, cyano, halogen or —$(CH_2)_{1-6}$—OH.

$R^2$ is preferably hydroxy, formyl, —$CH_{3-a}F_a$ (preferably trifluoromethyl), —$OCH_{3-a}F_a$, halogen, —$C_{1-6}$ alkyl, amino, CN, —$(CH_2)_{1-4}$OH; more preferably hydroxy, formyl, —$CH_{3-a}F_a$ (preferably trifluoromethyl), —$OCH_{3-a}F_a$ (preferably trifluoromethoxy), amino, halogen, —$C_{1-6}$ alkyl, CN or —$(CH_2)_{1-4}$OH; even more preferably hydroxy, formyl, amino, halogen (preferably fluorine, chlorine), —$C_{1-6}$ alkyl or —$(CH_2)_{1-4}$OH.

In the above formula (I), the bonding position of the group of a formula (VII):

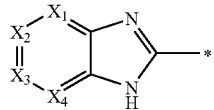

(VII)

(wherein * indicates the bonding position to the ring A; and $X_1$ to $X_4$ have the same meanings as above) to —$X_5$—$R^1$ and Het is preferably represented by a formula (VII-1):

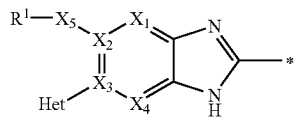

(VII-1)

(wherein the symbols have the same meanings as above).

The compounds of formula (I) includes, for example, the following:

5-(1,3-dioxolan-2-yl)-6-(4-(ethylsulfonyl)phenoxy)-2-pyridin-2-yl-1H-benzimidazole,
5-(1,3-dioxolan-2-yl)-6-((6-(ethyl sulfonyl)pyridin-3-yl)oxy)-2-pyridin-2-yl-1H-benzimidazole,
5-(4-(hydroxymethyl)-1,3-dioxolan-2-yl)-6-(4-(ethylsulfonyl)phenoxy)-2-pyridin-2-yl-1H-benzimidazole,
5-(1,3-dioxan-2-yl)-6-(4-(ethylsulfonyl)phenoxy)-2-pyridin-2-yl-1H-benzimidazole,
5-(3-acetyl-1,3-oxazolidin-2-yl)-6-(4-(ethyl sulfonyl)phenoxy)-2-pyridin-2-yl-1H-benzimidazole,
5-(6-(4-(ethylsulfonyl)phenoxy)-2-pyridin-2-yl-1H-benzimidazol-5-yl)tetrahydrofuran-2-ol,
5-(tetrahydrofuran-2-yl)-6-(4-(ethylsulfonyl)phenoxy)-2-pyridin-2-yl-1H-benzimidazole,
5-(tetrahydrofuran-2-yl)-6-(4-(ethylsulfonyl)phenoxy)-2-pyridin-2-yl-1H-benzimidazol enantiomer A and enantiomer B,
5-(6-(4-(ethylsulfonyl)phenoxy-2-pyrazin-2-yl-1H-benzimidazol-5-yl)tetrahydrofuran-2-ol,
5-(tetrahydrofuran-2-yl)-6-(4-(ethylsulfonyl)phenoxy)-2-pyrazin-2-yl-1H-benzimidazole,
5-(tetrahydrofuran-2-yl)-6-((6-(ethylsulfonyl)pyridin-3-yl)oxy)-2-pyridin-2-yl-1H-benzimidazole,
5-(6-((6-(ethyl sulfonyl)pyridin-3-yl)oxy)-2-pyridin-2-yl-1H-benzimidazol-5-yl)tetrahydrofuran-2-ol,
5-(6-((6-(ethylsulfonyl)pyridin-3-yl)oxy)-2-pyridin-2-yl-1H-benzimidazol-5-yl)tetrahydrofuran-2-ol enantiomer A,
5-(6-((6-(ethylsulfonyl)pyridin-3-yl)oxy)-2-pyrazin-2-yl-1H-benzimidazol-5-yl)tetrahydrofuran-2-ol,
5-(tetrahydrofuran-2-yl)-6-((6-(ethylsulfonyl)pyridin-3-yl)oxy)-2-pyrazin-2-yl-1H-benzimidazole,
5-(tetrahydrofuran-2-yl)-6-(4-(methylsulfonyl)phenoxy)-2-pyridin-2-yl-1H-benzimidazole,
5-(tetrahydrofuran-2-yl)-6-(6-(5-methyl-(1,2,4)oxadiazol-3-yl)-pyridin-3-yl oxy)-2-pyridin-2-yl-1H-benzimidazole,
5-(tetrahydrofuran-2-yl)-6-((6-(methylsulfonyl)pyridin-3-yl)oxy)-2-pyridin-2-yl-1H-benzimidazole,
5-(4-methyltetrahydrofuran-2-yl)-6-(4-(methylsulfonyl)phenoxy)-2-pyridin-2-yl-1H-benzimidazole,
5-(6-(4-(methylsulfonyl)phenoxy)-2-pyridin-2-yl-1H-benzimidazol-5-yl)tetrahydrofuran-2-ol,
5-(6-(4-(ethylsulfonyl)phenoxy)-2-pyridin-2-yl-1H-benzimidazol-5-yl)dihydrofuran-2(3H)-one,
5-(6-(4-(ethylsulfonyl)phenoxy)-2-pyridin-2-yl-1H-benzimidazol-5-yl)dihydrofuran-2(3H)-one enantiomer A and enantiomer B,
5-(6-(4-(ethylsulfonyl)phenoxy)-2-pyrazin-2-yl-1H-benzimidazol-5-yl)dihydrofuran-2(3H)-one,
5-(6-((6-methylsulfonyl)pyridin-3-yl)oxy)-2-pyridin-2-yl-1H-benzimidazol-5-yl)dihydrofuran-2(3H)-one,
5-(6-(5-methyl-(1,2,4)oxadiazol-3-yl)-pyridin-3-yloxy)-2-pyridin-2-yl-1H-benzimidazol-5-yl)dihydrofuran-2(3H)-one,
5-(6-((6-(ethylsulfonyl)pyridin-3-yl)oxy)-2-pyridin-2-yl-1H-benzimidazol-5-yl)dihydrofuran-2(3H)-one,
5-(6-((6-(ethylsulfonyl)pyridin-3-yl)oxy)-2-pyridin-2-yl-1H-benzimidazol-5-yl)dihydrofuran-2(3H)-one enantiomer A and enantiomer B,
5-(64(6-ethylsulfonyl)pyridin-3-yl)oxy)-2-pyrazin-2-yl-1H-benzimidazol-5-yl)dihydrofuran-2(3H)-one,
5-(tetrahydro-2-thienyl)-6-(4-(ethylsulfonyl)phenoxy)-2-pyridin-2-yl-1H-benzimidazole and 5-(1,2-dithian-3-yl)-6-(4-(ethylsulfonyl)phenoxy)-2-pyridin-2-yl-1H-benzimidazole,
5-(1-oxidotetrahydro-2-thienyl)-6-(4-(ethylsulfonyl)phenoxy)-2-pyridin-2-yl-1H-benzimidazole and 5-(1,1-dioxidotetrahydro-2-thienyl)-6-(4-(ethylsulfonyl)phenoxy)-2-pyridin-2-yl-1H-benzimidazole,
5-(6-(4-(ethylsulfonyl)phenoxy)-2-pyridin-2-yl-1H-benzimidazol-5-yl)-3-methyl-1,3-oxazolidine-2,4-dione,
5-(6-((6-(ethylsulfonyl)pyridin-3-yl)oxy)-2-pyridin-2-yl-1H-benzimidazol-5-yl)-3-methyl-1,3-oxazolidine-2,4-dione, 5-(6-(4-(ethylsulfonyl)phenoxy)-2-pyridin-2-yl-1H-benzimidazol-5-yl)-1,3-oxazolidine-2,4-dione, 5-(6-(4-(ethylsulfonyl)phenoxy)-2-pyridin-2-yl-1H-benzimidazol-5-yl)-2,2-dimethyl-1,3-dioxolan-4-one, 4-(6-(4-(ethylsulfonyl)phenoxy)-2-pyridin-2-yl-1H-benzimidazol-5-yl)-1,3-dioxolan-2-one, 3-(6-(4-(ethylsulfonyl)phenoxy)-2-pyridin-2-yl-1H-benzimidazol-5-yl)dihydrofuran-2(3H)-one, 3-(6-((6-(ethylsulfonyl)pyridin-3-yl)oxy)-2-pyridin-2-yl-1H-benzimidazol-5-yl)dihydrofuran-2(3H)-one, 5-(tetrahydrofuran-3-yl)-6-((6-(ethylsulfonyl)pyridin-3-yl)oxy)-2-pyridin-2-yl-1H-benzimidazol, or 5-(6-((6-cyanopyridin-3-yl)oxy)-2-pyridin-2-yl-1H-benzimidazol-5-yl)dihydrofuran-2(3H)-one, or their pharmaceutically-acceptable salts.

Method for producing the compounds of the invention are described below.

Compounds (I-1) of the invention may be produced, for example, according to the following method:

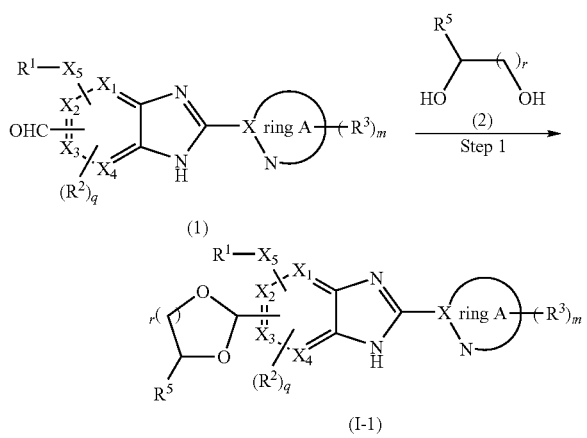

(In the formula, $R^5$ represents a hydrogen atom, or a lower alkyl group or the like optionally substituted with hydroxy, alkoxy or the like; r indicates 1 or 2; and the other symbols have the same meanings as above.)

(Step 1)

This step is a method for producing a compound (I-1) of the invention, by reacting a compound (1) and a compound (2) in the presence of an acid.

The acid to be used in this step includes, for example, p-toluenesulfonic acid, sulfuric acid, ytterbium triflate, camphorsulfonic acid or their hydrates.

The amount of the acid to be used may be generally from 0.01 to 10 equivalents relative to 1 equivalent of the compound (1), preferably from 0.1 to 3 equivalents.

The amount of the compound (2) to be used in this step may be generally from 0.1 to 100 equivalents relative to 1 equivalent of the compound (1), preferably from 1 to 5 equivalents.

The compound (2) includes, for example, ethylene glycol, 1,3-propanediol, 1,4-butanediol, 2-(hydroxymethyl)-1,3-propanediol, 2-(hydroxymethyl)-1,4-butanediol.

Not specifically defined or not used, the reaction solvent may be any one not interfering with the reaction, and includes, for example, toluene, chloroform, dimethylformamide. Of those, preferred are toluene and chloroform.

The reaction temperature may be generally from 0 to 150° C., preferably from room temperature to 120° C.

The reaction time may be generally from 5 minutes to 48 hours, preferably from 15 minutes to 12 hours.

The compound (I-1) thus obtained may be isolated and purified in any known manner for isolation and purification, for example, through concentration, concentration under reduced pressure, crystallization, solvent extraction, reprecipitation, chromatography.

Compounds (I-2) of the invention may be produced, for example, according to the following method:

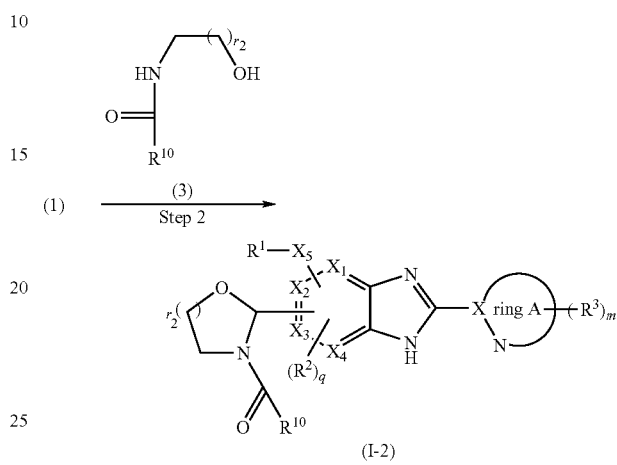

(n the formula, $R^{10}$ represents a lower alkyl group or the like optionally substituted with hydroxy, alkoxy or the like; $r_2$ indicates 1 or 2; and the other symbols have the same meanings as above.)

(Step 2)

This step is a method for producing a compound (I-2) of the invention by reaction the above compound (1) with a compound (3) in the presence of an acid.

The acid to be used in this step includes, for example, p-toluenesulfonic acid, sulfuric acid, ytterbium triflate, camphorsulfonic acid or their hydrates.

The amount of the acid to be used may be generally from 0.01 to 10 equivalents relative to 1 equivalent of the compound (1), preferably from 0.1 to 3 equivalents.

The amount of the compound (2) to be used in this step may be generally from 0.1 to 100 equivalents relative to 1 equivalent of the compound (1), preferably from 1 to 5 equivalents.

The compound (3) includes, for example, N-acetylethanolamine.

Not specifically defined or not used, the reaction solvent may be any one not interfering with the reaction, and includes, for example, toluene, chloroform, dimethylformamide. Of those, preferred are toluene and chloroform.

The reaction temperature may be generally from 0 to 150° C., preferably from room temperature to 120° C.

The reaction time may be generally from 5 minutes to 48 hours, preferably from 15 minutes to 12 hours.

The compound (I-2) thus obtained may be isolated and purified in any known manner for isolation and purification, for example, through concentration, concentration under reduced pressure, crystallization, solvent extraction, reprecipitation, chromatography.

Compounds (I-3) of the invention may be produced, for example, according to the following method:

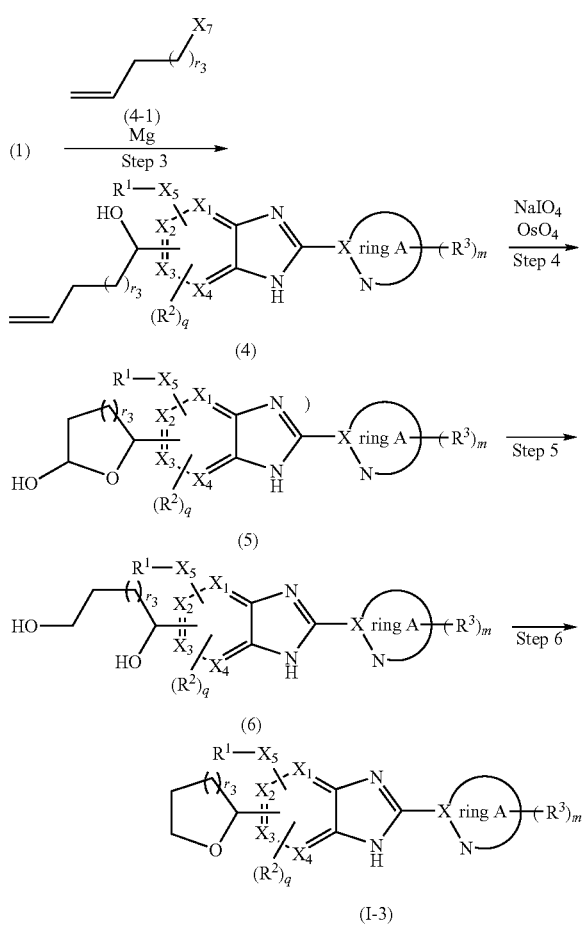

(In the formula, $r_3$ indicates 1 or 2; $X_7$ represents a halogen atom; and the other symbols have the same meanings as above.)

(Step 3)

This step is a method for producing a compound (4) by reacting the above compound (1) with a compound (4-1) and magnesium.

The compound (4-1) to be used in this step includes, for example, 4-bromo-1-butene, 5-bromo-1-pentene.

The amount of the compound (4-1) to be used may be generally from 0.5 to 20 equivalents relative to 1 equivalent of the compound (1).

The amount of magnesium to be used may be generally from 0.5 to 30 equivalents relative to 1 equivalent of the compound (1).

Not specifically defined, the reaction solvent may be any one not interfering with the reaction, and includes, for example, tetrahydrofuran, ether, dichloromethane, chloroform, toluene. Of those, preferred is tetrahydrofuran.

The reaction time may be generally from 5 minutes to 12 hours, preferably from 5 minutes to 1 hour.

The reaction temperature may be generally from −78 to 50° C., preferably from 0° C. to room temperature.

The compound (4) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 4)

This step is a method for producing a compound (5) of the invention by reacting the above compound (4) with sodium periodate and osmium tetroxide.

The amount of sodium periodate to be used in this step may be generally from 0.5 to 20 equivalents relative to 1 equivalent of the compound (4), preferably from 1 to 5 equivalents.

The amount of osmium tetroxide to be used in this step may be generally from 0.001 to 3 equivalents relative to 1 equivalent of the compound (1).

Not specifically defined, the reaction solvent may be any one not interfering with the reaction, and includes, for example, tetrahydrofuran, acetonitrile, acetone. Of those, preferred is tetrahydrofuran.

The reaction temperature may be generally from −78 to 50° C., preferably from 0° C. to room temperature.

The reaction time may be generally from 5 minutes to 24 hours, preferably from 30 minutes to 6 hours.

The compound (5) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 5)

This step is a method for producing a compound (6) by reducing the above compound (5).

The reducing agent to be used in this step includes, for example, $NaBH_4$, $Zn(BH_3CN)_2$, $NaB(OAc)_3H$, $NaBH_3CN$.

The amount of the reducing agent to be used may be generally from 0.5 to 10 equivalents relative to 1 equivalent of the compound (6).

Not specifically defined, the reaction solvent may be any one not interfering with the reaction, and includes, for example, methanol, ethanol, water, tetrahydrofuran. Of those, preferred is methanol.

The reaction temperature may be generally from 0 to 60° C., preferably from 0° C. to room temperature.

The reaction time may be generally from 30 minutes to 24 hours, preferably from 1 to 12 hours.

The compound (6) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 6)

This step is a method for producing a compound (I-3) of the invention by cyclizing the above compound (6) in the presence of an acid.

The acid to be used in this step includes, for example, p-toluenesulfonic acid, sulfuric acid, ytterbium triflate, camphorsulfonic acid or their hydrates.

The amount of the acid to be used may be generally from 0.01 to 10 equivalents relative to 1 equivalent of the compound (6), preferably from 0.1 to 3 equivalents.

Not specifically defined or not used, the reaction solvent may be any one not interfering with the reaction, and includes, for example, toluene, chloroform, dimethylformamide. Of those, preferred are toluene and chloroform.

The reaction time may be generally from 5 minutes to 48 hours, preferably from 15 minutes to 12 hours.

The reaction temperature may be generally from 0 to 180° C., preferably from room temperature to 120° C.

The compound (I-3) thus obtained may be isolated and purified in any known manner for isolation and purification, for example, through concentration, concentration under reduced pressure, crystallization, solvent extraction, reprecipitation, chromatography.

This step may also be attained by introducing one leaving group into the hydroxyl group and then adding a base to the reaction liquid for cyclization.

The reagent to be used for introducing the leaving group includes methanesulfonyl chloride, p-toluenesulfonyl chloride, sulfonyl chloride; and preferred is methanesulfonyl chloride.

The amount of the reagent to be used may be generally from 0.5 to 20 equivalents relative to 1 equivalent of the compound (6), preferably from 0.5 to 10 equivalents.

A base may be used in the reaction, including, for example, triethylamine, pyridine, N,N-dimethylaminopyridine. Preferred is triethylamine.

The amount of the reagent to be used may be generally from 0.5 to 20 equivalents relative to 1 equivalent of the compound (6), preferably from 0.5 to 10 equivalents.

Not specifically defined, the reaction solvent may be any one not interfering with the reaction, and includes, for example, tetrahydrofuran, ethyl acetate, dioxane, chloroform. Of those, preferred is ethyl acetate.

The reaction time may be generally from 5 minutes to 48 hours, preferably from 15 minutes to 12 hours.

The reaction temperature may be generally from −20 to 100° C., preferably from 0 to 40° C.

The base to be used for cyclization includes N,N-dimethylaminopyridine, 1,8-diazabicyclo[5.4.0]undec-7-ene, sodium hydride, potassium carbonate. For the cyclization, the base may be directly added to the reaction solution into which a leaving group has been introduced, but is preferably added to a solution of a post-treated crude product.

The compound (I-3) thus obtained may be isolated and purified in any known manner for isolation and purification, for example, through concentration, concentration under reduced pressure, crystallization, solvent extraction, reprecipitation, chromatography.

Compounds (I-4) of the invention may be produced, for example, according to the following method:

(8)

(9-1)

(9-2)

(I-4)

(In the formula, the symbols have the same meanings as above.)

(Step 7)

This step is a method for producing a compound (9-1) by reacting a compound (8) with 2-methylallylmagnesium chloride.

The amount of the compound 2-methylallylmagnesium chloride to be used in this step may be generally from 0.5 to 10 equivalents relative to 1 equivalent of the compound (8), preferably from 1 to 5 equivalents.

Not specifically defined, the reaction solvent may be any one not interfering with the reaction, and includes, for example, tetrahydrofuran, ether, dichloromethane, chloroform, toluene. Of those, preferred is tetrahydrofuran.

The reaction time may be generally from 1 minute to 48 hours, preferably from 5 minutes to 1 hour.

The reaction temperature may be generally from −78 to 50° C., preferably from 0° C. to room temperature.

The compound (9-1) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 8)

This step is a method for producing a compound (I-4) of the invention using the compound (9-1), which comprises a step of hydroboration (step 8-1) and a subsequent step (step 8-2) for cyclization.

(Step 8-1)

The borane for hydroboration in this step includes borane-tetrahydro complex, borane-dimethylsulfide complex, 9-BBN; and preferred is borane-tetrahydro complex.

The amount of the borane to be used may be generally from 0.5 to 50 equivalents relative to 1 equivalent of the compound (9-1), preferably from 2 to 10 equivalents.

Not specifically defined, the reaction solvent may be any one not interfering with the reaction, and includes, for example, tetrahydrofuran, ether, dichloromethane, chloroform, toluene. Of those, preferred is tetrahydrofuran.

The reaction time may be generally from 1 minute to 48 hours, preferably from 30 minutes to 3 hours.

The reaction temperature may be generally from −78 to 50° C., preferably from 0° C. to room temperature.

After the hydroboration, the reaction liquid is processed with sodium hydroxide or aqueous hydrogen peroxide.

The compound (9-2) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 8-2)

This step is a method for producing a compound (I-4) of the invention by cyclizing the compound (9-2) obtained in the previous step 8-1, in the presence of an acid.

The cyclization may be attained in the same manner as in the above step 6, or according to the method, or according to a combination thereof with an ordinary method The compound (I-4) thus obtained may be isolated and purified in any known manner for isolation and purification, for example, through concentration, concentration under reduced pressure, crystallization, solvent extraction, reprecipitation, chromatography.

Compounds (I-5) of the invention may be produced, for example, according to the following method:

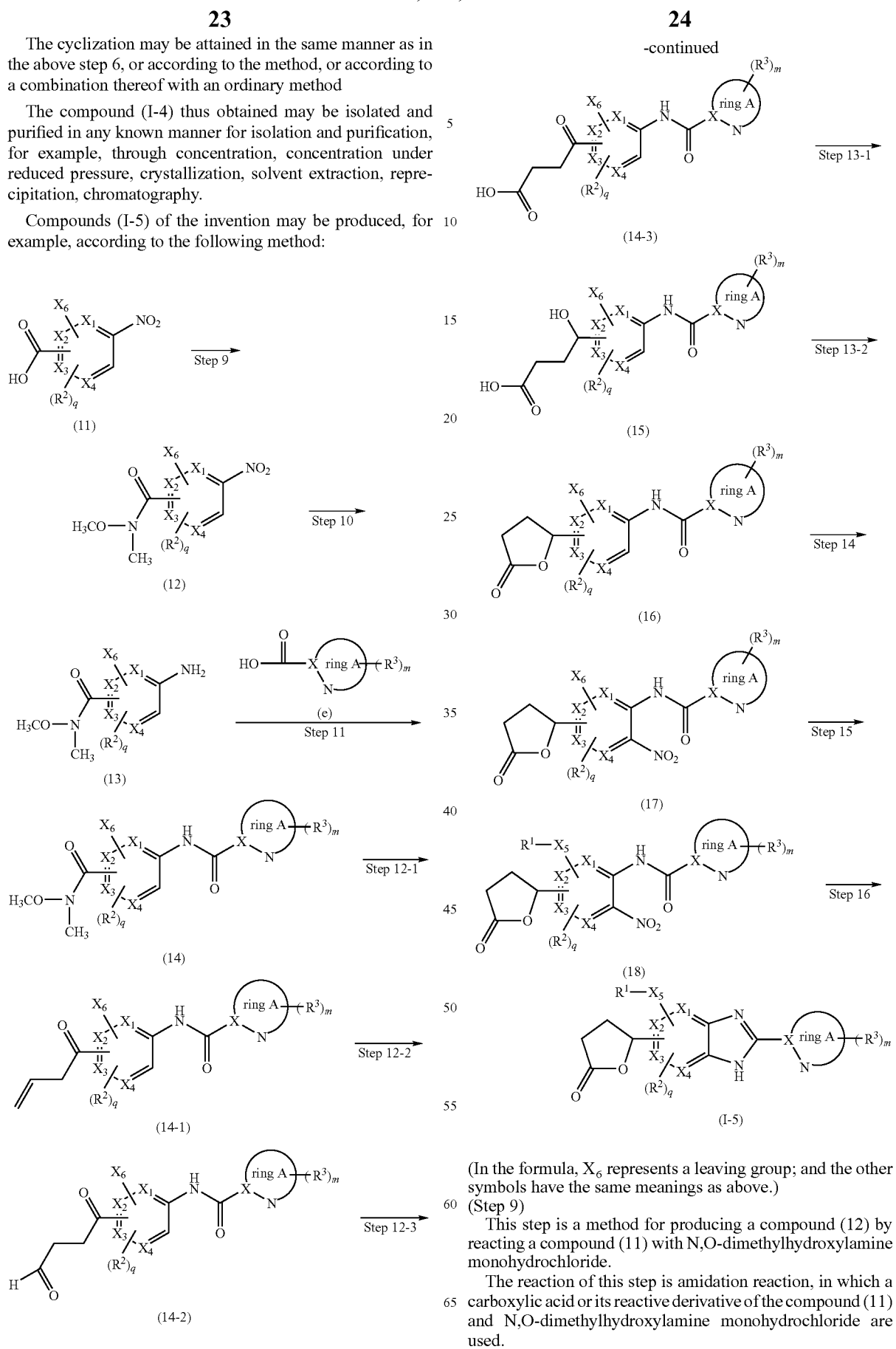

(In the formula, $X_6$ represents a leaving group; and the other symbols have the same meanings as above.)

(Step 9)

This step is a method for producing a compound (12) by reacting a compound (11) with N,O-dimethylhydroxylamine monohydrochloride.

The reaction of this step is amidation reaction, in which a carboxylic acid or its reactive derivative of the compound (11) and N,O-dimethylhydroxylamine monohydrochloride are used.

The compound (11) or its reactive derivative to be used may be in an amount of generally from 0.1 to 100 equivalents, preferably from 0.1 to 3 equivalents.

The "reactive derivative" of the compound (11) includes, for example, mixed acid anhydrides, active esters, active amides; and these may be obtained, for example, according to the method described in WO98/05641.

In the above reaction, when a carboxylic acid of the compound (11) is used, it is desirable that the reaction is attained in the presence of a condensing agent, for example, carbonyldiimidazole, N,N'-dicyclohexylcarbodiimide, 1-ethyl-3-(3-dimethylaminopropyl)carbodiimide, diphenylphosphorylazide, dipyridyl disulfide-triphenyl phosphine, preferably carbonyldiimidazole.

The amount of the condensing agent to be used is not strictly limited, but in general, it may be from 0.1 to 100 equivalents relative to the compound (11), preferably from 0.1 to 10 equivalents.

The reaction is generally attained in an inert solvent. The insert solvent includes, for example, tetrahydrofuran, N,N-dimethylformamide, 1,4-dioxane, benzene, toluene, methylene chloride, chloroform, carbon tetrachloride, 1,2-dichloroethane, pyridine, or mixtures of such solvents.

The reaction temperature may be generally from 0° C. to the reflux temperature of the reaction solvent, preferably from room temperature to the reflux temperature of the reaction solvent.

The reaction time may be generally from 0.1 hours to 72 hours, preferably from 0.5 hours to 24 hours.

The reaction may be attained in the presence of a base and a condensation promoter for smoothly promoting the reaction.

The base includes 4-dimethylaminopyridine, triethylamine.

The amount of the base to be used may be generally from 0.1 to 100 equivalents relative to 1 mol of the carboxylic acid or its reactive derivative of the compound (11), preferably from 0.1 to 1 equivalent.

The condensation promoter includes N-hydroxybenzotriazole hydrate, N-hydroxysuccinimide.

The amount of the condensation promoter to be used may be generally from 1 to 100 equivalents relative to 1 mol of the carboxylic acid or its reactive derivative of the compound (11), preferably from 1 to 5 equivalents.

The compound (12) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 10)

This step is a method for producing a compound (13) by reducing the nitro group that the above compound (12) has.

The reducing agent to be used in this step includes tin chloride, iron(II), Raney nickel, palladium, palladium hydroxide.

The amount of the reducing agent to be used may be generally from 0.01 to 30 equivalents relative to 1 equivalent of the compound (12), preferably from 0.1 to 10 equivalents.

Not specifically defined, the reaction solvent may be any one not interfering with the reaction, and includes, for example, methanol, ethanol, N-methylpyrrolidinone, dimethylformamide, tetrahydrofuran, acetic acid. Of those, preferred are N-methylpyrrolidinone, methanol. However, when iron (II) is used, preferred is acetic acid.

The reaction temperature may be generally from 0 to 150° C., preferably from room temperature to 100° C.

The reaction time may be generally from 1 minute to 24 hours, preferably from 5 minutes to 12 hours.

The compound (13) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 11)

This step is a method for producing a compound (14) by reacting the above compound (13) with a compound (e).

This reaction is amidation, in which a carboxylic acid or its reactive derivative of the compound (e) is used.

The compound (e) to be used includes, for example, pyridine-2-carboxylic acid, pyrazine-2-carboxylic acid, pyrimidine-4-carboxylic acid, pyrimidine-2-carboxylic acid, thiazole-2-carboxylic acid, isoxazole-3-carboxylic acid, 5-methyl-isoxazole-3-carboxylic acid, 1-methyl-1H-imidazole-4-carboxylic acid, imidazole-2-carboxylic acid, 1-methyl-1H-imidazole-2-carboxylic acid, imidazole-1-carboxylic acid, [1,2,4]triazole-1-carboxylic acid, [1,2,4]triazole-3-carboxylic acid, [1,2,3]triazole-4-carboxylic acid, 3-methyl-[1,2,4]thiadiazole-5-carboxylic acid, [1,2,5]thiadiazole-3-carboxylic acid, [1,2,3]oxadiazole-3-carboxylic acid, pyrazole-3-carboxylic acid.

The amount of the compound (e) or its reactive derivative to be used may be generally from 0.1 to 100 equivalents relative to 1 equivalent of the compound (13), preferably from 0.1 to 20 equivalents, more preferably from 0.1 to 3 equivalents.

The reactive derivative of the compound (e) includes, for example, mixed acid anhydrides, active esters, active amides; and these may be obtained according to the method described in WO98/05641.

In the above reaction, when a carboxylic acid of the compound (e) is used, for example, it is desirable that the reaction is attained in the presence of a condensing agent such as carbonyldiimidazole, N,N'-dicyclohexylcarbodiimide, 1-ethyl-3-(3-dimethylaminopropyl)carbodiimide, diphenylphosphorylazide, dipyridyl disulfide-triphenyl phosphine, preferably carbonyldiimidazole.

The amount of the condensing agent to be used is not strictly limited, but in general, it may be from 0.1 to 100 equivalents relative to the compound (e), more preferably from 0.1 to 10 equivalents.

The reaction is generally attained in an inert solvent, and the inert solvent includes, for example, tetrahydrofuran, N,N-dimethylformamide, 1,4-dioxane, benzene, toluene, methylene chloride, chloroform, carbon tetrachloride, 1,2-dichloroethane, pyridine, or mixtures of such solvents.

The reaction temperature may be generally from 0° C. to the reflux temperature of the reaction solvent, preferably from room temperature to the reflux temperature of the reaction solvent.

The reaction time may be generally from 0.1 hours to 72 hours, preferably from 0.5 hours to 24 hours.

The reaction may be attained in the presence of a base and a condensation promoter for smoothly promoting the reaction.

The base includes 4-dimethylaminopyridine, triethylamine.

The amount of the base to be used may be generally from 0.1 to 100 equivalents relative to 1 mol of the carboxylic acid or its reactive derivative of the compound (e), preferably from 0.1 to 1 equivalent.

The condensation promoter includes N-hydroxybenzotriazole hydrate, N-hydroxysuccinimide.

The amount of the condensation promoter to be used may be generally from 1 to 100 equivalents relative to 1 mol of the carboxylic acid or its reactive derivative of the compound (e), preferably from 1 to 5 equivalents.

In the above reaction, in case where an amino group or an imino group not participating in the reaction exists in the reactant substance, then it is desirable that the amino group or imino group is protected with a protective group for amino group or imino group, then the reaction is attained, and after the reaction, the protective group is removed.

The compound (14) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 12-1)

This step is a method for producing a compound (14-1) by reacting the above compound (14) with 3-butenylmagnesium bromide.

The amount of the compound 3-butenylmagnesium bromide to be used in this step may be generally from 0.5 to 10 equivalents relative to 1 equivalent of the compound (14), preferably from 1 to 5 equivalents.

Not specifically defined, the reaction solvent may be any one not interfering with the reaction, and includes, for example, tetrahydrofuran, ether, dichloromethane, chloroform, toluene. Of those, preferred is tetrahydrofuran.

The reaction time may be generally from 1 minute to 48 hours, preferably from 5 minutes to 1 hour.

The reaction temperature may be generally from −78 to 50° C., preferably from 0° C. to room temperature.

The compound (14-1) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 12-2)

This step is a method for producing a compound (14-2) by reacting the olefin compound obtained in the previous step (12-1) with sodium periodate and osmium tetroxide.

The amount of sodium periodate to be used in this step may be generally from 0.5 to 20 equivalents relative to 1 equivalent of the olefin compound, preferably from 1 to 5 equivalents.

The amount of osmium tetroxide to be used in this step may be generally from 0.01 to 3 equivalents relative to 1 equivalent of the olefin compound.

Not specifically defined, the reaction solvent may be any one not interfering with the reaction, and includes, for example, tetrahydrofuran, acetonitrile, acetone. Of those, preferred is tetrahydrofuran.

The reaction temperature may be generally from −78 to 50° C., preferably from 0° C. to room temperature.

The reaction time may be generally from 5 minutes to 24 hours, preferably from 30 minutes to 6 hours.

The compound (14-2) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 12-3)

This step is a method for producing a compound (14-3) by oxidizing the compound (14-2) obtained in the previous step (12-2).

The amount of sodium chlorite to be used in this step may be generally from 0.5 to 20 equivalents relative to 1 equivalent of the compound (14-2), preferably from 1 to 5 equivalents.

The amount of 2-methyl-2-butene to be used in this step may be generally from 0.5 to 10 equivalents relative to 1 equivalent of the compound (14-2).

The amount of monosodium-dihydrogen phosphate to be used in this step may be generally from 0.5 to 10 equivalents relative to 1 equivalent of the compound (14-2), preferably from 1 to 3 equivalents.

Not specifically defined, the reaction solvent may be any one not interfering with the reaction, and includes, for example, tetrahydrofuran, acetonitrile, acetone, t-butanol, water, and they may be used as combined.

The reaction temperature may be generally from −78 to 50° C., preferably from 0° C. to room temperature.

The reaction time may be generally from 5 minutes to 24 hours, preferably from 1 hour to 12 hours.

The compound (14-3) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 13-1)

This step is a method for reducing the ketone group of the above compound (14-3) to convert into a compound (15).

For the ketone reduction, preferred is a method of using a reducing agent such as sodium borohydride, lithium aluminium hydride, lithium borohydride, diisobutylaluminium hydride. Preferred is sodium borohydride.

The amount of the reducing agent to be used in this step may be generally from 0.1 to 10 equivalents relative to 1 equivalent of the compound (14-3), preferably from 1 to 5 equivalents.

Not specifically defined, the reaction solvent may be any one not interfering with the reaction, and includes, for example, methanol, ethanol, water. Preferred is methanol.

The reaction temperature may be generally from −78 to 50° C., preferably from 0° C. to room temperature.

The reaction time may be generally from 5 minutes to 24 hours, preferably from 5 minutes to 1 hour.

The compound (15) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 13-2)

This step is a method of cyclizing the compound (15) obtained in the previous step (13-1) to convert into a compound (16).

The reaction in this step is attained with an acid catalyst.

The acid catalyst to be used in this step includes, for example, p-toluenesulfonic acid, sulfuric acid, ytterbium triflate, camphorsulfonic acid, or their hydrates.

The amount of the acid to be used may be generally from 0.01 to 10 equivalents relative to 1 equivalent of the compound (15), preferably from 0.1 to 3 equivalents.

Not specifically defined or not used, the reaction solvent may be any one not interfering with the reaction, and includes, for example, toluene, chloroform, dimethylformamide. Of those, preferred are toluene and chloroform.

The reaction time may be generally from 5 minutes to 48 hours, preferably from 15 minutes to 12 hours.

The reaction temperature may be generally from 0 to 180° C., preferably from room temperature to 120° C.

The compound (16) thus obtained may be isolated and purified in any known manner for isolation and purification, for example, through concentration, concentration under reduced pressure, crystallization, solvent extraction, reprecipitation, chromatography.
(Step 14)

This step is a method for producing a compound (17) by reacting the above compound (16) with fuming nitric acid.

The amount of fuming nitric acid to be used in this step may be generally from 0.5 to 50 equivalents relative to 1 equivalent of the compound (16), preferably from 1 to 10 equivalents.

Preferably, a reaction solvent is not used; however, for example, chloroform, trifluoroacetic acid, sulfuric acid, hydrochloric acid may be used.

The reaction time may be generally from 1 minute to 24 hours, preferably from 5 minutes to 3 hours.

The reaction temperature may be generally from 0 to 100° C., preferably from room temperature to 50° C.

The compound (17) thus obtained may be subjected to the next step, after isolated and purified in any known manner for isolation and purification, for example, through concentration, concentration under reduced pressure, crystallization, solvent extraction, reprecipitation, chromatography, or not after isolated and purified.
(Step 15)

This step is a method for producing a compound (18) by reacting the above compound (17) with Ar—Z—$X_8$ in the presence of a base.

The amount of the base to be used in this step may be generally from 0.5 to 20 equivalents relative to 1 equivalent of the compound (17), preferably from 1 to 5 equivalents.

The base includes, for example, potassium carbonate, sodium carbonate, cesium carbonate, triethylamine, cesium fluoride.

Not specifically defined, the reaction solvent may be any one not interfering with the reaction, and includes, for example, N-methylpyrrolidinone, dimethylformamide, tetrahydrofuran, acetonitrile. Of those, preferred are N-methylpyrrolidinone, dimethylformamide.

The reaction time may be generally from 1 minute to 12 hours, preferably from 5 minutes to 3 hours.

The reaction temperature may be generally from room temperature to 150° C., preferably from room temperature to 100° C.

The compound (18) thus obtained may be subjected to the next step, after isolated and purified in any known manner for isolation and purification, for example, through concentration, concentration under reduced pressure, crystallization, solvent extraction, reprecipitation, chromatography, or not after isolated and purified.
(Step 16)

This step is a method for producing a compound (I-6) of the invention by reducing the above compound (18) and further cyclizing it.

The reducing agent to be used in this step includes, for example, tin(II) chloride, iron(II), Raney nickel, palladium hydroxide.

The amount of the reducing agent to be used may be generally from 0.01 to 20 equivalents relative to 1 equivalent of the compound (18), preferably from 0.1 to 10 equivalents.

Not specifically defined, the reaction solvent may be any one not interfering with the reaction, and includes, for example, methanol, ethanol, N-methylpyrrolidinone, dimethylformamide, tetrahydrofuran, acetic acid. Of those, preferred is methanol. However, when iron(II) is used, acetic acid is preferred.

The reaction temperature may be generally from 0 to 150° C., preferably from room temperature to 100° C.

The reaction time may be generally from 1 minute to 24 hours, preferably from 5 minutes to 12 hours.

The compound (I-6) thus obtained may be isolated and purified in any known manner for isolation and purification, for example, through concentration, concentration under reduced pressure, crystallization, solvent extraction, reprecipitation, chromatography.

Compounds (I-6) of the invention may be produced, for example, according to the following method.

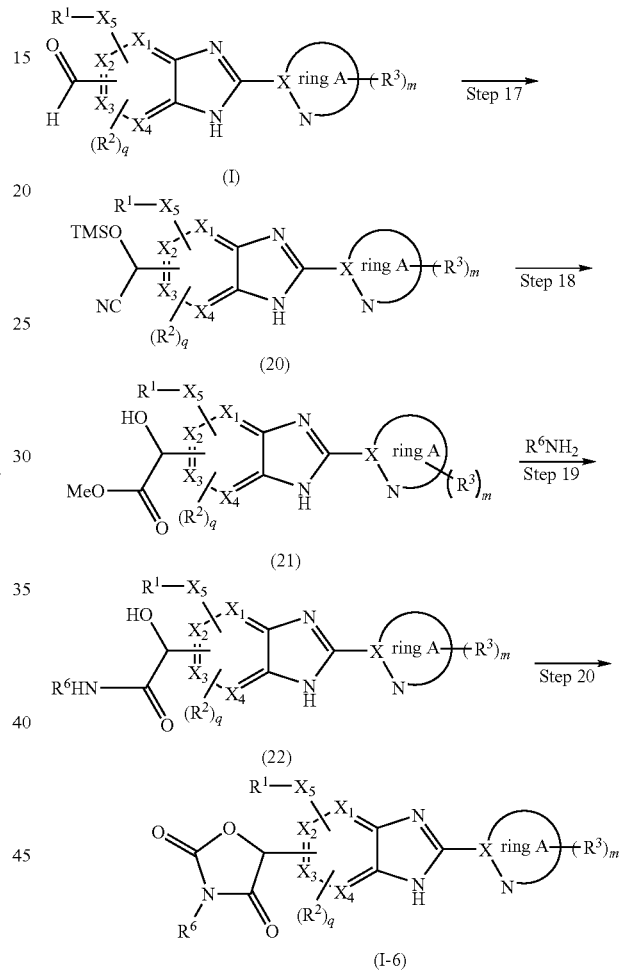

(In the formula, $R^6$ represents a hydrogen atom or $C_{1-6}$ alkyl; and the other symbols have the same meanings as above.)
(Step 17)

his step is a method for producing a compound (20) by reacting the above compound (1) with trimethylsilylnitrile in the presence of zinc iodide.

The amount of zinc iodide to be used in this step may be generally from 0.01 to 10 equivalents relative to 1 equivalent of the compound (1), preferably from 0.1 to 1 equivalent.

The amount of trimethylsilylnitrile to be used in this step may be generally from 1 to 100 equivalents relative to 1 equivalent of the compound (1), preferably from 1 to 10 equivalents.

Not specifically defined or not used, the reaction solvent may be any one not interfering with the reaction, and includes, for example, chloroform, dimethylformamide, toluene.

The reaction temperature may be generally from 0 to 100° C., preferably from 0° C. to room temperature.

The reaction time may be generally from 10 minutes to 12 hours, preferably from 1 to 12 hours.

The compound (20) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 18)

This step is a method for producing a compound (21) by reacting the above compound (20) with 10% hydrochloric acid-methanol.

10% hydrochloric acid-methanol used in this step serves as a solvent.

The reaction temperature may be generally from 0 to 80° C., preferably from 0 to 50° C.

The reaction time may be generally from 10 minutes to 3 hours, preferably from 10 minutes to 1 hour.

The compound (21) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 19)

This step is a method for producing a compound (22) by reacting the above compound (21) with a compound $R^6NH_2$ in the presence of a base.

The compound $R^6NH_2$ is, for example, methylamine.

The amount of the compound $R^6NH_2$ to be used in this step may be generally from 0.5 to 30 equivalents relative to 1 equivalent of the compound (21), preferably from 1 to 10 equivalents.

Not specifically defined, the reaction solvent may be any one not interfering with the reaction, and includes, for example, methanol, tetrahydrofuran, chloroform. Of those, preferred is methanol.

The reaction time may be generally from 10 minutes to 12 hours, preferably from 10 minutes to 3 hours.

The reaction temperature may be generally from 0 to 60° C., preferably from room temperature to 50° C.

The compound (22) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 20)

This step is a method for producing a compound (I-6) of the invention by reacting the above compound (22) with carbonylimidazole in the presence of a base and further cyclizing it with a strong base added thereto.

The base to be used in reacting the above compound (22) with carbonylimidazole includes triethylamine, N,N-dimethylaminopyridine, 1,8-diazabicyclo[5.4.0]undec-7-ene, potassium carbonate.

The amount of the base may be generally from 0.5 to 20 equivalents relative to 1 equivalent of the compound (22), preferably from 1 to 10 equivalents.

Not specifically defined, the reaction solvent may be any one not interfering with the reaction, and includes, for example, dimethylformamide, chloroform, tetrahydrofuran. Of those, preferred is dimethylformamide.

The reaction time may be generally from 10 minutes to 24 hours, preferably from 1 to 5 hours.

The reaction temperature may be generally from 0 to 100° C., preferably from 0 to 60° C.

The strong base to be used after the reaction of the compound (22) with carbonylimidazole is, for example, potassium tert-butoxide.

The amount of the strong base may be generally from 1 to 20 equivalents relative to 1 equivalent of the compound (22), preferably from 1 to 10 equivalents.

Preferably, these bases are added directly to the reaction mixture.

The reaction temperature may be generally from 0 to 120° C., preferably from room temperature to 100° C.

The reaction time may be generally from 10 minutes to 24 hours, preferably from 10 minutes to 6 hours.

The compound (I-6) thus obtained may be isolated and purified in any known manner for isolation and purification, for example, through concentration, concentration under reduced pressure, crystallization, solvent extraction, reprecipitation, chromatography.

Compounds (I-7) of the invention may be produced, for example, according to the following method:

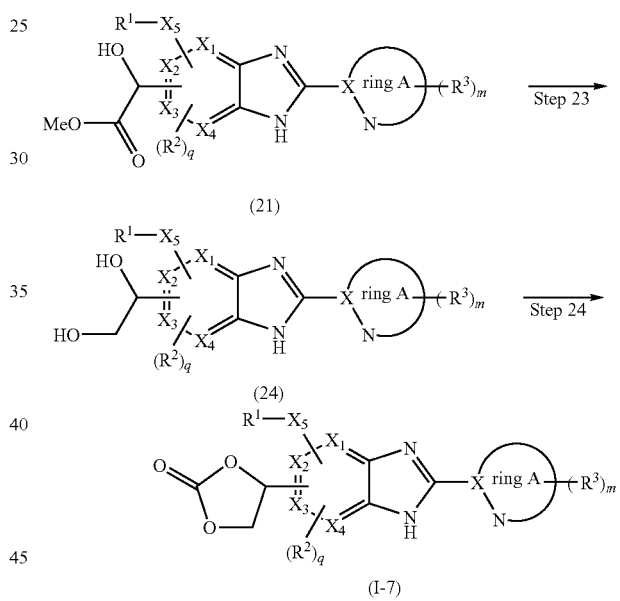

(In the formula, the symbols have the same meanings as above.)

(Step 23)

This step is a method for producing a compound (24) by reducing the above compound (21).

The reducing agent to be used in this step includes, for example, lithiumaluminium hydride or diisobutylaluminium hydride.

The amount of the reducing agent to be used may be generally from 0.5 to 10 equivalents relative to 1 equivalent of the compound (21), preferably from 1 to 5 equivalents.

Not specifically defined, the reaction solvent may be any one not interfering with the reaction, and includes, for example, toluene, chloroform, tetrahydrofuran. Of those, preferred is tetrahydrofuran.

The reaction temperature may be generally from −20 to 80° C., preferably from 0 to 30° C.

The reaction time may be generally from 1 minute to 6 hours, preferably from 5 minutes to 1 hour.

The compound (24) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 24)

This step is a method for producing a compound (I-7) of the invention by reacting the above compound (24) with carbonyldiimidazole.

The amount of carbonyldiimidazole to be used in this step may be generally from 0.5 to 10 equivalents relative to 1 equivalent of the compound (24), preferably from 1 to 5 equivalents.

Not specifically defined, the reaction solvent may be any one not interfering with the reaction, and includes, for example, dimethylformamide, tetrahydrofuran, chloroform. Of those, preferred is dimethylformamide.

The reaction temperature may be generally from 0 to 150° C., preferably from room temperature to 100° C.

The reaction time may be generally from 0.5 to 24 hours, preferably from 1 to 12 hours.

The compound (I-7) thus obtained may be isolated and purified in any known manner for isolation and purification, for example, through concentration, concentration under reduced pressure, crystallization, solvent extraction, reprecipitation, chromatography.

Compounds (I-8) of the invention may be produced, for example, according to the following method:

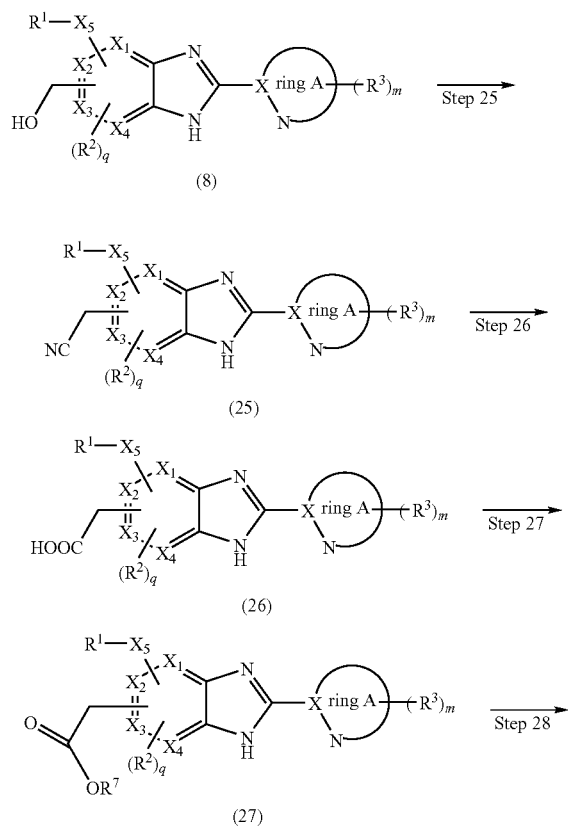

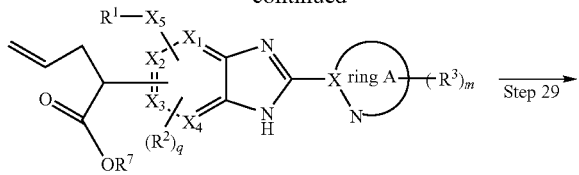

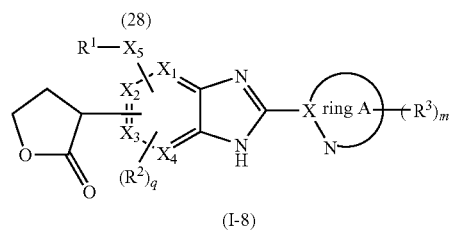

(In the formula, $R^7$ represents $C_{1-6}$ alkyl, and the other symbols have the same meanings as above.)

(Step 25)

his step is a method for producing a compound (25) by introducing a leaving group into the above compound (8) and then reacting the leaving group-introduced compound with sodium cyanide.

The reaction in this step may be attained by reacting the compound (8) with methanesulfonyl chloride in the presence of a base thereby converting the hydroxyl group into a leaving group, and then reacting the leaving group-having compound with sodium cyanide.

The base to be used in this step includes, for example, triethylamine, pyridine, N,N-dimethylaminopyridine.

The amount of the base may be generally from 0.5 to 50 equivalents relative to 1 equivalent of the compound (25), preferably from 1 to 10 equivalents.

The amount of sodium cyanide to be used in this step may be generally from 0.5 to 10 equivalents relative to 1 equivalent of the compound (25), preferably from 1 to 5 equivalents.

Not specifically defined, the reaction solvent may be any one not interfering with the reaction, and includes, for example, acetonitrile, acetone, dimethylformamide, dimethyl sulfide. Of those preferred is dimethylformamide.

The reaction temperature may be generally from 0 to 100° C., preferably from 0 to 50° C.

The reaction time may be generally from 5 minutes to 12 hours, preferably from 5 minutes to 6 hours.

The compound (25) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 26)

This step is a method for producing a compound (26) by hydrolyzing the nitrile group that the compound (25) obtained in the previous step 25 has.

This step is attained in the presence of sodium hydroxide.

The amount of 5 N sodium hydroxide to be used may be generally from 1 to 100 equivalents relative to 1 equivalent of the compound (25), preferably from 1 to 10 equivalents.

Not specifically defined, the reaction solvent may be any one not interfering with the reaction, and includes, for example, methanol, tetrahydrofuran, water, or their mixed solvents. Preferred is a mixed solvent of methanol or tetrahydrofuran, and water.

The reaction temperature may be generally from 0 to 150° C., preferably from room temperature to 100° C.

The reaction time may be generally from 1 to 48 hours, preferably from 1 to 24 hours.

The compound (26) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 27)

This step is a method for converting the carboxyl group of the compound (26) obtained in the previous step 26 into a $C_{1-6}$ alkyl ester (27) such as methyl ester.

In case where it is converted into a methyl ester, for example, the compound (26) may be reacted with trimethylsilyldiazomethane to obtain a methyl ester compound.

The amount of trimethylsilyldiazomethane to be used may be generally from 0.5 to 20 equivalents relative to 1 equivalent of the compound (26), preferably from 1 to 10 equivalents.

Not specifically defined, the reaction solvent may be any one not interfering with the reaction, and includes, for example, methanol, tetrahydrofuran, chloroform. Of those, preferred is methanol.

The reaction temperature may be generally from 0 to 100° C., preferably from 0° C. to room temperature.

The reaction time may be generally from 5 minutes to 24 hours, preferably from 5 minutes to 2 hours.

In case where the carboxyl group that the compound (26) has is converted into a $C_{1-6}$ alkyl ester, the $C_{1-6}$ alkyl ester may be produced in a known method, or according to the method, or according to a combination thereof with an ordinary method.

The compound (26) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 28)

This step is a method for producing a compound (28) by reacting the compound (27) obtained in the previous step 27 with allyl bromide in the presence of a base.

The base to be used in this step includes, for example, lithium diisopropylamide, sodium hydride, potassium t-butoxide.

The amount of base to be used may be generally from 0.5 to 10 equivalents relative to 1 equivalent of the compound (27), preferably from 1 to 5 equivalents.

The amount of ally bromide to be used in this step may be generally from 0.5 to 10 equivalents relative to 1 equivalent of the compound (27), preferably from 1 to 5 equivalents.

Not specifically defined, the reaction solvent may be any one not interfering with the reaction, and includes, for example, dimethylformamide, tetrahydrofuran. Of those, preferred is dimethylformamide.

The reaction temperature may be generally from −78 to 60° C., preferably from −20° C. to room temperature.

The reaction time may be generally from 5 minutes to 12 hours, preferably from 30 minutes to 6 hours.

The compound (28) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 29)

This step may be attained in the same manner as in the previous step 12-2 and 13-1, or according to the method, or according to a combination thereof with an ordinary method.

The compound (I-8) thus obtained may be isolated and purified in any known manner for isolation and purification, for example, through concentration, concentration under reduced pressure, crystallization, solvent extraction, reprecipitation, chromatography.

Compounds (I-9):

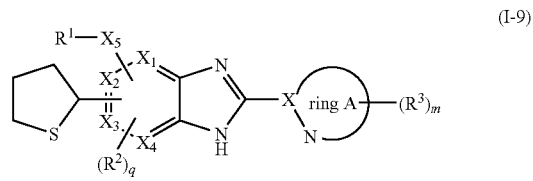

(I-9)

or compounds (I-10):

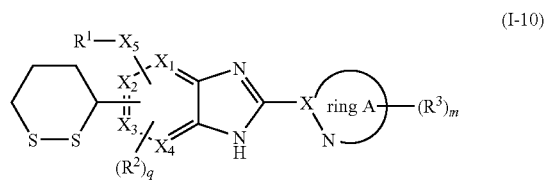

(I-10)

of the invention may be produced, for example, according to the following method:

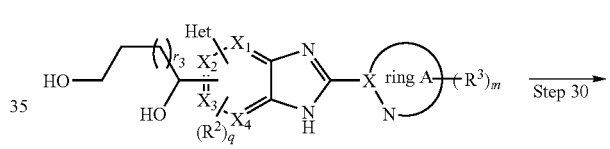

(6)

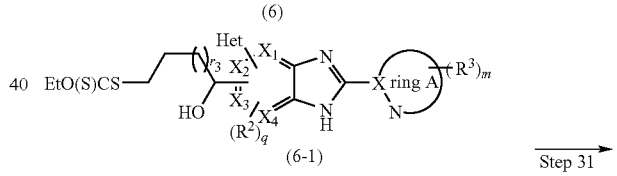

(6-1)

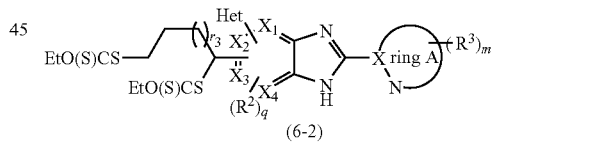

(6-2)

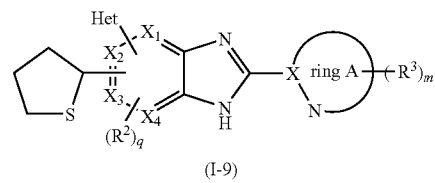

(I-9)

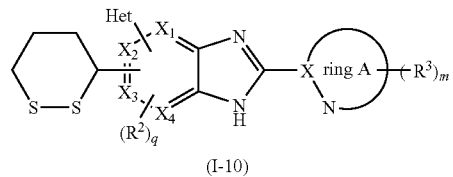

(I-10)

(In the formula, the symbols have the same meanings as above.)

(Step 30)

This step is a method for producing a compound (6-1) or (6-2) by introducing a leaving group into the above compound (6) and then reacting it with potassium O-ethyldithiocarbonate.

The reaction in this step may be attained by reacting the compound (6) with methanesulfonyl chloride in the presence of a base to thereby convert the hydroxyl group into a leaving group, and the reacting the leaving group-having compound with potassium O-ethyldithiocarbonate.

The base to be used in this step includes, for example, triethylamine, pyridine, N,N-dimethylaminopyridine.

The amount of the base may be generally from 0.5 to 50 equivalents relative to 1 equivalent of the compound (6), preferably from 1 to 10 equivalents.

The amount of potassium O-ethyldithiocarbonate to be used in this step may be generally from 0.5 to 10 equivalents relative to 1 equivalent of the compound (6), preferably from 1 to 5 equivalents.

Not specifically defined, the reaction solvent may be any one not interfering with the reaction, and includes, for example, acetonitrile, acetone, dimethylformamide, dimethyl sulfide. Of those, preferred is acetone.

The reaction temperature may be generally from 0 to 100° C., preferably from 0 to 80° C.

The reaction time may be generally from 5 minutes to 12 hours, preferably from 5 minutes to 6 hours.

The compound (6-1) or (6-2) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 31)

This step is a method for producing a compound (I-9) or (I-10) by converting the above compound (6-1) into a monothiol compound or (6-2) into a dithiol compound under a basic condition, and then cyclizing it in the presence of an acid catalyst.

The base to be used in this step includes, for example, sodium hydroxide, sodium methoxide, potassium carbonate.

The amount of the base may be generally from 0.5 to 50 equivalents relative to 1 equivalent of the compound (6-1) or (6-2), preferably from 1 to 10 equivalents.

Not specifically defined, the reaction solvent may be any one not interfering with the reaction, and includes, for example, methanol, water.

The reaction temperature may be generally from 0 to 100° C., preferably from 0 to 80° C.

The reaction time may be generally from 5 minutes to 12 hours, preferably from 5 minutes to 6 hours.

The cyclization may be attained in the same manner as in the above step 6, or according to the method, or according to a combination thereof with an ordinary method.

The compound (I-9) or (I-10) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

Compounds (I-9-1):

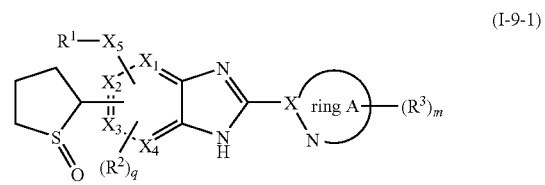

(I-9-1)

or compounds (I-9-2):

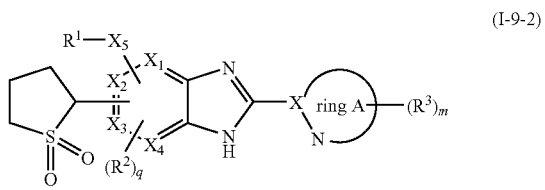

(I-9-2)

(wherein the symbols have the same meanings as above) of the invention may be produced by oxidizing the above compound (I-9). The oxidizing agent usable herein is, for example, OXONE.

The amount of the oxidizing agent to be used may be generally from 0.1 to 10 equivalents relative to the equivalent of the compound (I-9), preferably from 0.3 to 3 equivalents.

Not specifically defined, the reaction solvent may be any one not interfering with the reaction, and includes, for example, methanol, tetrahydrofuran, chloroform, water. Of those, preferred is a mixed solvent of methanol and water.

The reaction temperature may be generally from 10 minutes to 24 hours, preferably from 30 minutes to 6 hours.

The reaction time may be generally from −20 to 60° C., preferably from 0° C. to room temperature.

The compound (I-9-1) or (I-9-2) thus obtained may be isolated and purified in any known manner for isolation and purification, for example, through concentration, concentration under reduced pressure, crystallization, solvent extraction, reprecipitation, chromatography.

Compounds (I-11) of the invention may be produced, for example, according to the following method:

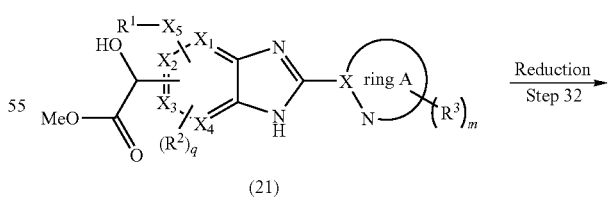

(21)

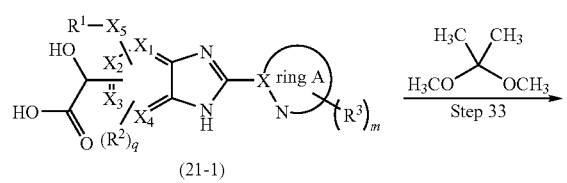

(21-1)

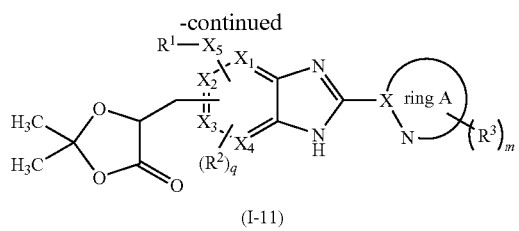

(I-11)

(Step 32)

This step is a method for producing a compound (21-1) by hydrolyzing the above compound (21).

This step may be attained in the presence of sodium hydroxide.

The amount of 5 N sodium hydroxide to be used may be generally from 1 to 100 equivalents relative to 1 equivalent of the compound (25), preferably from 1 to 10 equivalents.

Not specifically defined, the reaction solvent may be any one not interfering with the reaction, and includes, for example, methanol, tetrahydrofuran, water, or their mixed solvents. Preferred is a mixed solvent of methanol or tetrahydrofuran with water.

The reaction temperature may be generally from 0 to 150° C., preferably from room temperature to 100° C.

The reaction time may be generally from 1 to 48 hours, preferably from 1 to 24 hours.

The compound (21-1) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 33)

This step is a method for producing a compound (I-11) of the invention by reacting the above compound (21-1) with 2,2-dimethoxypropane.

The amount of 2,2-dimethoxypropane to be used in this step may be generally from 0.5 to 100 equivalents relative to 1 equivalent of the compound (21-1), preferably from 1 to 10 equivalents.

Not specifically defined or not used, the reaction solvent may be any one not interfering with the reaction, and includes, for example, acetone, tetrahydrofuran. Of those, preferred is acetone.

The reaction temperature may be generally from 0 to 150° C., preferably from room temperature to 100° C.

The reaction time may be generally from 10 minutes to 12 hours, preferably from 30 minutes to 6 hours.

The compound (I-11) thus obtained may be isolated and purified in any known manner for isolation and purification, for example, through concentration, concentration under reduced pressure, crystallization, solvent extraction, reprecipitation, chromatography.

Compounds (I-12) of the invention may be produced, for example, according to the following method:

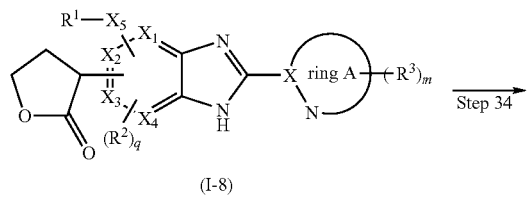

(I-8)

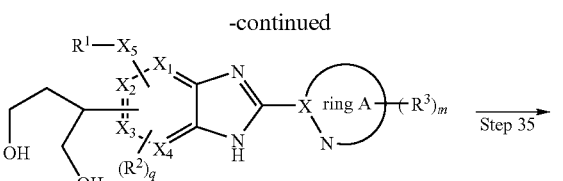

(29)

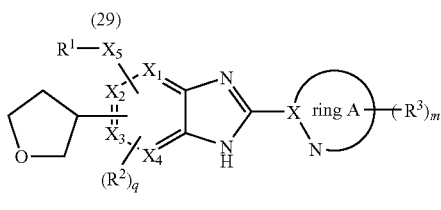

(I-12)

(Step 34)

This step is a method for producing a compound (29) by reducing the above compound (I-8).

The reducing agent to be used in this step includes, for example, lithiumaluminium hydride, diisobutylaluminium hydride, sodium borohydride; and if necessary, these may be used.

The amount of the reducing agent to be used may be generally from 0.5 to 10 equivalents relative to 1 equivalent of the compound (I-8).

Not specifically defined, the reaction solvent may be any one not interfering with the reaction, and includes, for example, ether, chloroform, methanol, ethanol, water, tetrahydrofuran. Of those, preferred are tetrahydrofuran, methanol.

The reaction temperature may be generally from 0 to 60° C., preferably from 0° C. to room temperature.

The reaction time may be generally from 30 minutes to 24 hours, preferably from 1 to 12 hours.

The compound (29) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step 35)

This step is a method for producing a compound (I-12) of the invention by cyclizing the compound (29) obtained in the previous step 35, in the presence of an acid.

The cyclization may be attained in the same manner as in the above step 6, or according to the method, or according to a combination thereof with an ordinary method.

The compound (I-12) thus obtained may be isolated and purified in any known manner for isolation and purification, for example, through concentration, concentration under reduced pressure, crystallization, solvent extraction, reprecipitation, chromatography.

The compounds (1):

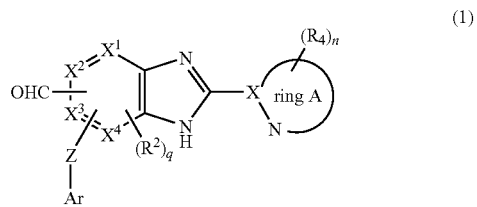

(1)

(wherein the symbols have the same meanings as above), or compounds (I-1) derived from the compound (I) by introducing a protective group $R^{pro}$ thereinto,

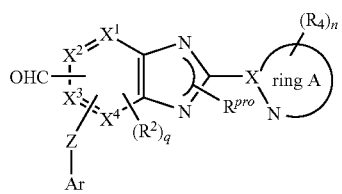
(1-1)

or the compounds (8):

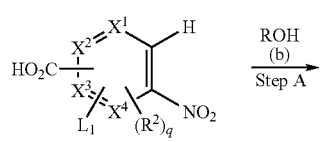
(8)

or compounds (8-1) derived from the compound (8) by introducing a protective group $R^{pro}$ thereinto,

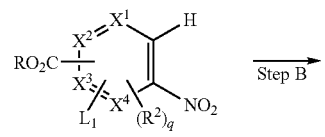
(8-1)

which are used in producing the compounds of the invention, may be produced, for example, according to the following method:

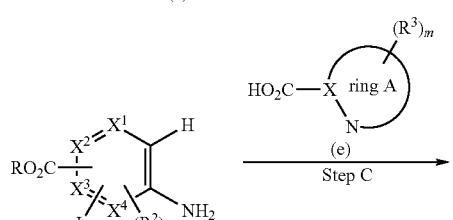

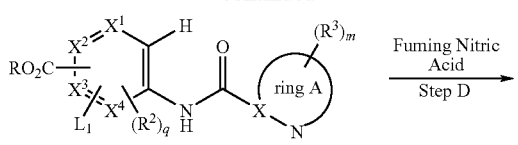
(f)
Fuming Nitric Acid
Step D

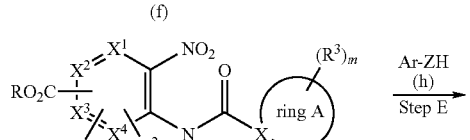
(g)
Ar-ZH
(h)
Step E

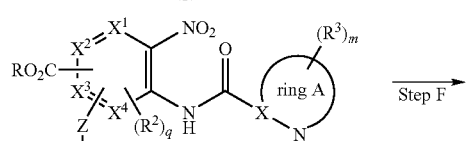
(i)
Step F

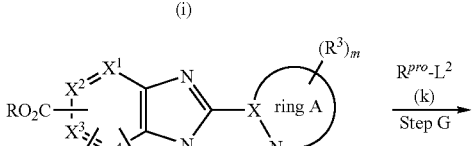
(j)
$R^{pro}\text{-}L^2$
(k)
Step G

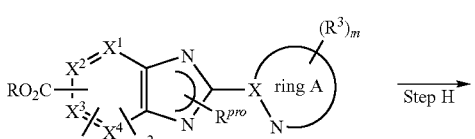
(j-1)
Step H

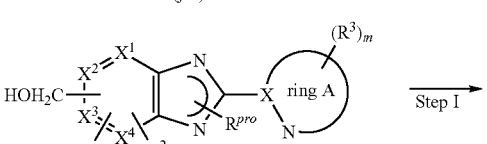
(8-1)
Step I

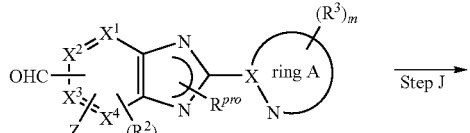
(I-1)
Step J

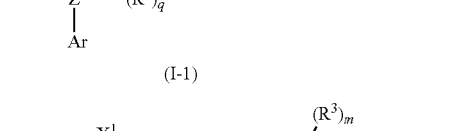
(I)
Step I-2

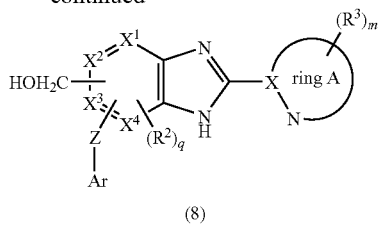

(8)

(In the formula, R represents a lower alkyl group; $R^{pro}$ presents a protective group in the imidazole ring; $L_1$ and $L_2$ each represent a leaving group; and the other symbols have the same meanings as above.)

(Step A)

This step is a method for producing a compound (c) by reacting a compound (a) with a compound (b) in the presence of an acid catalyst.

$L_1$ may be any one capable of producing a compound (i) through reaction with a compound (h) Ar—ZH in the step 4. For example, it includes a fluorine atom, a chlorine atom, a bromine atom, and is preferably a fluorine atom.

The acid catalyst to be used in this step includes, for example, sulfuric acid, p-toluenesulfonic acid, methanesulfonic acid, hydrochloric acid, thionyl chloride.

The amount of the acid catalyst to be used may be generally from 0.01 to 10 equivalents relative to 1 equivalent of the compound (a), preferably from 0.1 to 1 equivalent.

The compound (a) to be used includes, for example, 2-fluoro-4-nitrobenzoic acid, 2-fluoro-5-nitrobenzoic acid, 5-fluoro-2-nitrobenzoic acid, 3-fluoro-5-nitrobenzoic acid.

The lower alkyl group for R may have the same meaning as that of the above-defined lower alkyl group.

The compound (b) may serve also as a reaction solvent, including, for example, methanol, ethanol.

The amount of the compound (b) to be used may be generally a solvent amount relative to 1 equivalent of the compound (a).

The reaction temperature may be generally from room temperature to the reflux temperature of the reaction solvent, preferably from 60° C. to the reflux temperature of the reaction solvent.

The reaction time may be generally from 1 to 120 hours, preferably from 24 to 72 hours.

The reaction solvent to be used in this step includes, for example, methanol, ethanol, toluene, tetrahydrofuran, dimethylformamide.

The compound (c) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step B)

This step is a method for producing a compound (d) by reducing the nitro group that the compound (c) obtained in the previous step A has.

A method well known to those skilled in the art is applicable to the reduction of this step.

The reduction of this step concretely includes, for example, catalytic reduction with hydrogen, formic acid, ammonium formate or hydrazine hydrate and palladium, platinum or nickel catalyst; reduction with hydrochloric acid or ammonium chloride and iron; and reduction with methanol and tin chloride.

The amount of the reducing agent to be used in this step varies, depending on the compound and the solvent to be used, but may be generally from 1 to 50 equivalents relative to 1 equivalent of the compound (c), preferably from 2 to 20 equivalents.

The reaction temperature may be generally from −10 to 100° C., preferably from 0 to 50° C.

The reaction time may be generally from 1 to 20 hours, preferably from 1 to 5 hours.

Not specifically defined, the reaction solvent may be any one not interfering with the reaction, and includes, for example, methanol, N,N-dimethylformamide, ethyl acetate, tetrahydrofuran, and their mixed solvents.

The compound (d) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step C)

This step is a method for producing a compound (f) by reacting the compound (d) obtained in the previous step B with a compound (e).

In the amidation of this step, used is a carboxylic acid or its reactive derivative of the compound (5).

The compound (e) for use herein includes, for example, pyridine-2-carboxylic acid, pyrazine-2-carboxylic acid, pyrimidine-4-carboxylic acid, pyrimidine-2-carboxylic acid, thiazole-2-carboxylic acid, isoxazole-3-carboxylic acid, 5-methyl-isoxazole-3-carboxylic acid, 1-methyl-1H-imidazole-4-carboxylic acid, imidazole-2-carboxylic acid, 1-methyl-1H-imidazole-2-carboxylic acid, imidazole-1-carboxylic acid, [1,2,4]triazole-1-carboxylic acid, [1,2,4]triazole-3-carboxylic acid, [1,2,3]triazole-4-carboxylic acid, 3-methyl-[1,2,4]thiadiazole-5-carboxylic acid, [1,2,5]thiadiazole-3-carboxylic acid, [1,2,3]oxadiazole-3-carboxylic acid, pyrazole-3-carboxylic acid.

The amount of the compound (e) or its reactive derivative to be used may be generally from 0.1 to 100 equivalents relative to 1 equivalent of the compound (d), preferably from 0.1 to 20 equivalents, more preferably from 0.1 to 3 equivalents.

The reactive derivative of the compound (e) includes, for example, mixed acid anhydrides, active esters, active amides; and these may be obtained according to the method described in WO98/05641.

In the above reaction, when a carboxylic acid of the compound (e) is used, for example, it is desirable that the reaction is attained in the presence of a condensing agent such as carbonyldiimidazole, N,N'-dicyclohexylcarbodiimide, 1-ethyl-3-(3-dimethylaminopropyl)carbodiimide, diphenylphosphorylazide, dipyridyl disulfide-triphenyl phosphine, preferably carbonyldiimidazole.

The amount of the condensing agent to be used is not strictly limited, but in general, it may be from 0.1 to 100 equivalents relative to the compound (e), more preferably from 0.1 to 10 equivalents.

The reaction is generally attained in an inert solvent, and the inert solvent includes, for example, tetrahydrofuran, N,N-dimethylformamide, 1,4-dioxane, benzene, toluene, methylene chloride, chloroform, carbon tetrachloride, 1,2-dichloroethane, pyridine, or mixtures of such solvents.

The reaction temperature may be generally from 0° C. to the reflux temperature of the reaction solvent, preferably from room temperature to the reflux temperature of the reaction solvent.

The reaction time may be generally from 0.1 hours to 72 hours, preferably from 0.5 hours to 24 hours.

The reaction may be attained in the presence of a base and a condensation promoter for smoothly promoting the reaction.

The base includes 4-dimethylaminopyridine, triethylamine.

The amount of the base to be used may be generally from 0.1 to 100 equivalents relative to 1 mol of the carboxylic acid or its reactive derivative of the compound (e), preferably from 0.1 to 1 equivalent.

The condensation promoter includes N-hydroxybenzotriazole hydrate, N-hydroxysuccinimide.

The amount of the condensation promoter to be used may be generally from 1 to 100 equivalents relative to 1 mol of the carboxylic acid or its reactive derivative of the compound (e), preferably from 1 to 5 equivalents.

In the above reaction, in case where an amino group or an imino group not participating in the reaction exists in the reactant substance, then it is desirable that the amino group or imino group is protected with a protective group for amino group or imino group, then the reaction is attained, and after the reaction, the protective group is removed.

The compound (f) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step D)

This step is a method for producing a compound (g) by reacting the compound (f) obtained in the previous step C with fuming nitric acid.

The amount of fuming nitric acid to be used in this step may be generally from 1 to 100 equivalents relative to 1 equivalent of the compound (f), preferably from 2 to 20 equivalents.

The reaction temperature may be generally from 0 to 100° C., preferably from 10 to 50° C.

The reaction time may be generally from 0.1 to 48 hours, preferably from 0.5 to 12 hours.

The compound (g) may also be produced by reacting the above compound (f) with potassium nitrate in the presence of an acid.

The amount of potassium nitrate to be used may be generally from 1 to 100 equivalents relative to 1 equivalent of the compound (f), preferably from 1 to 5 equivalents.

The acid to be used includes, for example, trifluoroacetic acid, hydrochloric acid, sulfuric acid, nitric acid.

The amount of the acid to be used may be generally from 1 equivalent to a solvent amount relative to 1 equivalent of the compound (f), preferably from 1 to 100 equivalents. The reaction temperature may be generally from 0° C. to the reflux temperature of the solvent, preferably from room temperature to 100° C.

The reaction time may be generally from 0.1 to 72 hours, preferably from 0.5 hours to 12 hours.

Not specifically defined, the reaction solvent may be any one not interfering with the reaction, and includes, for example, chloroform, dichloromethane.

The compound (g) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step E)

This step is a method for producing a compound (i) by reacting the compound (g) obtained in the previous step D with a compound (h) in the presence of a base.

The amount of the compound (h) to be used may be generally from 0.1 to 20 equivalents relative to 1 equivalent of the compound (g), preferably from 0.5 to 5 equivalents.

The compound (h) to be used includes, for example, 4-methanesulfonylphenol, 4-ethanesulfonylphenol, 3-chloro-4-methanesulfonylphenol, 6-methanesulfonyl-pyridin-3-ol, 6-ethanesulfonyl-pyridin-3-ol, 4-cyanophenol, 6-(5-methyl-[1,2,4]thiadiazol-3-yl)-pyridin-3-ol, 6-(5-methyl-1,2,4-oxadiazol-3-yl)-3-pyridinol, 4-(5-methyl-1,2,4-oxadiazol-3-yl)phenol. These compounds may be commercial compounds, or may be produced starting from commercial compounds and in a method well known to those skilled in the art, or according to the method, or according to a combination thereof with an ordinary method.

The amount of the base to be used may be generally from 0.1 to 20 equivalents relative to 1 equivalent of the compound (g), preferably from 0.5 to 5 equivalents.

The base to be used may be any one capable of producing a compound (i) in the step of reacting the compound (g) with the compound (h). For example, it includes sodium hydride, cesium carbonate, sodium carbonate, potassium carbonate, potassium phosphate, potassium acetate, potassium tert-butyrate, triethylamine. Of those, preferred are potassium carbonate, cesium carbonate. In case where the compound (h) is a primary or secondary amine, then the reaction of this step may be attained in the absence of a base.

The reaction temperature may be generally from 0° C. to the reflux temperature of the reaction solvent, preferably from room temperature to the reflux temperature of the reaction solvent.

The reaction time may be generally from 0.1 to 72 hours, preferably from 0.5 to 5 hours.

The reaction solvent may be an inert solvent and is not specifically defined so far as it does not interfere with the reaction. Concretely, it includes, for example, pyridine, toluene, tetrahydrofuran, 1,4-dioxane, N,N-dimethylformamide, N,N-dimethylacetamide, dimethylsulfoxide, 1-methyl-2-pyrrolidinone.

The compound (i) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step F)

This step is a method for producing a compound (j) by reducing the nitro group that the compound (i) obtained in the previous step E has, and simultaneously dehydrating and cyclizing it in the presence of an acid catalyst.

Regarding its reaction condition, this step may be attained in the same manner as in the above step B, or according to the method, or according to a combination thereof with an ordinary method.

The compound (i) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step G)

This step is a method for producing a compound (j-1) by reacting the compound (j) obtained in the previous step F with a compound (k) in the presence of a base.

The reaction in this step is introduction of a protective group into an aromatic amino group, and this may be effected in the same manner as in the method described in literature (e.g., Protective Groups in Organic Synthesis, by T. W. Green, 2nd Ed., by John Wiley & Sons, 1991), or according to the method, or according to a combination thereof with an ordinary method.

$L_2$ in the compound (k) is, for example, a halogen atom, preferably a chlorine atom or a bromine atom.

The compound (k) to be used includes 2-(trimethylsilyl) ethoxymethyl chloride (SEMCl), methoxymethyl chloride (MOMCl).

The amount of the compound (k) to be used may be generally from 1 to 10 equivalents relative to 1 equivalent of the compound (j), preferably from 1 to 3 equivalents.

The base to be used is, for example, sodium hydride.

The amount of the base to be used may be generally from 1 to 10 equivalents, preferably from 1 to 3 equivalents.

The reaction temperature may be generally from −20 to 50° C., preferably from 0° C. to room temperature.

The reaction time may be generally from 0.1 to 12 hours, preferably from 0.1 to 3 hours.

Not specifically defined, the reaction solvent may be any one not interfering with the reaction, and includes, for example, N,N-dimethylformamide, tetrahydrofuran, methylene chloride.

The compound (j-1) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step H)

This step is a method for producing a compound (8-1) by reducing the ester group that the compound (j-1) obtained in the previous step G has.

The reducing agent to be used in this step includes lithiumaluminium hydride (LiAlH$_4$), lithium borohydride, sodium borohydride. The ester moiety that the compound (j-1) has may be hydrolyzed into a carboxylic acid, and this may be processed according to the method described in literature (e.g., SYNLETT, 1995, Vol. 8, pp. 839-840), or according to a method similar to it, or according to a combination thereof with an ordinary method, thereby producing a compound (8-1).

The amount of the reducing agent to be used may be generally from 1 to 20 equivalents relative to 1 equivalent of the compound (j-1), preferably from 1 to 3 equivalents.

The reaction temperature may be generally from 0 to 80° C., preferably from 0° C. to room temperature.

The reaction time may be generally from 0.1 to 24 hours, preferably from 0.1 to 3 hours.

Not specifically defined, the reaction solvent may be any one not interfering with the reaction, and includes, for example, methanol, N,N-dimethylformamide, ethyl acetate, tetrahydrofuran, and their mixed solvents.

The compound (8-1) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step I)

This step is a method for producing a compound (I-1) by oxidizing the hydroxyl group that the compound (8-1) obtained in the previous step H has.

The reaction in this step may be attained in the same manner as in the method described in literature (e.g., Journal of the American Chemical Society, 1967, Vol. 89, pp. 5505-5507), or according to the method, or according to a combination thereof with an ordinary method.

The compound (1-1) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

(Step J)

This step is a method for producing a compound (1) by removing the protective group $R^{pro}$ that the compound (1-1) obtained in the previous step I has.

The removal of the protective group may be attained in the same manner as in the method described in literature (e.g., Protective Groups in Organic Synthesis, by T. W. Green, 2nd Ed., John Wiley & Sons, 1991), or according to the method, or according to a combination thereof with an ordinary method. For example, when the protective group is SEM (trimethylsilylethoxymethyl) group, the compound (8-1) may be reacted with trifluoroacetic acid to remove the SEM group.

The compound (1) thus obtained may be isolated and purified in any known manner for isolation and purification, for example, through concentration, concentration under reduced pressure, crystallization, solvent extraction, reprecipitation, chromatography (Step I-2)

This step is a method for producing a compound (8) by removing the protective group $R^{pro}$ that the above compound (8-1) has.

The reaction in this step may be attained in the same manner as that for the method of removing the protective group $R^{pro}$ that the above compound (1-1) has, or according to the method, or according to a combination thereof with an ordinary method.

The compound (8) thus obtained may be subjected to the next step, after isolated and purified in any known manner for isolation and purification, for example, through concentration, concentration under reduced pressure, crystallization, solvent extraction, reprecipitation, chromatography, or not after isolated and purified.

In producing the compounds of the invention, when the compound (1-1) is used as the starting material in place of the compound (1), then the protective group $R^{pro}$ that the compound (1-1) has may be removed, if desired.

In producing the compounds of the invention, when the compound (8-1) is used as the starting material in place of the compound (8), then the protective group $R^{pro}$ that the compound (8-1) has may be removed, if desired.

In case where an amino group or an imino group not participating in the reaction exists in the reactant substance, then it is desirable that the amino group or the imino group is suitably protected with a protective group for amino or imino group, then the reaction is attained, and after the reaction, the protective group is removed.

The hetero ring-substituted benzimidazole derivatives that the invention provides may exist as their pharmaceutically-acceptable salts, and the salts may be produced from the compounds (I-1) to (I-12) falling within the scope of the compounds (I) of the invention in an ordinary manner.

Concretely, when the compounds of formula (I-1) to (I-12) have a basic group derived from, for example, an amino group or a pyridyl group in the molecule, then the compounds may be processed with acid so as to convert them into the corresponding pharmaceutically-acceptable salts.

The compounds of formulae (I-1) to (I-12) and their pharmaceutically-acceptable salts are within the scope of the formula (I).

The acid-addition salts include, for example, hydrohalides such as hydrochlorides, hydrofluorides, hydrobromides, hydroiodides; inorganic acid salts such as nitrates, perchlorates, sulfates, phosphates, carbonates; lower alkylsulfonates such as methanesulfonates, trifluoromethanesulfonates, ethanesulfonates; arylsulfonates such as benzenesulfonates, p-toluenesulfonates; organic acid salts such as fumarates, succinates, citrates, tartrates, oxalates, maleates; other organic acid-addition salts with amino acid such as glutamates, aspartates. When the compounds of the invention have an acid group in the molecule, for example, when they have a carboxyl group, then the compounds may be processed with a base so as to convert them into the corresponding pharmaceutically-acceptable salts. The base-addition salts include, for example, alkali metal salts with sodium or potassium; alkaline earth metal salts with calcium or magnesium; ammonium salts; organic base-addition salts with guanidine, triethylamine, dicyclohexylamine, etc. In addition, the compounds of the invention may also be in any other form of hydrates or solvates of their free compounds or their salts.

In producing medicines for prevention and remedy of type II diabetes or diseases or symptoms associated with it, the compounds of formula (I) of the invention may be combined with carrier substances.

The dose of the compounds of formula (I) of the invention for prevention or remedy of diseases naturally varies, depending on the property of the symptom to be treated, the specific compound selected for it and the administration route.

In addition, the dose also varies depending on the age, the body weight and the sensitivity of patients. In general, the daily dose for one-time or plural-times administration may be from about 0.001 mg/kg-body weight to about 100 mg/kg-body weight, preferably from about 0.01 mg/kg-body weight to about 50 mg/kg-body weight, even more preferably from about 0.1 mg/kg-body weight to about 10 mg/kg-body weight. As the case may be, administration of a dose over the range may be necessary.

An example of a suitable dose for oral administration is described. The daily dose for one-time or two- to four-times administration may be at least from about 0.01 mg to at most 2.0 g. Preferably, the daily administration frequency is once or twice a day, and the daily dose is from about 1.0 mg to about 200 mg. More preferably, the daily dose is from about 10 mg to 100 mg for one-time administration a day.

For intravenous administration or oral administration, a typical dose of the compound (1) may be from about 0.001 mg/day/kg-body weight to about 100 mg/day/kg-body weight (preferably from 0.01 mg/day/kg-body weight to about 10 mg/day/kg-body weight), more preferably from about 0.1 mg/day/kg-body weight to 10 mg/day/kg-body weight.

As so mentioned hereinabove, the pharmaceutical composition of the invention comprises a compound of formula (I) and a pharmaceutically-acceptable carrier. The term "composition" is meant to contain not only a product produced by directly or indirectly combining, hybridizing or aggregating 2 or more ingredients, a product produced as a result of dissociation of one or more ingredients, or a compound produced as a result of reaction or interaction of different types of ingredients, but also an active and inactive ingredient of constituting a carrier (pharmaceutically-acceptable vehicle).

As combined with a pharmaceutically-acceptable carrier, the composition of the invention preferably contains a compound of formula (I) in an amount effective for remedy and prevention of type II diabetes and for retardation of the onset of the disease.

For administering the effective dose of the compound of the invention to mammals, especially to humans, employable is any suitable administration route. For example, the route may be oral administration, rectal administration, local administration, intravenous administration, ophthalmic administration, lung administration or nasal administration. Examples of the administration forms are tablets, troches, powders, suspensions, solutions, capsules, creams, aerosols. Preferred are oral tablets.

In preparing oral compositions, usable are any ordinary pharmaceutical media. Their examples are water, glycol, oil, alcohol, fragrant additives, preservatives, colorants. In preparing liquid compositions for oral administration, for example, mentioned are suspensions, elixirs and solutions. Their carriers are, for example, starch, sugar, microcrystalline cellulose, diluent, granulating promoter, lubricant, binder, disintegrator. In preparing solid compositions for oral administration, for example, mentioned are powders, capsules and tablets. Above all, such solid compositions for oral administration are preferred.

In view of the easiness in their administration, tablets and capsules are the most advantageous forms for oral administration. If desired, the tablets may be coated according to standard aqueous or non-aqueous coating techniques.

In addition to the above-mentioned ordinary administration modes for them, the compounds of formula (I) may also be administered according to controlled release systems and/or controlled delivery systems, for example, as in U.S. Pat. Nos. 3,845,770, 3,916,899, 3,536,809, 3,598,123, 3,630,200 and 4,008,719.

The pharmaceutical composition of the invention suitable for oral administration includes capsules, cashews and tablets that contain a predetermined amount of the active ingredient in the form of powders or granules thereof, or in the form of water-soluble liquids, water-insoluble liquids, oil-in-water emulsions or water-in-oil emulsions thereof. These compositions may be prepared in any pharmaceutical methods, and all the methods include a process of combining the active ingredient with a carrier of one or more necessary ingredients.

In general, the active ingredient is uniformly and fully mixed with a liquid carrier, or a well-separated solid carrier or with both the two, and then, if desired, the product is shaped into suitable forms to prepare the composition. For example, tablets are produced through compression and shaping, optionally along with one or more side components. Using a suitable machine, compressed tablets may be produced by mixing the active ingredient optionally with binder, lubricant, inert vehicle, surfactant or dispersant and compressing the resulting mix in any desired manner into powders or granules.

Shaped tablets may be prepared by shaping a mixture of a powdery wet compound and an inert liquid diluent, using a suitable machine.

Preferably, the tablets each contain from about 1 mg to 1 g of the active ingredient; and the cashews and the capsules each contain from about 1 mg to 500 mg of the active ingredient.

Examples of the administration modes of the compounds of formula (I) for pharmaceutical use are as follows:

TABLE 1

Suspension for Injection (I.M.)

| | mg/ml |
|---|---|
| compound of formula (I) | 10 |
| methyl cellulose | 5.0 |
| Tween 80 | 0.5 |
| benzyl alcohol | 9.0 |
| benzalkonium chloride | 1.0 | water for injection added to make 1.0 ml.

TABLE 2

Tablets

| | mg/tablet |
|---|---|
| compound of formula (I) | 25 |
| methyl cellulose | 415 |
| Tween 80 | 14.0 |
| benzyl alcohol | 43.5 |
| magnesium stearate | 2.5 |
| total | 500 mg |

TABLE 3

Capsules

| | mg/capsule |
|---|---|
| compound of formula (I) | 25 |
| lactose powder | 573.5 |
| magnesium stearate | 1.5 |
| total | 600 mg |

TABLE 4

Aerosol

| | per one container |
|---|---|
| compound of formula (I) | 24 mg |
| lecithin, NF Liq. Conc. | 1.2 mg |
| trichlorofluoromethane, NF | 4.025 g |
| dichlorodifluoromethane, NF | 12.15 g |

The compounds of formula (I) may be used, as combined with any other medicines usable not only for type II diabetes-associated diseases or symptoms but also for remedy/prevention/retardation of the onset of type II diabetes. The additional medicines may be administered in any administration route and dose generally employed in the art, simultaneously with or separately from the compound of formula (I).

In case where the compound of formula (I) is used along with one or more other medicines, then a pharmaceutical composition comprising the compound of formula (I) and the additional medicines is preferred. Accordingly, the pharmaceutical composition of the invention may comprise not only the compound of formula (I) but also one or more such active ingredients. Examples of the active ingredients that may be combined with the compounds of formula (I) are mentioned below, which, however, are not limitative. These may be separately administered or may be administered simultaneously as contained in the same pharmaceutical composition.

(a) other glucokinase activators,
(b) bis-guanides (e.g., buformin, metoformin, fenformin,),
(c) PPAR agonists (e.g., triglytazon, pioglytazon, nosiglytazon),
(d) insulin,
(e) somatostatin,
(f) α-glucosidase inhibitors (e.g., boglybose, miglytol, acarbose),
(g) insulin secretion promoters (e.g., acetohexamide, calbutamide, chlorpropamide, glybomlide, glycrazide, glymerpide, glypidide, glyquidine, glysoxepide, glyburide, glyhexamide, glypinamide, fenbutamide, trazamide, tolbutamide, tolcyclamide, nateglynide, repaglynide), and
(h) DPP-IV (dipeptidyl peptidase IV) inhibitors.

The weight ratio of the compound of formula (I) to the second active ingredient may vary within a broad range, and depends on the effective amount of the individual active ingredients. Accordingly, for example, when the compound of formula (I) is combined with a PPAR agonist, then the weight ratio of the compound of formula (I) to the PPAR agonist may be generally from about 1000/1 to 1/1000, preferably from about 200/1 to 1/200. The combination of the compound of formula (I) and the other active ingredient may be within the above-mentioned range. In any case, an effective amount of the individual active ingredients should be in the combination.

The glucokinase-activating potency of the compounds of formula (I) of the invention and a test method for it are described below.

The excellent glucokinase-activating effect of the compounds of formula (I) may be determined by a method described in references (for example, Diabetes, Vol. 45, pp. 1671-1677, 1996), or in accordance with it.

The glucokinase activity may be determined not by directly measuring glucose-6-phosphate but by measuring the level of Thio-NADH, which is produced when a reporter enzyme, glucose-6-phosphate dehydrogenase produces phosphogluconolactone from glucose-6-phosphate, and based on the level, the level of glucokinase activation may be determined.

In this assay, used was a recombinant human liver GK, which was expressed by $E.$ $coli$ as a FLAG fusion protein therein and was purified by ANTIFLAG M2 AFFINITY GEL (Sigma).

Using a flat-bottomed 96-well plate, the assay was carried out at 30° C. 69 µl of an assay buffer (25 mM Hepes Buffer/pH=7.2, 2 mM $MgCl_2$, 1 mM ATP, 0.5 mM TNAD, 1 mM dithiothreitol) was put into the plate, and 1 µl of a DMSO solution of the compound or DMSO alone as a control was added thereto. Next, 20 µl of an enzyme mixture (FLAG-GK, 20 U/ml G6PDH) cooled in ice was added to it, and 10 µl of a substrate, 25 mM glucose was added to it, and the reaction was initiated (final glucose concentration=2.5 mM).

After the start of the reaction, the increase in the absorbance at 405 nm was measured for 12 minutes at intervals of 30 seconds, and the increase for the first 5 minutes was used for evaluating the compound tested. FLAG-GK was added so that the absorbance increase after 5 minutes in the presence of 1% DMSO could be from 0.04 to 0.06.

The OD level of the DMSO control was set as 100%; and the OD level of the test compound at different concentrations was determined. From the OD level at each concentration, Emax (%) and EC50 (µM) were computed and used as the index of the GK-activating potency of the compound.

The GK-activating potency of the compounds of the invention was measured according to the method as above, and the results are shown in Table 5 below.

TABLE 5

| Example No. | Emax (%) | EC50 (μM) |
|---|---|---|
| Example 1 | 923 | 1.18 |
| Example 17 | 1230 | 1.40 |
| Example 23 | 1100 | 1.42 |
| Example 29-1 | 1070 | 0.60 |
| Example 31 | 1070 | 1.58 |
| Example 36 | 978 | 0.88 |

As in the above Table, the compounds of the invention have an excellent GK-activating potency indicated by Emax and EC50.

EXAMPLES

The invention is described more concretely with reference to the following Preparation Examples and Examples, by which, however, the invention should not be limited at all.

Preparation Example 1

10 parts of the compound of Example 1, 15 parts of heavy magnesium oxide and 75 parts of lactose are uniformly mixed to give a powdery or particulate preparation of at most 350 μm in size. The preparation is encapsulated to prepare capsules.

Preparation Example 2

45 parts of the compound of Example 1, 15 parts of starch, 16 parts of lactose, 21 parts of crystalline cellulose, 3 parts of polyvinyl alcohol and 30 parts of distilled water are uniformly mixed, then ground, granulated and dried, and thereafter sieved to prepare granules having a size of from 1410 to 177 μm in diameter.

Preparation Example 3

Granules are prepared in the same manner as in Preparation Example 2. 3 parts of calcium stearate is added to 96 parts of the granules, and shaped under compression to give tablets having a diameter of 10 mm.

Preparation Example 4

10 parts of crystalline cellulose and 3 parts of calcium stearate are added to 90 parts of the granules obtained according to the method of Preparation Example 2, and shaped under compression to give tablets having a diameter of 8 mm. These are coated with a mixture suspension of syrup gelatin and precipitated calcium carbonate to prepare sugar-coated tablets.

In the following, the invention is described more concretely with reference to Preparation Examples, Examples and Reference Examples, by which, However, the Invention should not be limited at all.

In the thin-layer chromatography in Examples, Silicagel 60F$_{245}$ (Merck) was used for the plate, and a UV detector was used for detection. For the column silica gel, used was Wakogel™ C-300 (Wako Pure Chemical); and for the reversed-phase column silica gel, used was LC-SORB™ SP-B-ODS (Chemco) or YMC-GEL™ ODS-AQ 120-S50 (Yamamura Chemical Laboratory).

The meanings of the abbreviations in the following Examples are shown below.
i-Bu: isobutyl
n-Bu: n-butyl
t-Bu: t-butyl
Me: methyl
Et: ethyl
Ph: phenyl
i-Pr: isopropyl
n-Pr: n-propyl
CDCl$_3$: heavy chloroform
CD$_3$OD: heavy methanol
DMSO-d$_6$: heavy dimethylsulfoxide The meanings of the abbreviations in the following nuclear magnetic resonance spectra are shown below.
s: singlet
d: doublet
dd: double-doublet
t: triplet
m: multiplet
br: broad
brs: broad singlet
q: quartet
J: coupling constant
Hz: hertz Example 1

5-(1,3-dioxolan-2-yl)-6-(4-(ethylsulfonyl)phenoxy)-2-pyridin-2-yl-1H-benzimidazole P-toluenesulfonic acid monohydrate (9 mg) was added to an ethylene glycol (0.2 ml) solution of 5-carbaldehyde-6-(4-(ethylsulfonyl)phenoxy)-2-pyridin-2-yl-1H-benzimidazole (18 mg) obtained in Reference Example 10, and the reaction liquid was stirred at 100° C. for 30 minutes. The reaction mixture was purified through silica gel column chromatography (developing solvent: chloroform/methanol=20/1) to obtain the entitled compound as a white solid.

$^1$HNMR (CD$_3$OD) δ: 1.24 (3H, t, J=7.6 Hz), 3.19 (2H, q, J=7.6 Hz), 3.94-3.98 (2H, m), 4.06-4.13 (2H, m), 6.02 (1H, s), 7.13 (2H, d, J=8.8 Hz), 7.21-7.39 (1H, m), 7.48 (1H, dd, J=7.6, 4.7 Hz), 7.83-8.03 (2H, m), 7.85 (2H, d, J=8.8 Hz), 8.30 (1H, d, J=7.6 Hz), 8.72 (1H, d, J=4.7 Hz)
ESI-MS (m/e): 452 [M+H]$^+$

Example 2

5-(1,3-dioxolan-2-yl)-6-((6-(ethylsulfonyl)pyridin-3-yl)oxy)-2-pyridin-2-yl-1H-benzimidazole Using 5-carbaldehyde-6-((6-(ethylsulfonyl)pyridin-3-yl)oxy)-2-pyridin-2-yl-1H-benzimidazole obtained in Reference Example 12 and ethylene glycol, the entitled compound was obtained as a colorless solid in the same manner as in Example 1, or according to the method, or according to a combination thereof with an ordinary method.

$^1$HNMR (CD$_3$OD) δ: 1.24 (3H, t, J=7.4 Hz), 3.39 (2H, q, J=7.4 Hz), 3.93-3.99 (2H, m), 4.04-4.12 (2H, m), 6.07 (1H, s), 7.41 (1H, brs), 7.47-7.53 (2H, m), 7.95-8.02 (2H, m), 8.04 (1H, d, J=8.8 Hz), 8.30 (1H, d, J=7.4 Hz), 8.47 (1H, d, J=2.7 Hz), 8.74 (1H, d, J=4.7 Hz)
ESI-MS (m/e): 453 [M+H]+

Example 3

5-(4-(hydroxymethyl)-1,3-dioxolan-2-yl)-6-(4-(ethylsulfonyl)phenoxy)-2-pyridin-2-yl-1H-benzimidazole Using 2-(hydroxymethyl)-1,3-propanediol, the entitled compound was obtained as a colorless solid in the same manner as in Example 1, or according to the method, or according to a combination thereof with an ordinary method.

$^1$HNMR (CD$_3$OD) δ: 1.22 (3H, t, J=7.8 Hz), 3.18 (2H, q, J=7.8 Hz), 3.36-4.37 (5H, m), 5.60-6.20 (1H, m), 7.12 (2H, d, J=8.8 Hz), 7.29 (1H, brs), 7.42-7.49 (1H, m), 7.84 (2H, d, J=8.8 Hz), 7.91-8.22 (2H, m), 7.91-7.99 (2H, m), 8.23-8.30 (1H, m), 8.68-8.73 (1H, m)

ESI-MS (m/e): 482 [M+H]+

Example 4

5-(1,3-dioxan-2-yl)-6-(4-(ethylsulfonyl)phenoxy)-2-pyridin-2-yl-1H-benzimidazole Using 2-(hydroxymethyl)-1,4-butanediol, the entitled compound was obtained as a colorless solid in the same manner as in Example 1, or according to the method, or according to a combination thereof with an ordinary method.

$^1$HNMR (CD$_3$OD) δ: 1.21 (3H, t, J=7.4 Hz), 1.92-2.21 (2H, m), 3.20 (2H, q, J=7.4 Hz), 3.86-3.95 (2H, m), 4.08-4.16 (2H, m), 5.79 (1H, d, J=2.5 Hz), 7.17 (2H, d, J=8.9 Hz), 7.37 (1H, d, J=2.5 Hz), 7.57-7.64 (1H, m), 7.88 (2H, d, J=8.9 Hz), 8.03-8.10 (2H, m), 8.27 (1H, d, J=8.0 Hz), 8.81 (1H, d, J=2.4 Hz)

ESI-MS (m/e): 466 [M+H]+

Example 5

5-(3-acetyl-1,3-oxazolidin-2-yl)-6-(4-(ethylsulfonyl)phenoxy)-2-pyridin-2-yl-1H-benzimidazole Using N-acetylethanolamine, the entitled compound was obtained as a colorless solid in the same manner as in Example 1, or according to the method, or according to a combination thereof with an ordinary method.

$^1$HNMR (CD$_3$OD) δ: 1.22 (3H, t, J=7.4 Hz), 1.94 (3H, s), 3.19 (2H, q, J=7.4 Hz), 3.39 (1H, t, J=5.8 Hz), 3.58 (1H, t, J=5.8 Hz), 3.63 (2H, t, J=5.8 Hz), 6.72-6.78 (1H, m), 6.97-7.58 (1H, m), 7.15 (2H, d, J=8.6 Hz), 7.49-7.54 (1H, m), 7.69-8.20 (1H, m), 7.76-7.83 (1H, m), 7.88 (2H, d, J=8.6 Hz), 7.90 (1H, s), 7.96-8.02 (1H, m), 8.28-8.34 (1H, m), 8.72-8.78 (1H, m)

ESI-MS (m/e): 493 [M+H]+

Example 6

5-(6-(4-(ethylsulfonyl)phenoxy)-2-pyridin-2-yl-1H-benzimidazol-5-yl)tetrahydrofuran-2-ol (Step 1)

Production of 1-(6-(4-ethylsulfonyl)phenoxy)-2-pyridin-2-yl-1H-benzimidazol-5-yl)pent-4-ene-1-ol 4-Bromo-1-butene (0.3 ml) was added to a tetrahydrofuran (5 ml) suspension of magnesium (143 mg), then the reaction liquid was stirred at room temperature for 20 minutes, and this was gradually added to a tetrahydrofuran (10 ml) solution of 5-carbaldehyde-6-(4-(ethylsulfonyl)phenoxy)-2-pyridin-2-yl-1H-benzimidazole (200 mg) obtained in Reference Example 10, with cooling with ice. The reaction liquid was stirred for 20 minutes, then diluted with ethyl acetate, and washed with aqueous saturated ammonium chloride and saturated saline water in that order. This was dried with anhydrous sodium sulfate, and the solvent was evaporated away under reduced pressure to obtain the entitled compound.

(Step 2)

Production of 5-(6-(4-(ethylsulfonyl)phenoxy)-2-pyridin-2-yl-1H-benzimidazol-5-yl)tetrahydrofuran-2-ol Water (2 ml), sodium periodate (340 mg) and aqueous 0.1 M osmium tetroxide solution (0.2 ml) were added in that order to a tetrahydrofuran (6 ml) solution of 1-(6-(4-ethylsulfonyl)phenoxy)-2-pyridin-2-yl-1H-benzimidazol-5-yl)pent-4-ene-1-ol (300 mg) obtained in (step 1). The reaction liquid was stirred overnight at room temperature, then sodium sulfite was added to it and stirred at room temperature for 30 minutes. The reaction liquid was diluted with ethyl acetate, and washed with water and saturated saline water in that order. This was dried with anhydrous sodium sulfate, and the solvent was evaporated away under reduced pressure to obtain the entitled compound.

$^1$HNMR (CDCl$_3$) δ: 1.29 (3H, t, J=7.4 Hz), 1.88-2.53 (4H, m), 3.10 (2H, q, J=7.4 Hz), 5.25-5.26 (1H×½, m), 5.44-5.46 (1H×½, m), 5.64-5.66 (1H×½, m), 5.82-5.83 (1H×½, m), 7.08 (2H, d, J=9.0 Hz), 7.37-7.43 (1H, m), 7.51-7.53 (1H, m), 7.68-7.72 (1H, m), 7.78-7.90 (1H, m), 7.82 (2H, d, J=9.0 Hz), 8.36-8.39 (1H, m), 8.63-8.64 (1H, m)

ESI-MS (m/e): 466 [M+H]+

Example 7

5-(tetrahydrofuran-2-yl)-6-(4-(ethylsulfonyl)phenoxy)-2-pyridin-2-yl-1H-benzimidazole (Step 1)

Production of 1-(6-(4-(ethylsulfonyl)phenoxy)-2-pyridin-2-yl-1H-benzimidazol-5-yl)butane-1,4-diol Sodium borohydride (100 mg) was added to a methanol (5 ml) solution of 54644-(ethylsulfonyl)phenoxy)-2-pyridin-2-yl-1H-benzimidazol-5-yl)tetrahydrofuran-2-ol (284 mg), and the reaction liquid was stirred at room temperature for 5 minutes. The reaction liquid was diluted with chloroform, and washed with water and saturated saline water in that order. This was dried with anhydrous sodium sulfate, and the solvent was evaporated away under reduced pressure to obtain the entitled compound.

(Step 2)

Production of 5-(tetrahydrofuran-2-yl)-6-(4-(ethylsulfonyl)phenoxy)-2-pyridin-2-yl-1H-benzimidazole P-toluenesulfonic acid monohydrate (20 mg) was added to a chloroform (4 ml) solution of 1-(6-(4-(ethylsulfonyl)phenoxy)-2-pyridin-2-yl-1H-benzimidazol-5-yl)butane-1,4-diol (81 mg) obtained in (step 1), and the reaction liquid was stirred overnight with heating under reflux. The solvent was evaporated away under reduced pressure, and the reaction mixture was purified through reversed-phase middle-pressure liquid chromatography (ODS-AS-360-CC (by YMC), mobile phase: water/acetonitrile/0.1% trifluoroacetic acid), and the resulting fraction was diluted with ethyl acetate, washed with aqueous saturated sodium bicarbonate and saturated saline water in that order, and dried with anhydrous sodium sulfate. The solvent was evaporated away under reduced pressure to obtain the entitled compound as a white solid.

$^1$HNMR (CDCl$_3$) δ: 1.28 (3H, t, J=7.4 Hz), 1.52-1.80 (2H, m), 1.90-2.03 (1H, m), 2.27-2.34 (1H, m), 3.10 (2H, q, J=7.4

Hz), 3.90 (1H, q, J=7.4 Hz), 4.07-4.14 (1H, m), 5.03-5.10 (1H, m), 7.08 (2H, d, J=9.0 Hz), 7.35-7.39 (1H, m), 7.42 (1H, s), 7.73 (1H, s), 7.81-7.88 (1H, m), 7.82 (2H, d, J=9.0 Hz), 8.35-8.42 (1H, m), 8.60-8.66 (1H, m), 10.53-10.64 (1H, m)
ESI-MS (m/e): 450 [M+H]+

Example 8

5-(tetrahydrofuran-2-yl)-6-(4-(ethylsulfonyl)phenoxy)-2-pyridin-2-yl-1H-benzimidazol enantiomer A and enantiomer B 5-(Tetrahydrofuran-2-yl)-6-(4-(ethylsulfonyl)phenoxy)-2-pyridin-2-yl-1H-benzimidazole (36 mg) obtained in Example 7 was optically resolved through an optical resolution column (CHIRALPAK AD-H 2 cmϕ×25 cmL, by Daicel Chemical Industry, mobile phase: hexane/ethanol=1/1, flow rate: 10 ml/min) to obtain its enantiomer A (retention time, 14.4 min) and enantiomer B (retention time, 16.3 min) both as a white solid.

Example 9

5-(6-(4-(ethylsulfonyl)phenoxy-2-pyrazin-2-yl-1H-benzimidazol-5-yl)tetrahydrofuran-2-ol Using 5-carbaldehyde-6-(4-(ethylsulfonyl)phenoxy)-2-pyrazin-2-yl-1H-benzimidazole obtained in Reference Example 16, the entitled compound was obtained as a yellow solid in the same manner as in Example 6, or according to the method or according to a combination thereof with an ordinary method.
$^1$HNMR (CD$_3$OD) δ: 1.14-1.26 (3H, m), 1.51-2.60 (4H, m), 3.16-3.22 (2H, m), 5.18-5.76 (2H, m), 7.03-8.29 (6H, m), 8.60-8.80 (2H, m), 9.44 (1H, s).
ESI-MS (m/e): 467 [M+H]+

Example 10

5-(tetrahydrofuran-2-yl)-6-(4-(ethylsulfonyl)phenoxy)-2-pyrazin-2-yl-1H-benzimidazole Using 5-(6-(4-(ethylsulfonyl)phenoxy-2-pyrazin-2-yl-1H-benzimidazol-5-yl)tetrahydrofuran-2-ol obtained in Example 9, the entitled compound was obtained as a colorless solid in the same manner as in Example 7, or according to the method or according to a combination thereof with an ordinary method.
$^1$HNMR (CD$_3$OD) δ: 1.23 (3H, t, J=7.4 Hz), 1.70-1.88 (1H, m), 1.89-2.10 (2H, m), 2.23-2.39 (1H, m), 3.20 (2H, q, J=7.4 Hz), 3.84-3.93 (1H, m), 4.07-4.17 (1H, m), 5.07 (1H, t, J=6.8 Hz), 7.16 (2H, d, J=8.6 Hz), 7.21-7.44 (1H, m), 7.80-7.99 (1H, m), 7.88 (2H, d, J=8.6 Hz), 8.68 (1H, d, J=2.3 Hz), 8.75 (1H, s), 9.47 (1H, d, J=2.3 Hz)
ESI-MS (m/e): 451 [M+H]+

Example 11

5-(tetrahydrofuran-2-yl)-6-((6-(ethylsulfonyl)pyridin-3-yl)oxy)-2-pyridin-2-yl-1H-benzimidazole Using 5-carbaldehyde-6-((6-ethylsulfonyl)pyridin-3-yl)oxy)-2-pyridin-2-yl-1H-benzimidazole obtained in Reference Example 12, the entitled compound was obtained as a colorless solid in the same manner as in Example 6 and Example 7, or according to the method or according to a combination thereof with an ordinary method.
$^1$HNMR (CDCl$_3$) δ: 1.32 (3H, t, J=7.4 Hz), 1.96-2.07 (3H, m), 2.16-2.38 (1H, m), 3.40 (2H, q, J=7.4 Hz), 3.91 (1H, dd, J=7.8, 7.2 Hz), 4.07-4.14 (1H, m), 5.02-5.10 (1H, m), 7.12 and 7.42 (total 1H, each brs), 7.33 (1H, dd, J=8.6, 2.7 Hz), 7.39-7.42 (1H, m), 7.73 and 8.03 (total 1H, each brs), 7.88 (1H, td, J=7.6, 1.8 Hz), 8.01 (1H, d, J=8.4 Hz), 8.41 (1H, d, J=7.4 Hz), 8.52 (1H, s), 8.65 (1H, d, J=4.3 Hz)
ESI-MS (m/e): 451 [M+H]+

Example 12

5-(6-((6-(ethylsulfonyl)pyridin-3-yl)oxy)-2-pyridin-2-yl-1H-benzimidazol-5-yl)tetrahydrofuran-2-ol enantiomer A (Step 1)

Production of 1-(6-((6-(ethylsulfonyl)pyridin-3-yl)oxy)-2-pyridin-2-yl-1H-benzimidazol-5-yl)pent-4-ene-1-ol enantiomer A 1-(6-((6-(Ethylsulfonyl)pyridin-3-yl)oxy)-2-pyridin-2-yl-1H-benzimidazol-5-yl)pent-4-ene-1-ol (520 mg) obtained in Example 11 was optically resolved through an optical resolution column (CHIRALPAK OD 2 cmϕ×25 cmL, by Daicel Chemical Industry, mobile phase: hexane/ethanol=1/1, flow rate: 10 ml/min) to obtain its enantiomer A (retention time, 11.7 min) and enantiomer B (retention time, 15.0 min) both as a yellow solid.

(Step 2)

Production of 5-(6-((6-(ethylsulfonyl)pyridin-3-yl)oxy)-2-pyridin-2-yl-1H-benzimidazol-5-yl)tetrahydrofuran-2-ol enantiomer A Using 1-(6-((6-(ethylsulfonyl)pyridin-3-yl)oxy)-2-pyridin-2-yl-1H-benzimidazol-5-yl)pent-4-ene-1-ol enantiomer A obtained in (step 1), the entitled compound was obtained as a white solid in the same manner as in Example 6 (step 2), or according to the method or according to a combination thereof with an ordinary method.
$^1$HNMR (CD$_3$OD) δ: 1.24 (3H, t, J=7.4 Hz), 1.80-2.72 (4H, m), 3.39 (2H, q, J=7.4 Hz), 5.24 (1H×½, t, J=7.0 Hz), 5.38 (1H×½, t, J=6.8 Hz), 5.57 (1H×½, d, J=5.1 Hz), 5.68 (1H×½, d, J=5.1 Hz), 7.30-7.41 (1H, m), 7.49-7.53 (2H, m), 7.75-7.93 (OH, m), 7.97 (1H, t, J=7.1 Hz), 8.06 (1H, d, J=7.1 Hz), 8.28 (1H, d, J=7.1 Hz), 8.50-8.53 (1H, m), 8.73 (1H, d, J=4.7 Hz)
ESI-MS (m/e): 467 [M+H]+

Example 13

5-(tetrahydrofuran-2-yl)-6-((6-(ethylsulfonyl)pyridin-3-yl)oxy)-2-pyridin-2-yl-1H-benzimidazole enantiomer A (Step 1)

Production of 1-(6-(4-((6-(ethylsulfonyl)pyridin-3-yl)oxy)-2-pyridin-2-yl-1H-benzimidazol-5-yl)butane-1,4-diol enantiomer A Using 5-(6-((6-(ethylsulfonyl)pyridin-3-yl)oxy)-2-pyridin-2-yl-1H-benzimidazol-5-yl)tetrahydrofuran-2-ol enantiomer A obtained in Example 12, the entitled compound was obtained in the same manner as in Example 7 (step 1), or according to the method or according to a combination thereof with an ordinary method.
(Step 2)

Production of 5-(tetrahydrofuran-2-yl)-6-((6-(ethyl-sulfonyl)pyridin-3-yl)oxy)-2-pyridin-2-yl-1H-benzimidazole enantiomer A Triethylamine (0.07 ml) and methanesulfonyl chloride (0.023 ml) were added in that order to a tetrahydrofuran (3 ml) solution of 1-(6-(4-((6-(ethylsulfonyl)pyridin-3-yl)oxy)-2-pyridin-2-yl-1H-benzimidazol-5-yl)butane-1,4-diol enantiomer A (48 mg) obtained in (step 1), and the reaction liquid was stirred at room temperature for 4 hours. The reaction liquid was diluted with ethyl acetate, washed with aqueous saturated sodium bicarbonate and saturated saline water in that order, and dried with anhydrous magnesium sulfate. The solvent was evaporated away under reduced pressure, and 1,8-diazabicyclo[5.4.0]undec-7-ene (0.045 ml) was added to a chloroform (2 ml) solution of the resulting residue, and the reaction liquid was stirred at room temperature for 3 hours. The solvent was evaporated away under reduced pressure, and the resulting residue was purified through reversed-phase middle-pressure liquid chromatography (ODS-AS-360-CC (by YMC), mobile phase: water/acetonitrile/0.1% trifluoroacetic acid), and the resulting fraction was diluted with ethyl acetate, washed with aqueous saturated sodium bicarbonate and saturated saline water in that order, and dried with anhydrous sodium sulfate. The solvent was evaporated away under reduced pressure to obtain the entitled compound as a white solid.

Example 14

5-(6-((6-(ethylsulfonyl)pyridin-3-yl)oxy)-2-pyrazin-2-yl-1H-benzimidazol-5-yl)tetrahydrofuran-2-ol Using 5-carbaldehyde-6-((6-(ethylsulfonyl)pyridin-3-yl)oxy)-2-pyrazin-2-yl-1H-benzimidazole obtained in Reference Example 18, the entitled compound was obtained as a yellow solid in the same manner as in Example 6, or according to the method or according to a combination thereof with an ordinary method.
$^1$HNMR (CD$_3$OD) δ: 1.24-1.32 (3H, m), 1.75-2.50 (4H, m), 3.41 (2H, q, J=7.3 Hz), 5.26 (1H, t, J=7.4 Hz), 5.39 (1H, t, J=7.4 Hz), 5.59 (1H, d, J=6.4 Hz), 5.70 (1H, d, J=6.4 Hz), 7.24-7.55 (1H, m), 7.53-7.56 (1H, m), 7.80-8.30 (1H, m), 8.07 (1H, d, J=8.2 Hz), 8.53 (1H, s), 8.70 (1H, s), 8.77 (1H, s), 9.47 (1H, s)
ESI-MS (m/e): 468 [M+H]+

Example 15

5-(tetrahydrofuran-2-yl)-6-((6-(ethylsulfonyl)pyridin-3-yl)oxy)-2-pyrazin-2-yl-1H-benzimidazole Using 5-(6-((6-(ethylsulfonyl)pyridin-3-yl)oxy)-2-pyrazin-2-yl-1H-benzimidazol-5-yl)tetrahydrofuran-2-ol obtained in Example 14, the entitled compound was obtained as a colorless solid in the same manner as in Example 7, or according to the method or according to a combination thereof with an ordinary method.
$^1$HNMR (CD$_3$OD) δ: 1.26 (2H, t, J=7.4 Hz), 1.80-2.10 (3H, m), 2.32-2.38 (1H, m), 3.41 (2H, q, J=7.4 Hz), 3.90 (1H, q, J=7.3 Hz), 4.12 (1H, q, J=7.3 Hz), 5.10 (1H, t, J=7.3 Hz), 7.33-7.47 (1H, m), 7.55 (1H, dd, J=8.6, 2.7 Hz), 7.86-7.99 (1H, m), 8.08 (1H, d, J=8.6 Hz), 8.53 (1H, s), 8.71 (1H, d, J=2.7 Hz), 8.78 (1H, s), 9.48 (1H, s)
ESI-MS (m/e): 452 [M+H]+

Example 16

5-(tetrahydrofuran-2-yl)-6-(4-(methylsulfonyl)phenoxy)-2-pyridin-2-yl-1H-benzimidazole Using 5-carbaldehyde-6-(4-(methyl sulfonyl)phenoxy)-2-pyridin-2-yl-1H-benzimidazole obtained in Reference Example 11, the entitled compound was obtained as a colorless solid in the same manner as in Example 6 and Example 7, or according to the method or according to a combination thereof with an ordinary method.
$^1$HNMR (CDCl$_3$) δ: 1.88-2.05 (3H, m), 2.25-2.36 (1H, m), 3.06 (3H, s), 3.91 (1H, dt, J=7.8, 7.1 Hz), 4.06-4.16 (1H, m), 5.07 (1H, t, J=6.6 Hz), 7.07 (2H, d, J=8.8 Hz), 7.04-7.50 (2H, m), 7.62-8.10 (2H, m), 7.87 (2H, d, J=8.8 Hz), 8.41 (1H, d, J=8.2 Hz), 8.64 (1H, d, J=4.7 Hz)
ESI-MS (m/e): 436 [M+H]+

Example 17

5-(tetrahydrofuran-2-yl)-6-(6-(5-methyl-(1,2,4)oxadiazol-3-yl)-pyridin-3-yloxy)-2-pyridin-2-yl-1H-benzimidazole Using 5-carbaldehyde-6-(6-(5-methyl-(1,2,4)oxadiazol-3-yl)-pyridin-3-yloxy)-2-pyridin-2-yl-1H-benzimidazole obtained in Reference Example 14, the entitled compound was obtained as a colorless solid in the same manner as in Example 6 and Example 7, or according to the method or according to a combination thereof with an ordinary method.
$^1$HNMR (CDCl$_3$) δ: 1.93-2.05 (3H, m), 2.25-2.40 (1H, m), 2.68 (3H, s), 3.89-3.95 (1H, m), 4.10-4.16 (1H, m), 5.12-5.17 (1H, m), 7.20-8.00 (4H, m), 7.87 (1H, t, J=7.8 Hz), 8.02 (1H, J=8.8 Hz), 8.39 (1H, d, J=8.0 Hz), 8.61 (1H, d, J=2.5 Hz), 8.64 (1H, d, J=4.7 Hz.
ESI-MS (m/e): 441 [M+H]+

Example 18

5-(tetrahydrofuran-2-yl)-6-((6-(methylsulfonyl)pyridin-3-yl)oxy)-2-pyridin-2-yl-1H-benzimidazole Using 5-carbaldehyde-6-((6-(methylsulfonyl)pyridin-3-yl)oxy)-2-pyridin-2-yl-1H-benzimidazole obtained in Reference Example 13, the entitled compound was obtained as a colorless solid in the same manner as in Example 6 and Example 7, or according to the method or according to a combination thereof with an ordinary method.
$^1$HNMR (CDCl$_3$) δ: 1.95-2.05 (3H, m), 2.26-2.37 (1H, m), 3.23 (3H, s), 3.88-3.94 (1H, m), 4.08-4.14 (1H, m), 5.05 (1H, t, J=7.2 Hz), 7.20-8.00 (2H, m), 7.33 (1H, dd, J=8.6, 2.7 Hz), 7.41 (1H, dd, J=7.6, 4.9 Hz), 7.89 (1H, td, J=7.6, 1.4 Hz), 8.01 (1H, d, J=8.8 Hz), 8.40 (1H, d, J=8.0 Hz), 8.50 (1H, d, J=2.9 Hz), 8.65 (1H, d, J=3.9 Hz)
ESI-MS (m/e): 437 [M+H]+

Example 19

5-(4-methyltetrahydrofuran-2-yl)-6-(4-(methylsulfonyl)phenoxy)-2-pyridin-2-yl-1H-benzimidazole With cooling with ice, 2-methylallylmagnesium chloride (0.9 ml) was added to a tetrahydrofuran (2 ml) solution of 6-(4-(ethylsulfonyl)phenoxy)-2-pyridin-2-yl(2-(trimethylsilyl)ethoxy)methyl)-1H-benzimidazol-5-yl)methanol (140 mg) obtained in Reference Example 19, and the reaction liquid was stirred for 20 minutes with cooling with ice. The reaction liquid was diluted with ethyl acetate, washed with aqueous saturated ammonium chloride solution and saturated saline water in that order, and dried with anhydrous sodium sulfate. The solvent was evaporated away under reduced pressure, and the resulting residue was purified through silica gel column chromatography (developing solvent: chloroform/methanol=50/1) to obtain an alcohol compound. With cooling with ice, 1 M borane-dimethylsulfide complex/tetrahydrofuran solution (0.4 ml) was added to a tetrahydrofuran (1 ml) solution of the obtained alcohol compound (64 mg), and the reaction liquid was stirred at room temperature for 1 hour. Aqueous 5 N sodium hydroxide solution (0.5 ml) and aqueous 30% hydrogen peroxide (0.2 ml) were added to the reaction liquid, stirred for 40 minutes, then diluted with chloroform, washed with water and saturated saline water in that order and then dried with anhydrous sodium sulfate. The solvent was evaporated away under reduced pressure, and the resulting residue was dissolved in chloroform (1 ml), and zinc chloride (20 mg) was added to it, and the reaction liquid was stirred at 65° C. for 2 hours. The solvent was evaporated away under reduced pressure, and the resulting residue was purified through reversed-phase middle-pressure liquid chromatography (ODS-AS-360-CC (by YMC), mobile phase: water/acetonitrile/0.1% trifluoroacetic acid). The resulting fraction was diluted with ethyl acetate, washed with aqueous saturated sodium bicarbonate, and dried with anhydrous sodium sulfate. The solvent was evaporated away under reduced pressure to obtain the entitled compound as a white solid.

$^1$HNMR (CD$_3$OD) δ: 1.08 (3H, t, J=7.4 Hz), 1.28-1.41 (2H, m), 1.97-2.09 (1H, m), 2.45-2.54 (1H, m), 3.12-3.14 (3H, m), 3.34 (2H, q, J=7.4 Hz), 3.47-3.63 (1H, m), 4.02-4.33 (1H, m), 5.11-5.25 (1H, m), 7.17-7.19 (2H, m), 7.33 (1H, s), 7.54 (1H, dd, J=7.6, 3.9 Hz), 7.90-7.98 (1H, m), 7.95-7.97 (2H, m), 8.02 (1H, t, J=7.6 Hz), 8.30 (1H, d, J=7.6 Hz), 8.77 (1H, d, J=3.9 Hz)
ESI-MS (m/e): 450 [M+H]+

Example 20

5-(6-(4-(methylsulfonyl)phenoxy)-2-pyridin-2-yl-1H-benzimidazol-5-yl)dihydrofuran-2(3H)-one (Step 1)

Production of N-(3-fluoro-4-((methoxy(methyl)amino)carbonyl)phenyl)pyridine-2-carboxamide To a pyridine (80 ml) solution of 4-nitro-2-fluorobenzoic acid (10 g), which had been obtained according to the method described in Bioorganic & Medicinal Chemistry Letters, 15(2), 337-343, 2005, added were N,O-dimethylhydroxylamine monohydrochloride (5.3 g) and 1-(3-dimethylaminopropyl)-3-ethylcarbodiimide monohydrochloride (12 g), and the reaction liquid was stirred overnight at room temperature. The solvent was evaporated away under reduced pressure, water was added to the resulting residue, and the formed precipitate was taken out through filtration to obtain a crude product. Water (30 ml), ammonium chloride (15 g) and electrolytic iron powder (8 g) were added to a methanol (60 ml) solution of the crude product, and the reaction liquid was stirred for 3 hours with heating under reflux. Then, the precipitate was removed through filtration through Celite, and the solvent was evaporated away under reduced pressure. The resulting residue was purified through silica gel column chromatography (developing solvent: hexane/ethyl acetate=1/2); and to a pyridine (20 ml) solution of the obtained aniline compound (3.7 g), added were pyridine-2-carboxylic acid (2.6 g) and 1(3-dimethylaminopropyl)-3-ethylcarbodiimide monohydrochloride (4.7 g), and the reaction liquid was stirred at room temperature for 1 hour. The solvent was evaporated away under reduced pressure, the resulting residue was diluted with ethyl acetate, washed with water and saturated saline water in that order, and dried with anhydrous magnesium sulfate. The solvent was evaporated away under reduced pressure to obtain the entitled compound.
(Step 2)

Production of N-(3-fluoro-4-pent-4-enoylphenyl)pyridine-2-carboxamide

Using N-(3-fluoro-4-((methoxy(methyl)amino)carbonyl)phenyl)pyridine-2-carboxamide obtained in (step 1), the entitled compound was obtained in the same manner as in Example 6 (step 1), or according to the method or according to a combination thereof with an ordinary method.
(Step 3)

Production of N-(3-fluoro-4-(4-oxobutanoyl)phenyl)pyridine-2-carboxamide

To an acetonitrile (40 ml) solution of N-(3-fluoro-4-pent-4-enoylphenyl)pyridine-2-carboxamide (1.9 g) obtained in (step 2), added were water (24 ml), aqueous 1 M osmium tetroxide solution (3.5 ml) and sodium periodate (3.34 g), and the reaction liquid was stirred overnight at room temperature. The solvent was evaporated away under reduced pressure, then diluted with ethyl acetate, and washed with aqueous sodium sulfite solution. This was dried with anhydrous magnesium sulfate, the solvent was evaporated away under reduced pressure, and the resulting residue was purified through silica gel column chromatography (developing solvent: hexane/ethyl acetate=1/1) to obtain the entitled compound.
(Step 4)

Production of N-(3-fluoro-4-(5-oxotetrahydrofuran-2-yl)phenyl)pyridine-2-carboxamide To a t-butanol (24 ml) solution of N-(3-fluoro-4-(4-oxobutanoyl)phenyl)pyridine-2-carboxamide (660 mg) obtained in (step 3), added were acetonitrile (6 ml), water (6 ml), monosodium-dihydrogen phosphate dihydrate (520 mg), 2-methyl-2-butene (0.81 ml) and sodium chlorite (700 mg) in that order, and the reaction liquid was stirred overnight at room temperature. The solvent was evaporated away under reduced pressure, then 2 N hydrochloric acid was added to it, and the formed precipitate was taken out through filtration to obtain a carboxylic acid. To a methanol (10 ml) solution of the obtained carboxylic acid (660 mg), added were water (10 ml) and sodium borohydride (160 mg), and the reaction liquid was stirred at room temperature for 1 hour. The solvent was evaporated away under reduced pressure, then diluted with ethyl acetate, and washed with 0.1 N hydrochloric acid. This was dried with anhydrous magnesium sulfate, the solvent was evaporated away under reduced pressure, and toluene (15 ml) and p-toluenesulfonic acid monohydrate (80 mg) were added to the resulting residue, and the reaction liquid was stirred for 30 minutes with heating under reflux. The reaction liquid was diluted with ethyl acetate, washed with aqueous saturated sodium bicarbonate and saturated saline water in that order, and dried with anhydrous magnesium sulfate. The solvent was evaporated away under reduced pressure to obtain the entitled compound.
(Step 5)

Production of N-(5-fluoro-2-nitro-4-(5-oxotetrahydrofuran-2-yl)phenyl)pyridine-2-carboxamide Fuming nitric acid (3 ml) was added to N-(3-fluoro-4-(5-oxotetrahydrofuran-2-yl)phenyl)pyridine-2-carboxamide (600 mg) obtained in (step 4), and the reaction liquid was stirred at room temperature for 2 hours. With cooling with ice, aqueous saturated sodium bicarbonate was added to the reaction liquid to make it basic, and extracted with ethyl acetate. This was dried with anhydrous magnesium sulfate, then the solvent was evaporated away under reduced pressure, and the resulting residue was washed with chloroform/hexane mixed solvent to obtain the entitled compound.
(Step 6)

Production of 5-(6-(4-(methylsulfonyl)phenoxy)-2-pyridin-2-yl-1H-benzimidazol-5-yl)dihydrofuran-2(3H)-one To an N-methylpyrrolidinone (1 ml) solution of N-(5-fluoro-2-nitro-4-(5-oxotetrahydrofuran-2-yl)phenyl)pyridine-2-carboxamide (48 mg) obtained in (step 5), added were 4-methanesulfonyl-phenol (10 mg) and cesium carbonate (20 mg), and the reaction liquid was stirred at 100° C. for 1 hour. Tin(II) chloride dihydrate (100 mg) was added to it, and the reaction liquid was stirred at 100° C. for 5 hours. The reaction liquid was diluted with ethyl acetate, washed with water and saturated saline water in that order, and then dried with anhydrous sodium sulfate. The solvent was evaporated away under reduced pressure, and the resulting residue was purified through reversed-phase middle-pressure liquid chromatography (ODS-AS-360-CC (by YMC), mobile phase: water/acetonitrile/0.1% trifluoroacetic acid), and the resulting fraction was diluted with ethyl acetate, washed with aqueous saturated sodium bicarbonate and saturated saline water in that order, and dried with anhydrous sodium sulfate. The solvent was evaporated away under reduced pressure to obtain the entitled compound as a white solid.
$^1$HNMR (CDCl$_3$) δ: 2.10-2.38 (1H, m), 2.58-2.75 (3H, m), 3.07 (3H, s), 5.74 (1H, t, J=6.9 Hz), 7.07-7.49 (4H, m), 7.62-7.96 (4H, m), 8.38-8.44 (1H, m), 8.61-8.72 (1H, m)
ESI-MS (m/e): 450 [M+H]+

Example 21

5-(6-(4-(ethylsulfonyl)phenoxy)-2-pyridin-2-yl-1H-benzimidazol-5-yl)dihydrofuran-2(3H)-one Using 4-ethylsulfonylphenol, the entitled compound was obtained as a yellow foamy substance in the same manner as in Example 20 (step 6), or according to the method or according to a combination thereof with an ordinary method.
$^1$HNMR (CDCl$_3$) δ: 1.29 (3H, t, J=7.3 Hz), 1.91-2.43 (2H, m), 2.59-2.72 (2H, m), 3.12 (2H, q, J=7.3 Hz), 5.74-5.76 (1H, m), 7.12 (2H, d, J=9.0 Hz), 7.37-7.42 (1H, m), 7.45 (1H, s), 7.68 (1H, s), 7.81-7.88 (1H, m), 7.87 (3H, d, J=9.0 Hz), 8.34-8.41 (1H, m), 8.62-8.69 (1H, m)
ESI-MS (m/e): 464 [M+H]+

Example 22

5-(6-(4-(ethylsulfonyl)phenoxy)-2-pyridin-2-yl-1H-benzimidazol-5-yl)dihydrofuran-2(3H)-one enantiomer A and enantiomer B 5-(6-(4-(Ethylsulfonyl)phenoxy)-2-pyridin-2-yl-1H-benzimidazol-5-yl)dihydrofuran-2(3H)-one (5 mg) obtained in Example 21 was optically resolved through an optical resolution column (CHIRALPAK OD-H 2 cmφ×25 cmL, by Daicel Chemical Industry, mobile phase: hexane/ethanol=1/1, flow rate: 10 ml/min) to obtain its enantiomer A (retention time, 17.4 min) and enantiomer B (retention time, 19.1 min) both as a yellow foamy substance.

Example 23

5-(6-(4-(ethylsulfonyl)phenoxy)-2-pyrazin-2-yl-1H-benzimidazol-5-yl)dihydrofuran-2(3H)-one Sodium nitrite (5 mg) was added to a trifluoroacetic acid (1 ml) solution of 5-(6-(4-(ethylsulfonyl)phenoxy)-2-pyrazin-2-yl-1H-benzimidazol-5-yl)tetrahydrofuran-2-ol (3.3 mg) obtained in Example 9, and the reaction liquid was stirred at room temperature for 10 minutes. The solvent was evaporated away under reduced pressure, and the resulting residue was purified through reversed-phase middle-pressure liquid chromatography (ODS-AS-360-CC (by YMC), mobile phase: water/acetonitrile/0.1% trifluoroacetic acid), and the resulting fraction was diluted with ethyl acetate, washed with aqueous saturated sodium bicarbonate and saturated saline water in that order, and dried with anhydrous sodium sulfate. The solvent was evaporated away under reduced pressure to obtain the entitled compound as a yellow foamy substance.
$^1$HNMR(CDCl$_3$) δ: 1.20-1.42 (3H, m), 1.98-2.18 (1H, m), 2.18-2.44 (1H, m), 2.60-2.80 (2H, m), 3.18-3.32 (2H, m), 5.80-5.96 (1H,), 7.10-8.40 (6H, m), 8.68-8.88 (2H, m), 9.50 (1H, s)
ESI-MS (m/e): 465 [M+H]+

Example 24

5-(6-(((6-methylsulfonyl)pyridin-3-yl)oxy)-2-pyridin-2-yl-1H-benzimidazol-5-yl)dihydrofuran-2(3H)-one Using 6-methanesulfonyl-pyridin-3-ol, the entitled compound was obtained as a yellow foamy substance in the same manner as in Example 20 (step 6), or according to the method or according to a combination thereof with an ordinary method.
$^1$HNMR (CDCl$_3$) δ: 2.17-2.40 (1H, m), 2.60-2.76 (3H, m), 3.24 (3H, s), 5.71-5.78 (1H, m), 7.02-7.50 (3H, m), 7.65 and 7.98 (total 1H, each brs), 7.90 (1H, td, J=7.8, 1.5 Hz), 8.04 (1H, d, J=8.6 Hz), 8.41 (1H, d, J=7.6 Hz), 8.51 (1H, s), 8.65 (1H, s).
ESI-MS (m/e): 451 [M+H]+

Example 25

5-(6-(5-methyl-(1,2,4)oxadiazol-3-yl)-pyridin-3-yloxy)-2-pyridin-2-yl-1H-benzimidazol-5-yl)dihydrofuran-2(3H)-one Using 6-(6-(5-methyl-(1,2,4)oxadiazol-3-yl)-pyridin-3-ol, the entitled compound was obtained as a yellow foamy substance in the same manner as in Example 20 (step 6), or according to the method or according to a combination thereof with an ordinary method.
¹HNMR (CDCl₃) δ: 2.12-2.38 (1H, m), 2.60-2.80 (6H, m), 5.82 (1H, t, J=7.2 Hz), 7.06 and 7.45 (total 1H, each s), 7.36 (1H, dd, J=8.6, 2.7 Hz), 7.40 (1H, t, J=6.0 Hz), 7.62 and 7.97 (total 1H, each s), 7.88 (1H, t, J=7.2 Hz), 8.06 (1H, d, J=8.6 Hz), 8.38-8.48 (1H, m), 8.57-8.70 (2H, m)
ESI-MS (m/e): 455 [M+H]+

Example 26

5-(6-((6-(ethylsulfonyl)pyridin-3-yl)oxy)-2-pyridin-2-yl-1H-benzimidazol-5-yl)dihydrofuran-2(3H)-one Using 6-ethanesulfonyl-pyridin-3-ol, the entitled compound was obtained as a yellow foamy substance in the same manner as in Example 20 (step 6), or according to the method or according to a combination thereof with an ordinary method. ¹HNMR (CDCl₃) δ: 1.33 (3H, t, J=7.4 Hz), 2.15-2.42 (1H, m), 2.60-2.78 (3H, m), 3.41 (2H, q, J=7.4 Hz), 5.75 (1H, t, J=7.4 Hz), 7.11 and 7.46 (total 1H, each s), 7.39-7.45 (2H, m), 7.65 and 7.97 (total 1H, each s), 7.90 (1H, t, J=7.8 Hz), 8.05 (1H, dd, J=8.4, 4.4 Hz), 8.39 and 8.43 (total 1H, each d, J=7.8 Hz), 8.51 and 8.54 (total 1H, each d, J=2.6 Hz), 8.64 and 8.67 (total 1H, each d, J=4.4 Hz)
ESI-MS (m/e): 465 [M+H]+

Example 27

5-(6-((6-(ethylsulfonyl)pyridin-3-yl)oxy)-2-pyridin-2-yl-1H-benzimidazol-5-yl)dihydrofuran-2(3H)-one enantiomer A and enantiomer B 5-(6-((6-(Ethylsulfonyl)pyridin-3-yl)oxy)-2-pyridin-2-yl-1H-benzimidazol-5-yl)dihydrofuran-2(3H)-one (41 mg) obtained in Example 26 was optically resolved through an optical resolution column (CHIRALPAK OD-H 2 cmφ×25 cmL, by Daicel Chemical Industry, mobile phase: hexane/ethanol=1/1, flow rate: 10 ml/min) to obtain its enantiomer A (retention time, 29.0 min) and enantiomer B (retention time, 35.5 min) both as a yellow foamy substance.

Example 28

5-(6-((6-ethylsulfonyl)pyridin-3-yl)oxy)-2-pyrazin-2-yl-1H-benzimidazol-5-yl)dihydrofuran-2(3H)-one Using 5-(6-((6-(ethylsulfonyl)pyridin-3-yl)oxy)-2-pyrazin-2-yl-1H-benzimidazol-5-yl)tetrahydrofuran-2-ol obtained in Example 14, the entitled compound was obtained as a yellow foamy substance in the same manner as in Example 23, or according to the method or according to a combination thereof with an ordinary method.
¹HNMR (CD₃OD) δ: 1.28 (3H, t, J=7.4 Hz), 2.36-2.37 (1H, m), 2.70-2.75 (3H, m), 3.42 (2H, q, J=7.4 Hz), 5.87 (1H, t, J=7.6 Hz), 7.47-7.53 (1H, m), 7.62 (1H, dd, J=8.6, 4.3 Hz), 7.89-7.92 (1H, m), 8.10 (1H, d, J=8.6 Hz), 8.58 (1H, s), 8.74 (1H, t, J=4.3 Hz), 8.80 (1H, s), 9.51 (1H, s)
ESI-MS (m/e): 466 [M+H]+

Example 29

5-(tetrahydro-2-thienyl)-6-(4-(ethylsulfonyl)phenoxy)-2-pyridin-2-yl-1H-benzimidazole and 5-(1,2-dithian-3-yl)-6-(4-(ethylsulfonyl)phenoxy)-2-pyridin-2-yl-1H-benzimidazole To a chloroform (2 ml) solution of 1-(6-(4-(ethylsulfonyl)phenoxy)-2-pyridin-2-yl-1H-benzimidazol-5-yl)butane-1,4-diol (58 mg) obtained in Example 7 (step 1), added were triethylamine (0.052 ml) and methanesulfonyl chloride (0.032 ml) in that order, and the reaction liquid was stirred at room temperature for 5 minutes. The reaction liquid was diluted with ethyl acetate, washed with aqueous saturated sodium bicarbonate and saturated saline water in that order, and dried with anhydrous sodium sulfate. The solvent was evaporated away under reduced pressure, and to an acetone (3 ml) solution of the resulting residue, added was potassium O-ethyldithiocarbonate (70 mg), and the reaction liquid was stirred at 50° C. for 15 minutes. The reaction liquid was diluted with ethyl acetate, washed with water and saturated saline water in that order, and dried with anhydrous sodium sulfate. To a methanol (3 ml) solution of the obtained crude product, added was 25% sodium methoxide solution (0.03 ml), and the reaction liquid was stirred at room temperature for 20 minutes. Then, p-toluenesulfonic acid monohydrate (15 mg) was added to it, and the solvent was evaporated away under reduced pressure. The resulting residue was dissolved in toluene (1 ml), and the reaction liquid was stirred overnight at 70° C. The solvent was evaporated away under reduced pressure, and the reaction mixture was purified through reversed-phase middle-pressure liquid chromatography (ODS-AS-360-CC (by YMC), mobile phase: water/acetonitrile/0.1% trifluoroacetic acid), and the resulting fraction was diluted with ethyl acetate, washed with aqueous saturated sodium bicarbonate and saturated saline water in that order, and dried with anhydrous sodium sulfate. The solvent was evaporated away under reduced pressure to obtain 5-(tetrahydro-2-thienyl)-6-(4-(ethylsulfonyl)phenoxy)-2-pyridin-2-yl-1H-benzimidazole (yellow foamy substance), and 5-(1,2-dithian-3-yl)-6-(4-(ethylsulfonyl)phenoxy)-2-pyridin-2-yl-1H-benzimidazole (pale brown solid).

5-(tetrahydro-2-thienyl)-6-(4-(ethylsulfonyl)phenoxy)-2-pyridin-2-yl-1H-benzimidazole ¹HNMR (CD₃OD) δ: 1.23 (3H, t, J=7.4 Hz), 1.94-2.08 (2H, m), 2.22-2.37 (2H, m), 2.92-2.95 (1H, m), 3.12-3.13 (1H, m), 3.20 (2H, q, J=7.4 Hz), 4.77 (1H, t, J=7.0 Hz), 7.15 (2H, d, J=8.6 Hz), 7.29 (1H, brs), 7.48 (1H, dd, J=7.8, 4.7 Hz), 7.88 (2H, d, J=8.6 Hz), 7.97 (1H, t, J=7.8 Hz), 8.04 (1H, brs), 8.27 (1H, d, J=7.8 Hz), 8.73 (1H, d, J=4.7 Hz)
ESI-MS (m/e): 466 [M+H]+

5-(1,2-dithian-3-yl)-6-(4-(ethylsulfonyl)phenoxy)-2-pyridin-2-yl-1H-benzimidazole ¹HNMR (CD₃OD) δ: 1.23 (3H, t, J=7.6 Hz), 1.86-1.93 (1H, m), 2.16-2.18 (1H, m), 2.32-2.35 (2H, m), 2.65 (3H, s), 2.71-2.73 (1H, m), 2.95-2.98 (1H, m), 3.20 (2H, q, J=7.6 Hz), 4.36-4.38 (1H, m), 7.18 (2H, d, J=8.6 Hz), 7.29-7.36 (1H, m), 7.47-7.49 (1H, m), 7.71-7.81 (1H, m), 7.88 (2H, d, J=8.6 Hz), 7.95-7.97 (1H, m), 8.26-8.28 (1H, m), 8.73 (1H, brs)
ESI-MS (m/e): 498 [M+H]+
Of the compounds obtained in the above Example 29, the method for producing 5-(tetrahydro-2-thienyl)-6-(4-(ethylsulfonyl)phenoxy)-2-pyridin-2-yl-1H-benzimidazole is Example 29-1.

Example 30

5-(1-oxidotetrahydro-2-thienyl)-6-(4-(ethylsulfonyl)phenoxy)-2-pyridin-2-yl-1H-benzimidazole and 5-(1,1-dioxidotetrahydro-2-thienyl)-6-(4-(ethylsulfonyl)phenoxy)-2-pyridin-2-yl-1H-benzimidazole To a methanol (1 ml) solution of 5-(tetrahydro-2-thienyl)-6-(4-(ethylsulfonyl)phenoxy)-2-pyridin-2-yl-1H-benzimidazole (3.5 mg) obtained in Example 29, added were water (0.5 ml) and OXONE (6 mg), and the reaction liquid was stirred at room temperature for 1 hour. Triethylamine (0.1 ml) was added to the reaction liquid, and the solvent was evaporated away under reduced pressure. The reaction mixture was purified through reversed-phase middle-pressure liquid chromatography (ODS-AS-360-CC (by YMC), mobile phase: water/acetonitrile/0.1% trifluoroacetic acid), and the resulting fraction was diluted with ethyl acetate, washed with aqueous saturated sodium bicarbonate and saturated saline water in that order, and dried with anhydrous sodium sulfate. The solvent was evaporated away under reduced pressure to obtain 5-(1-oxidotetrahydro-2-thienyl)-6-(4-(ethylsulfonyl) phenoxy)-2-pyridin-2-yl-1H-benzimidazole and 5-(1,1-dioxidotetrahydro-2-thienyl)-6-(4-(ethylsulfonyl)phenoxy)-2-pyridin-2-yl-1H-benzimidazole both as a colorless solid.

5-(1-oxidotetrahydro-2-thienyl)-6-(4-(ethylsulfonyl) phenoxy)-2-pyridin-2-yl-1H-benzimidazole $^1$HNMR (CD$_3$OD) δ: 0.76-1.56 (3H, m), 1.80-3.00 (6H, m), 3.20-3.40 (2H, m), 4.80-5.50 (1H, m), 7.20-7.80 (4H, m), 7.90-8.10 (4H, m), 8.26-8.40 (1H, m), 8.72-8.84 (1H, m)
ESI-MS (m/e): 483 [M+H]+

5-(1,1-dioxidotetrahydro-2-thienyl)-6-(4-(ethylsulfonyl)phenoxy)-2-pyridin-2-yl-1H-benzimidazole $^1$HNMR (CD$_3$OD) δ: 1.101-1.60 (3H, m), 1.90-2.50 (4H, m), 2.54-2.80 (2H, m), 3.14-3.42 (2H, m), 4.60-5.10 (1H, m), 7.18-7.68 (4H, m), 7.80-8.10 (4H, m), 8.30-8.40 (1H, m), 8.70-8.80 (1H, m)
ESI-MS (m/e): 499 [M+H]+

Example 31

5-(6-(4-(ethylsulfonyl)phenoxy)-2-pyridin-2-yl-1H-benzimidazol-5-yl)-3-methyl-1,3-oxazolidine-2,4-dione (Step 1)

Production of (6-(4-(ethylsulfonyl)phenoxy)-2-pyridin-2-yl-1H-benzimidazol-5-yl)((trimethylsilyl)oxy)acetonitrile trimethylsilylnitrile (0.3 ml) and zinc iodide (15 mg) were added to 5-carbaldehyde-6-(4-(ethylsulfonyl)phenoxy)-2-pyridin-2-yl-1H-benzimidazole (50 mg) obtained in Reference Example 19, and the reaction liquid was stirred at room temperature for 2 hours, then diluted with ethyl acetate, washed with aqueous saturated sodium bicarbonate and saturated saline water in that order, and dried with anhydrous sodium sulfate. The solvent was evaporated away under reduced pressure to obtain the entitled compound.
(Step 2)

Production of methyl (6-(4-(ethylsulfonyl)phenoxy)-2-pyridin-2-yl-1H-benzimidazol-5-yl)(hydroxy)acetate 10% hydrochloric acid/methanol (3 ml) was added to (6-(4-(ethylsulfonyl)phenoxy)-2-pyridin-2-yl-1H-benzimidazol-5-yl)((trimethylsilyl)oxy)acetonitrile (65 mg) obtained in (step 1), and stirred at 70° C. for 4 hours. The solvent was evaporated away under reduced pressure, and the reaction mixture was purified through reversed-phase middle-pressure liquid chromatography (ODS-AS-360-CC (by YMC), mobile phase: water/acetonitrile/0.1% trifluoroacetic acid), and the resulting fraction was diluted with ethyl acetate, washed with aqueous saturated sodium bicarbonate and saturated saline water in that order, and dried with anhydrous sodium sulfate. The solvent was evaporated away under reduced pressure to obtain the entitled compound.
(Step 3)

Production of 5-(6-(4-(ethylsulfonyl)phenoxy)-2-pyridin-2-yl-1H-benzimidazol-5-yl)-3-methyl-1,3-oxazolidine-2,4-dione 1 N methylamine/methanol solution (2 ml) was added to methyl (6-(4-(ethylsulfonyl)phenoxy)-2-pyridin-2-yl-1H-benzimidazol-5-yl)(hydroxy)acetate (14 mg) obtained in (step 2), and the reaction liquid was stirred at 50° C. for 3 hours. The solvent was evaporated away under reduced pressure, and to a tetrahydrofuran (2 ml) solution of the resulting residue, added were 1,1'-carbonyldiimidazole (2.5 mg) and triethylamine (0.01 ml), and the reaction liquid was stirred at 70° C. for 2 hours. then, potassium t-butoxide (3 mg) was added to it, and the reaction liquid was stirred at 70° C. for 5 minutes. The reaction mixture was purified through reversed-phase middle-pressure liquid chromatography (ODS-AS-360-CC (by YMC), mobile phase: water/acetonitrile/0.1% trifluoroacetic acid), and the resulting fraction was diluted with ethyl acetate, washed with aqueous saturated sodium bicarbonate and saturated saline water in that order, and dried with anhydrous sodium sulfate. The solvent was evaporated away under reduced pressure to obtain the entitled compound as a yellow solid.
$^1$HNMR (CD$_3$OD) δ: 0.80-1.80 (3H, m), 2.90-3.70 (3H, m), 6.12 (1H, s), 6.90-9.10 (10H, m)
ESI-MS (m/e): 493 [M+H]+

Example 32

5-(6-((6-(ethylsulfonyl)pyridin-3-yl)oxy)-2-pyridin-2-yl-1H-benzimidazol-5-yl)-3-methyl-1,3-oxazolidine-2,4-dione Using 5-carbaldehyde-6-((6-(ethylsulfonyl)pyridin-3-yl)oxy)-2-pyridin-2-yl-1H-benzimidazole obtained in Reference Example 13, the entitled compound was obtained as a colorless solid in the same manner as in Example 31, or according to the method or according to a combination thereof with an ordinary method.
$^1$HNMR (CD$_3$OD) δ: 1.32 (3H, t, J=7.4 Hz), 3.12 (3H, s), 3.51 (2H, q, J=7.4 Hz), 6.78-6.86 (1H, m), 7.00-7.20 (1H, m), 7.43-7.45 (1H, m), 7.89-8.18 (2H, m), 8.27 (1H, d, J=8.2 Hz), 8.48 (1H, dd, J=8.2, 2.3 Hz), 8.67 (1H, d, J=3.9 Hz), 9.10 (1H, d, J=2.3 Hz)
ESI-MS (m/e): 494 [M+H]+

Example 33

5-(6-(4-(ethylsulfonyl)phenoxy)-2-pyridin-2-yl-1H-benzimidazol-5-yl)-1,3-oxazolidine-2,4-dione (Step 1)

Production of 2-(6-(4-(ethylsulfonyl)phenoxy)-2-pyridin-2-yl-1H-benzimidazol-5-yl)-2-hydroxyacetamide 80% sulfuric acid (0.2 ml) was added to (6-(4-(ethylsulfonyl)phenoxy)-2-pyridin-2-yl-1H-benzimidazol-5-yl)((trimethylsilyl(oxy)acetonitrile (25 mg) obtained in Example 31 (step 1), and the reaction liquid was stirred at room temperature for 3 hours. The reaction mixture was purified through reversed-phase middle-pressure liquid chromatography (ODS-AS-360-CC (by YMC), mobile phase: water/acetonitrile/0.1% trifluoroacetic acid), and the resulting fraction was diluted with ethyl acetate, washed with aqueous saturated sodium bicarbonate and saturated saline water in that order, and dried with anhydrous sodium sulfate. The solvent was evaporated away under reduced pressure to obtain the entitled compound.

(Step 2)

Production of 5-(6-(4-(ethylsulfonyl)phenoxy)-2-pyridin-2-yl-1H-benzimidazol-5-yl)-1,3-oxazolidine-2,4-dione Using 2-(6-(4-(ethylsulfonyl)phenoxy)-2-pyridin-2-yl-1H-benzimidazol-5-yl)-2-hydroxyacetamide obtained in (step 1), the entitled compound was obtained as a pale yellow solid in the same manner as in Example 31 (step 3), or according to the method or according to a combination thereof with an ordinary method.

$^1$HNMR (CD$_3$OD) δ: 0.60-1.90 (3H, m), 3.00-3.60 (2H, m), 6.00-6.20 (1H, m), 7.00-8.10 (8H, m), 8.30-8.42 (1H, m), 8.70-8.90 (1H, m)

ESI-MS (m/e): 479 [M+H]+

Example 34

5-(6-(4-(ethylsulfonyl)phenoxy)-2-pyridin-2-yl-1H-benzimidazol-5-yl)-2,2-dimethyl-1,3-dioxolan-4-one (Step 1)

Production of (6-(4-(ethylsulfonyl)phenoxy)-2-pyridin-2-yl-1H-benzimidazol-5-yl)(hydroxy)acetic acid Sodium borohydride (15 mg) was added to a methanol (1 ml) solution of methyl (6-(4-(ethylsulfonyl)phenoxy)-2-pyridin-2-yl-1H-benzimidazol-5-yl)(hydroxy)acetate (21 mg) obtained in Example 31 (step 2), and the reaction liquid was stirred overnight at 60° C. The solvent was evaporated away under reduced pressure, and the reaction mixture was purified through reversed-phase middle-pressure liquid chromatography (ODS-AS-360-CC (by YMC), mobile phase: water/acetonitrile/0.1% trifluoroacetic acid), and the resulting fraction was diluted with ethyl acetate, washed with aqueous saturated sodium bicarbonate and saturated saline water in that order, and dried with anhydrous sodium sulfate. The solvent was evaporated away under reduced pressure to obtain the entitled compound.

(Step 2)

Production of 5-(6-(4-(ethylsulfonyl)phenoxy)-2-pyridin-2-yl-1H-benzimidazol-5-yl)-2,2-dimethyl-1,3-dioxolan-4-one (6-(4-(Ethylsulfonyl)phenoxy)-2-pyridin-2-yl-1H-benzimidazol-5-yl)(hydroxy)acetic acid (2.9 mg) obtained in (step 1) was dissolved in 2,2-dimethoxypropane (1 ml), and the reaction liquid was stirred overnight at 75° C. The solvent was evaporated away under reduced pressure to obtain the entitled compound as a colorless solid. $^1$HNMR (CD$_3$OD) δ: 1.26 (3H, t, J=7.4 Hz), 1.53 (3H, s), 1.67 (3H, s), 3.24 (2H, q, J=7.4 Hz), 5.82 (1H, s), 7.28 (2H, d, J=8.6 Hz), 7.33 (1H, s), 7.57 (1H, dd, J=8.2, 4.2 Hz), 7.94 (1H, s), 7.95 (2H, d, J=8.6 Hz), 8.04 (1H, t, J=8.2 Hz), 8.31 (1H, d, J=8.2 Hz), 8.79 (1H, d, J=4.7 Hz)

ESI-MS (m/e): 494 [M+H]+

Example 35

4-(6-(4-(ethylsulfonyl)phenoxy)-2-pyridin-2-yl-1H-benzimidazol-5-yl)-1,3-dioxolan-2-one (Step 1)

Production of 1-(6-(4-(ethylsulfonyl)phenoxy)-2-pyridin-2-yl-1H-benzimidazol-5-yl)ethane-1,2-diol To a tetrahydrofuran (1.5 ml) solution of methyl (6-(4-(ethylsulfonyl)phenoxy)-2-pyridin-2-yl-1H-benzimidazol-5-yl)(hydroxy)acetate (30 mg) obtained in Example 31 (step 2), added was lithiumaluminium hydride (10 mg), and the reaction liquid was stirred at 0° C. for 10 minutes. Sodium sulfate 10-hydrate was added to the reaction liquid, and stirred overnight at room temperature. Then, the residue was removed through filtration through Celite, and the solvent was evaporated away under reduced pressure. The resulting residue was purified through reversed-phase middle-pressure liquid chromatography (ODS-AS-360-CC (by YMC), mobile phase: water/acetonitrile/0.1% trifluoroacetic acid), and the resulting fraction was diluted with ethyl acetate, washed with aqueous saturated sodium bicarbonate and saturated saline water in that order, and dried with anhydrous sodium sulfate. The solvent was evaporated away under reduced pressure to obtain the entitled compound.

(Step 2)

Production of 4-(6-(4-(ethylsulfonyl)phenoxy)-2-pyridin-2-yl-1H-benzimidazol-5-yl)-1,3-dioxolan-2-one To a tetrahydrofuran (2 ml) solution of 1-(6-(4-(ethylsulfonyl)phenoxy)-2-pyridin-2-yl-1H-benzimidazol-5-yl)ethane-1,2-diol (5.4 mg) obtained in (step 1), added was 1,1'-carbonyldiimidazole (5 mg), and the reaction liquid was stirred overnight at 60° C. The reaction mixture was purified through reversed-phase middle-pressure liquid chromatography (ODS-AS-360-CC (by YMC), mobile phase: water/acetonitrile/0.1% trifluoroacetic acid), and the resulting fraction was diluted with ethyl acetate, washed with aqueous saturated sodium bicarbonate and saturated saline water in that order, and dried with anhydrous sodium sulfate. The solvent was evaporated away under reduced pressure to obtain the entitled compound as a colorless solid.

$^1$HNMR (CD$_3$OD) δ: 1.26 (3H, t, J=7.4 Hz), 3.24 (2H, q, J=7.4 Hz), 4.55-4.56 (1H, m), 4.62-4.65 (1H, m), 6.04-6.06 (1H, m), 7.29 (2H, d, J=8.6 Hz), 7.34-7.50 (1H, m), 7.52-7.54 (1H, m), 7.76-8.00 (1H, m), 7.95 (2H, d, J=8.6 Hz), 7.98-8.04 (1H, m), 8.31-8.33 (1H, m), 8.74-8.78 (1H, m)

ESI-MS (m/e): 466 [M+H]+

Example 36

3-(6-(4-(ethylsulfonyl)phenoxy)-2-pyridin-2-yl-1H-benzimidazol-5-yl)dihydrofuran-2(3H)-one (Step 1)

Production of (6-(4-(ethylsulfonyl)phenoxy)-2-pyridin-2-yl-((2-(trimethylsilyl)ethoxy)methyl)-1H-benzimidazol-5-yl)acetonitrile Triethylamine (0.49 ml) and methanesulfonyl chloride (0.27 ml) were added in that order to a tetrahydrofuran (20 ml) solution of (6-(4-(ethylsulfonyl)phenoxy)-2-pyridin-2-yl-(2-(trimethylsilyl)ethoxy)methyl)-1H-benzimidazol-5-yl) methanol (930 mg) obtained in Reference Example 19, and the reaction liquid was stirred for 20 minutes with cooling with ice. The reaction liquid was diluted with ethyl acetate, washed with aqueous saturated sodium bicarbonate and saturated saline water in that order, and dried with anhydrous sodium sulfate. The solvent was evaporated away under reduced pressure, and to a dimethylformamide (10 ml) solution of the resulting residue, added was sodium cyanide (270 mg), and the reaction liquid was stirred at room temperature for 4 hours. The reaction liquid was diluted with ethyl acetate, washed with water and saturated saline water in that order, and dried with anhydrous sodium sulfate. The solvent was evaporated away under reduced pressure, and the resulting residue was purified through silica gel column chromatography (developing solvent: chloroform/methanol=20/1) to obtain the entitled compound.

(Step 2)

Production of methyl (6-(4-(ethylsulfonyl)phenoxy)-2-pyridin-2-yl((2-(trimethylsilyl)ethoxy)methyl-1H-benzimidazol-5-yl)acetate Methanol (2 ml) and aqueous 5 N sodium hydroxide solution (0.2 ml) were added to a tetrahydrofuran (1 ml) solution of (6-(4-(ethylsulfonyl)phenoxy)-2-pyridin-2-yl-((2-(trimethylsilyl)ethoxy)methyl-1H-benzimidazol-5-yl)acetonitrile (50 mg) obtained in (step 1), and the reaction liquid was stirred overnight at 100° C. Aqueous 10% citric acid was added to the reaction liquid, extracted with chloroform, and dried with anhydrous magnesium sulfate. The solvent was evaporated away under reduced pressure, and to a tetrahydrofuran (0.5 ml) solution of the resulting crude product (28 mg), added were methanol (0.5 ml) and trimethylsilyldiazomethane (2 M ether solution, 0.08 ml), and the reaction liquid was stirred at room temperature for 30 minutes. The reaction liquid was diluted with ethyl acetate, washed with aqueous saturated sodium bicarbonate and saturated saline water, and dried with anhydrous sodium sulfate. The solvent was evaporated away under reduced pressure, and the resulting residue was purified through partitioning thin-layer chromatography (Kieselgel™ 60F254, Art 5744 by Merck, chloroform/methanol=20/1) to obtain the entitled compound.

(Step 3)

Production of methyl 2-(6-(4-(ethylsulfonyl)phenoxy)-2-pyridin-2-yl-(trimethylsilyl)ethoxy)methyl)-1H-benzimidazol-5-yl)penten-4-oate To a dimethylformamide (1 ml) solution of methyl (6-(4-(ethylsulfonyl)phenoxy)-2-pyridin-2-yl((2-(trimethylsilyl)ethoxy)methyl-1H-benzimidazol-5-yl)acetate (94 mg) obtained in (step 2), added were sodium hydride (40% liquid paraffin added, 7.4 mg) and allyl bromide (0.015 ml), and the reaction liquid was stirred for 20 minutes with cooling with ice. The reaction liquid was diluted with ethyl acetate, washed with aqueous saturated ammonium chloride solution and saturated saline water in that order, and dried with anhydrous sodium sulfate. The solvent was evaporated away under reduced pressure, and the resulting residue was purified through silica gel column chromatography (developing solvent: chloroform/methanol) to obtain the entitled compound.

(Step 4)

Production of 3-(6-(4-(ethylsulfonyl)phenoxy)-2-pyridin-2-yl-1H-benzimidazol-5-yl)dihydrofuran-2(3H)-one To a tetrahydrofuran (1 ml) solution of methyl 2-(6-(4-(ethylsulfonyl)phenoxy)-2-pyridin-2-yl-((2-(trimethylsilyl) ethoxy)methyl)-1H-benzimidazol-5-yl)penten-4-oate (40 mg) obtained in (step 3), added were aqueous 0.1 M osmium tetroxide solution (0.0065 ml), water (0.4 ml) and sodium periodate (42 mg), and the reaction liquid was stirred at room temperature for 3 hours. Sodium sulfite was added to the reaction liquid, and stirred for 30 minutes, and the reaction liquid was diluted with ethyl acetate, washed with water and saturated saline water in that order, and dried with anhydrous sodium sulfate. The solvent was evaporated away under reduced pressure, and to a methanol (1 ml) solution of the resulting crude product (8 mg), added was sodium borohydride (10 mg), and the reaction liquid was stirred overnight at room temperature. The reaction liquid was diluted with ethyl acetate, washed with water and saturated saline water in that order, and dried with anhydrous sodium sulfate. The solvent was evaporated away under reduced pressure, and the resulting residue was purified through partitioning thin-layer chromatography (Kieselgel™ 60F254, Art 5744 by Merck, chloroform/methanol=20/1) to obtain a lactone compound. The obtained lactone compound was dissolved in trifluoroacetic acid (1 ml), and water (0.1 ml) was added to it, and the reaction liquid was stirred at room temperature for 1 hour. The solvent was evaporated away under reduced pressure, and the resulting residue was purified through partitioning thin-layer chromatography (Kieselgel™ 60F254, Art 5744 by Merck, chloroform/methanol=20/1) to obtain the entitled compound as a colorless solid.

$^1$HNMR (CDCl$_3$) δ: 1.31 (3H, t, J=7.4 Hz), 2.40-2.73 (2H, m), 3.13 (2H, q, J=7.4 Hz), 4.04-4.10 (1H, m), 4.32-4.38 (1H, m), 4.47-4.52 (1H, m), 7.09 (1H, s), 7.17-7.23 (2H, m), 7.38-7.45 (1H, m), 7.43 (1H×½, s), 7.52 (1H×½, s), 7.81 (1H×½, s), 7.85-7.90 (3H, m), 8.35-8.40 (1H, m), 8.62-8.67 (1H, m), 10.47 (1H×½, brs), 10.56 (1H×½, brs)

ESI-MS (m/e): 464 [M+H]+

Example 37

3-(6-((6-(ethylsulfonyl)pyridin-3-yl)oxy)-2-pyridin-2-yl-1H-benzimidazol-5-yl)dihydrofuran-2(3H)-one Using 5-carbaldehyde-6-((6-(ethylsulfonyl)pyridin-3-yl)oxy)-2-pyridin-2-yl-1H-benzimidazole obtained in Reference Example 13, the entitled compound was obtained as a yellow solid in the same manner as in Example 36, or according to the method or according to a combination thereof with an ordinary method.

$^1$HNMR (CD$_3$OD) δ: 1.25 (2H, t, J=7.4 Hz), 3.07-3.33 (2H, m), 3.42 (2H, q, J=7.4 Hz), 4.03-4.13 (1H, m), 4.29-4.36 (1H, m), 4.46-4.57 (1H, m), 7.12 (1H, s), 7.43 (1H, s), 7.54 (1H, dd, J=7.6, 4.9 Hz), 8.01 (1H, t, J=7.6 Hz), 8.09 (1H, d, J=7.6 Hz), 8.21 (1H, d, J=7.6 Hz), 8.26 (1H, dd, J=7.6, 2.2 Hz), 8.76 (1H, d, J=4.9 Hz), 8.85 (1H, d, J=2.2 Hz).

ESI-MS (m/e): 465 [M+H]+

Example 38

5-(tetrahydrofuran-3-yl)-6-((6-(ethylsulfonyl)pyridin-3-yl)oxy)-2-pyridin-2-yl-1H-benzimidazol Using 3-(6-((6-(ethylsulfonyl)pyridin-3-yl)oxy)-2-pyridin-2-yl-1H-benzimidazol-5-yl)dihydrofuran-2(3H)-one obtained in Reference Example 37, the entitled compound was obtained as a yellow foamy substance in the same manner as in Example 35 (step 1) and Example 7, or according to the method or according to a combination thereof with an ordinary method.

$^1$HNMR (CD$_3$OD) δ: 1.10-1.50 (3H, m), 1.58-2.42 (2H, m), 3.10-3.60 (3H, m), 3.80-4.30 (2H, m), 4.70-5.20 (2H, m), 7.42 (1H, m), 7.52-7.62 (1H, m), 7.94 (1H, s), 8.00-8.07 (1H, m), 8.11 (1H, d, J=8.8 Hz), 8.29 (1H, d, J=8.8 Hz), 8.33 (1H, d, J=8.8 Hz), 8.52-8.60 (2H, m), 8.80 (1H, d, J=4.7 Hz), 9.20 (1H, d, J=2.2 Hz)
ESI-MS (m/e): 451 [M+H]+

Example 39

5-(6-((6-cyanopyridin-3-yl)oxy)-2-pyridin-2-yl-1H-benzimidazol-5-yl)dihydrofuran-2(3H)-one Using 6-cyanopyridin-3-ol, the entitled compound was obtained as a yellow foamy substance in the same manner as in Example 20 (step 5), or according to the method or according to a combination thereof with an ordinary method.
$^1$HNMR (CD$_3$OD) δ: 2.22-2.40 (1H, m), 2.61-2.78 (3H, m), 5.78-5.85 (1H, m), 7.30-7.54 (3H, m), 7.76-7.93 (1H, m), 7.84 (1H, d, J=8.4 Hz), 7.98 (1H, t, J=8.4 Hz), 8.24-8.33 (1H, m), 8.51 (1H, d, J=2.7 Hz), 8.69-8.78 (1H, m).
ESI-MS (m/e): 398 [M+H]+

Reference Example 1

Production of 4-(methylsulfonyl)phenol

Methyl iodide (18.5 ml) and potassium carbonate (28.7 g) were added to an acetone (250 ml) solution of 4-hydroxythiophenol (25 g) in a water bath, and stirred at room temperature for 5 hours. The salt was removed through filtration, the solvent was evaporated away under reduced pressure, diethyl ether was added to it, and extracted with aqueous 2 N sodium hydroxide solution. The resulting aqueous layer was made acidic with aqueous 6 N hydrochloric acid solution, extracted with diethyl ether, and the organic layer was washed with aqueous saturated sodium chloride solution. After this was dried, the solvent was evaporated away under reduced pressure to obtain 4-(methylsulfanyl)phenol as a pale yellow solid.
Aqueous 30% hydrogen peroxide (67 ml) was gradually and dropwise added to an acetic acid (130 ml) solution of 4-(methylsulfanyl)phenol (27.3 g) in a water bath. After the addition, this was gradually heated up to 100° C., and stirred for 1 hour. The reaction liquid was restored to room temperature, and neutralized with aqueous saturated sodium bicarbonate. This was extracted with ethyl acetate, washed with aqueous saturated sodium bicarbonate and saturated saline water. After this was dried, the solvent was evaporated away to obtain the entitled compound as a pale yellow solid.

Reference Example 2

Production of 4-(ethylsulfonyl)phenol

Using ethyl iodide, the entitled compound was obtained in the same manner as in Reference Example 1, or according to the method or according to a combination thereof with an ordinary method.

Reference Example 3

Production of 6-(methylsulfonyl)-3-pyridinol

Bis(pinacolate)diboron (6.6 g), potassium acetate (5.9 g) and (1,1'-bis(diphenylphosphino)ferrocene)dichloropalladium(II)/dichloromethane complex (980 mg) were added to a dimethyl sulfoxide (80 ml) solution of 3-bromo-6-(methylsulfonyl)pyridine (4.72 g), and the reaction liquid was stirred at 80° C. for 2 hours. Water and ethyl acetate were added to the reaction liquid, and the insoluble matter was removed through filtration through Celite, and then the organic layer was separated. The organic layer was washed with water and saturated saline water, and dried with anhydrous magnesium sulfate, and the solvent was evaporated away under reduced pressure.
To a tetrahydrofuran (200 ml) solution of the resulting residue, added were aqueous 5 N sodium hydroxide solution (60 ml) and aqueous 30% hydrogen peroxide (30 ml) at 0° C., and the reaction liquid was stirred overnight at room temperature. The reaction liquid was diluted with diethyl ether, and washed with water. The aqueous layer was made acidic with 5 N hydrochloric acid, and extracted with ethyl acetate. The organic layer was dried with anhydrous magnesium sulfate, and the solvent was evaporated away under reduced pressure. The resulting residue was washed with a mixed solvent of chloroform and hexane to obtain the entitled compound as a brown solid.

Reference Example 4

Production of 6-(ethylsulfonyl)-3-pyridinol

Using 3-chloro-6-(ethylsulfonyl)pyridine, the entitled compound was obtained in the same manner as in Reference Example 3, or according to the method or according to a combination thereof with an ordinary method.

Reference Example 5

Production of 3-chloro-4-(methylsulfonyl)phenol

Thionyl chloride (48.3 ml) was added to methanesulfonic acid (108 ml), and heated under reflux for 1 hour. This was restored to room temperature, and 1,3-dichlorobenzene and trifluorosulfonic acid (2.9 ml) were added to it, and stirred under heat at 120° C. for 4 hours. This was restored to room temperature, and the reaction liquid was poured into water with ice, and extracted with ethyl acetate. The organic layer was washed with water, aqueous saturated sodium bicarbonate, and saturated saline water. After this was dried, the solvent was evaporated away under reduced pressure. This was recrystallized from a mixed solvent of hexane/ethyl acetate to obtain 2,4-dichlorophenylmethyl sulfone.
An aqueous solution (1 ml) of potassium hydroxide (360 mg) was added to a dimethylsulfoxide (3 ml) solution of 2,4-dichlorophenylmethyl sulfone (1 g), and stirred at 100° C. for 4 hours. This was made acidic with aqueous 1 N hydrochloric acid solution, extracted with ethyl acetate, and the organic layer was washed with saturated saline water. After this was dried, the solvent was evaporated away under reduced pressure, and the residue was purified through silica gel column chromatography (developing solvent: hexane/ethyl acetate=9/1 to 2/1) to obtain 3-chloro-4-(methylsulfonyl)phenol.

Reference Example 6

6-(5-methyl-1,2,4-oxadiazol-3-yl)-3-pyridinol (Step 1)

Production of 6-bromo-3-pyridinol

With cooling with ice, isopropylmagnesium chloride (2 M tetrahydrofuran solution, 435 ml) was added to a tetrahydrofuran (800 ml) solution of 2,5-dibromopyridine (200 g), and stirred at room temperature for 1.5 hours. With cooling with ice, a tetrahydrofuran (200 ml) solution of triisopropyl borate (214 ml) was added to it, and stirred overnight at room temperature. With cooling with ice, the reaction liquid was gradually added to an aqueous solution (2.5 L) of sodium hydroxide (160 g). Water (1 L) and hexane (1 L) were added to it, and an aqueous layer was thus extracted out. With cooling with ice, aqueous hydrogen peroxide (30%, 150 ml) was gradually added to the aqueous layer, taking 1 hour, and then stirred overnight at room temperature. With cooling with ice, the reaction liquid was neutralized with concentrated hydrochloric acid, extracted with ethyl acetate, and the organic layer was washed with saturated saline water. After this was dried, the solvent was evaporated away under reduced pressure to obtain the entitled compound.
(Step 2)

Production of 2-bromo-5-(methoxymethoxy)pyridine

Methoxymethyl chloride (73 ml) was added to a tetrahydrofuran (1.3 L) solution of 6-bromo-3-pyridinol (129 g) thus obtained, and sodium hydride (40% liquid paraffin added, 32 g) was added to it in such a manner that the inner temperature could not be above −10° C. Water was added, and extracted with ethyl acetate, and the organic layer was washed with saturated saline water. After dried, the solvent was evaporated away under reduced pressure, and this was purified through silica gel column chromatography (developing solvent: hexane/ethyl acetate=9/1 to 8/1) to obtain the entitled compound as a colorless oily substance.
(Step 3)

Production of
5-(methoxymethoxy)-2-pyridinecarbonitrile

To a dimethylformamide (1100 ml) solution of the obtained oily substance (105 g), added were zinc cyanide (88.9 g) and tetrakis(triphenylphosphine)palladium(0) (29.1 g), and stirred under heat at 105° C. for 1 hour. This was restored to room temperature, and ethyl acetate (1.5 L) and water (1.2 L) were added to it, and extracted with ethyl acetate. The organic layer was washed with saturated saline water, dried, and the solvent was evaporated away under reduced pressure, and this was purified through silica gel column chromatography (developing solvent: hexane/ethyl acetate=8/1 to 7/1 to 2/1) to obtain the entitled compound.
(Step 4)

Production of
6-(5-methyl-1,2,4-oxadiazol-3-yl)-3-pyridinol

With cooling with ice, hydroxylamine (50% aqueous solution, 35.4 ml) was added to an ethanol (400 ml) solution of the obtained product (41 g), and stirred at room temperature for 30 minutes. With cooling with ice, water (1 L) was added to it, and stirred for 1 hour. The resulting crystal was taken out through filtration to obtain a product.

Acetic acid (200 ml) was added to the obtained crystal (39.5 g), and with cooling with ice, acetic anhydride (20.8 ml) was added to it, and stirred at room temperature for 1 hour. This was heated up to 70° C. as such, and stirred overnight. The reaction solvent was evaporated away under reduced pressure, and trifluoroacetic acid (100 ml) was added to the obtained brown solid, and stirred at room temperature for 3 hours. The solvent was evaporated away under reduced pressure, and a mixed solvent of hexane/ethyl acetate=20/1 was added to it, and stirred. The resulting solid was taken out through filtration, and dried to obtain trifluoroacetate of the entitled compound.

Reference Example 7

4-(5-methyl-1,2,4-oxadiazol-3-yl)phenol (Step 1)

Production of 4-(methoxymethoxy)benzonitrile

Using 4-cyanophenol, the entitled compound was obtained in the same manner as in Reference Example 6 (step 2), or according to the method or according to a combination thereof with an ordinary method.
(Step 2)

4-(5-methyl-1,2,4-oxadiazol-3-yl)phenol

Using 4-(methoxymethoxy)benzonitrile, the entitled compound was obtained in the same manner as in Reference Example 6 (step 4), or according to the method or according to a combination thereof with an ordinary method.

Reference Example 8

Production of 6-(methoxymethyl)pyridin-3-ol (Step 1)

Production of 5-benzyloxy-2-methylpyridine

3-Hydroxy-6-methylpyridine (140 g) was dissolved in dimethylformamide (1.4 L), and with cooling with ice, benzyl chloride (178 ml) was added to it, and stirred overnight at room temperature. The reaction liquid was poured into water with ice, extracted with ethyl acetate, and the organic layer was washed with saturated saline water. After dried, the solvent was evaporated away under reduced pressure, and the residue was purified through silica gel column chromatography (developing solvent: hexane/ethyl acetate=40/1 to 2/1) to obtain the entitled compound as an orange oil.
(Step 2)

Production of [5-(benzyloxy)pyridin-2-yl]methanol

With cooling with ice, m-chloroperbenzoic acid (335.8 g) was added to a chloroform (2.8 L) solution of the obtained oil (246.7 g), and stirred for 1 hour. The reaction liquid was washed with aqueous 10% sodium carbonate solution and saturated saline water. After dried, the solvent was evaporated away under reduced pressure, and recrystallized (hexane/ethyl acetate) to obtain a pale yellow crystal.

Acetic anhydride (600 ml) was added to the obtained crystal (266 g), gradually heated, and stirred at 120° C. for 20 minutes. The solvent was evaporated away under reduced pressure, aqueous saturated sodium bicarbonate was added to it, and extracted with ethyl acetate. The organic layer was washed saturated saline water, and dried with anhydrous magnesium sulfate. The solvent was evaporated away under reduced pressure, and the residue was purified through silica gel column chromatography (developing solvent: hexane/ethyl acetate=50/1 to 2/1) to obtain a brown oil.

The obtained oil (259 g) was dissolved in ethanol (2 L) and water (500 ml), and sodium hydroxide (80 g) was added to it, and heated under reflux for 30 minutes. The solvent was evaporated away under reduced pressure, then water (300 ml) was added to it and extracted with ethyl acetate. The organic layer was washed with aqueous saturated ammonium chloride solution and saturated saline water, and dried with anhydrous magnesium sulfate. After dried, the solvent was evaporated away under reduced pressure, and recrystallized (diethyl ether) to obtain the entitled compound as a brown crystal.
(Step 3)

Production of 6-(methoxymethyl)pyridin-3-ol

The obtained brown crystal (169 g) was dissolved in tetrahydrofuran (1.6 L), and with cooling with ice, sodium hydride (40% liquid paraffin added, 37.7 g) was added to it, and stirred at room temperature for 1 hour. With cooling with ice, iodomethane (53.7 ml) was gradually and dropwise added to it, and stirred overnight at room temperature. With cooling with ice, water was added to it, and extracted with ethyl acetate, and the organic layer was washed with saturated saline water. After dried, the solvent was evaporated away under reduced pressure, and the residue was purified through silica gel column chromatography (developing solvent: hexane/ethyl acetate=60/1 to 2/1) to obtain an orange oil.

The obtained oil (91.4 g) was dissolved in ethanol (900 ml), and 10% palladium-carbon (13 g) was added to it, and stirred in a hydrogen atmosphere for 2 hours. After filtered, the solvent was evaporated away under reduced pressure, and recrystallized (ethyl acetate/hexane) to obtain the entitled compound as a pale yellow crystal.

Reference Example 9

5-Hydroxypyridine-2-carbonitrile 4-(Methoxymethoxy)benzonitrile obtained in Reference Example 7 (step 1) was used, as combined with Reference Example 6 (step 4), trifluoroacetate of the entitled compound was obtained.

Reference Example 10

(Step 1)

Production of methyl 2-fluoro-4-nitrobenzoate

Concentrated sulfuric acid (5 ml) was added to a methanol (1300 ml) solution of 2-fluoro-4-nitrobenzoic acid (140 g), and heated under reflux for 48 hours. The solvent was evaporated away under reduced pressure, water was added to it, and the formed solid was taken out through filtration. After dried under reduced pressure, the entitled compound was obtained as a yellow solid.
(Step 2)

Production of methyl 4-amino-2-fluorobenzoate

Methyl 2-fluoro-4-nitrobenzoate (141 mg) was dissolved in methanol (1000 ml) and tetrahydrofuran (400 ml), and Raney nickel (20 g) was added to it, and stirred overnight in a hydrogen atmosphere. The catalyst was removed through filtration, and the solvent was evaporated away under reduced pressure to obtain methyl 4-amino-2-fluorobenzoate.
(Step 3)

Production of methyl 2-fluoro-4-[(2-pyridinylcarbonyl)amino]benzoate 1-(3-dimethylaminopropyl)-3-ethylcarbodiimide hydrochloride was added to a pyridine (500 ml) solution of methyl 4-amino-2-fluorobenzoate (18.9 g) and picolinic acid (16.5 g), and stirred at room temperature for 2 hours. The solvent was evaporated away under reduced pressure, ethyl acetate (600 ml) was added to it, and the organic layer was washed with aqueous 0.25 N hydrochloric acid solution, aqueous 0.25 N sodium hydroxide solution and saturated saline water. After dried, this was concentrated under reduced pressure, and solidified from a mixed solvent of hexane/ethyl acetate, and taken out through filtration. After dried under reduced pressure, the entitled compound was obtained as a white solid.
(Step 4)

Production of methyl 2-fluoro-5-nitro-4-[(2-pyridinylcarbonyl)amino]benzoate

With cooling with ice, fuming nitric acid (110 ml) was gradually added to methyl 2-fluoro-4-[(2-pyridinylcarbonyl)amino]benzoate (27.7 g), and stirred at room temperature for 1.5 hours. With cooling with ice, the reaction liquid was gradually added to an aqueous solution (2000 ml) of sodium carbonate (138 g), and the formed solid was taken out through filtration. After dried under reduced pressure, the entitled compound was obtained as a yellow solid.
(Step 5)

Production of methyl 2-[4-(ethylsulfonyl)phenoxy]-5-nitro-4-[(2-pyridinylcarbonyl)amino]benzoate To a dimethylformamide (110 ml) solution of methyl 2-fluoro-5-nitro-4-[(2-pyridinylcarbonyl)amino]benzoate (6 g) and 4-(ethylsulfonyl)phenol (3.48 g) obtained in Reference Example 2, added was potassium carbonate (3.5 g), and stirred under heat at 80° C. for 30 minutes. The reaction liquid was restored to room temperature, then poured into water (300 ml), and the formed solid was taken out through filtration. After dried under reduced pressure, the entitled compound was obtained as a yellow solid.
(Step 6)

Production of methyl 5-[4-(ethylsulfonyl)phenoxy]-2-(2-pyridinyl)-1H-benzimidazole-6-carboxylate Methyl 2-[4-(ethylsulfonyl)phenoxy]-5-nitro-4-[(2-pyridinylcarbonyl)amino]benzoate (7.46 g) was suspended in dimethylformamide (37 ml) and methanol (37 ml), and tin(II) chloride dihydrate (17.3 g) and concentrated hydrochloric acid (15 ml) were added to it, and stirred under heat at 80° C. for 40 minutes. The reaction liquid was restored to room temperature, and gradually added to an aqueous sodium hydrogencarbonate solution and neutralized. Ethyl acetate was added to it, and stirred at room temperature for 30 minutes, and the formed salt was taken out through filtration. The filtrate was washed with water and saturated saline water. After dried, the solvent was evaporated away to obtain the entitled compound as a yellow solid.
(Step 7)

Production of 6-(4-(ethylsulfonyl)phenoxy)-2-pyridin-2-yl-1H-benzimidazole-5-carboxylic acid Aqueous 1 N sodium hydroxide solution (10 ml) was added to the methyl ester compound (2.3 g) obtained in (step 6), and the reaction liquid was stirred overnight at 50° C. 3 N hydrochloric acid (4 ml) was added to the reaction liquid, and the formed precipitate was taken out through filtration to obtain the entitled compound.

(Step 8)

Production of (6-(4-(ethylsulfonyl)phenoxy)-2-pyridin-2-yl-1H-benzimidazol-5-yl)methanol 1,1'-carbonyldiimidazole (700 mg) was added to a dimethylformamide (5 ml) solution of the carboxylic acid (1.5 g) obtained in (step 7), and the reaction liquid was stirred at room temperature for 15 minutes. The reaction liquid was added to an aqueous solution (5 ml) of sodium borohydride (1.5 g), and stirred at room temperature for 5 minutes. Then, this was diluted with ethyl acetate, washed with water and saturated saline water in that order, and dried with anhydrous sodium sulfate. The solvent was evaporated away under reduced pressure to obtain the entitled compound as an orange solid.

(Step 9)

Production of 6-[4-(ethylsulfonyl)phenoxy]-2-pyridin-2-yl-1H-benzimidazole-5-carbaldehyde Triethylamine (5 ml) and pyridine-sulfur trioxide (750 mg) were added to a dimethyl sulfoxide (10 ml) solution of the alcohol compound (1.0 g) obtained in (step 8), and the reaction liquid was stirred at room temperature for 15 minutes. The reaction liquid was diluted with ethyl acetate, washed with water and saturated saline water in that order, and dried with anhydrous sodium sulfate.

The solvent was evaporated away under reduced pressure to obtain the entitled compound as an orange solid.

Using the phenol analogues obtained in Reference Example 1 to Reference Example 9, the following groups were obtained in the same manner as in Reference Example 10, or according to the method or according to a combination thereof with an ordinary method.

Reference Example 11 methyl 6-(4-methylsulfonyl)phenoxy)-2-pyridin-2-yl-1H-benzimidazole-5-carboxylate,
6-(4-methylsulfonyl)phenoxy)-2-pyridin-2-yl-1H-benzimidazole-5-carboxylic acid,
(6-(4-(methylsulfonyl)phenoxy)-2-pyridin-2-yl-1H-benzimidazol-5-yl)methanol,
6-(4-(methylsulfonyl)phenoxy)-2-pyridin-2-yl-1H-benzimidazole-5-carbaldehyde.

Reference Example 12 methyl 6-((6-(ethylsulfonyl)pyridin-3-yl)oxy)-2-pyridin-2-yl-1H-1-benzimidazole-5-carboxylate,
6-((6-(ethylsulfonyl)pyridin-3-yl)oxy)-2-pyridin-2-yl-1H-benzimidazole-5-carboxylic acid,
(6-((6-(ethylsulfonyl)pyridin-3-yl)oxy)-2-pyridin-2-yl-1H-benzimidazole-5-yl)methanol,
6-((6-(ethylsulfonyl)pyridin-3-yl)oxy)-2-pyridin-2-yl-1H-benzimidazole-5-carbaldehyde.

Reference Example 13 methyl 6-((6-(methylsulfonyl)pyridin-3-yl)oxy)-2-pyridin-2-yl-1H-benzimidazole-5-carboxylate,
6-((6-(methylsulfonyl)pyridin-3-yl)oxy)-2-pyridin-2-yl-1H-benzimidazole-5-carboxylic acid,
(6-((6-(methylsulfonyl)pyridin-3-yl)oxy)-2-pyridin-2-yl-1H-benzimidazole-5-yl)methanol,
6-((6-(methylsulfonyl)pyridin-3-yl)oxy)-2-pyridin-2-yl-1H-benzimidazole-5-carbaldehyde.

Reference Example 14 methyl 6-(6-(5-methyl-(1,2,4)oxadiazol-3-yl)-pyridin-3-yloxy)-2-pyridin-2-yl-1H-benzimidazole-5-carboxylate,
6-(6-(5-methyl-(1,2,4)oxadiazol-3-yl)-pyridin-3-yloxy)-2-pyridin-2-yl-1H-benzimidazole-5-carboxylic acid,
(6-(6-(5-methyl-(1,2,4)oxadiazol-3-yl)-pyridin-3-yloxy)-2-pyridin-2-yl-1H-benzimidazole-5-yl)methanol,
6-(6-(5-methyl-(1,2,4)oxadiazol-3-yl)-pyridin-3-yloxy)-2-pyridin-2-yl-1H-benzimidazole-5-carbaldehyde.

Reference Example 15 methyl 6-((6-(methoxymethyl)pyridin-3-yl)oxy)-2-pyridin-2-yl-1H-benzimidazole-5-carboxylate,
6-((6-(methoxymethyl)pyridin-3-yl)oxy)-2-pyridin-2-yl-1H-benzimidazole-5-carboxylic acid,
(6-((6-(methoxymethyl)pyridin-3-yl)oxy)-2-pyridin-2-yl-1H-benzimidazole-5-yl)methanol,
6-((6-(methoxymethyl)pyridin-3-yl)oxy)-2-pyridin-2-yl-1H-benzimidazole-5-carbaldehyde.

Reference Example 16 methyl 6-(4-(ethylsulfonyl)phenoxy)-2-pyrazin-2-yl-1H-benzimidazole-5-carboxylate,
6-(4-(ethylsulfonyl)phenoxy)-2-pyrazin-2-yl-1H-benzimidazole-5-carboxylic acid,
(6-(4-(ethylsulfonyl)phenoxy)-2-pyrazin-2-yl-1H-benzimidazole-5-yl)methanol,
6-(4-(ethylsulfonyl)phenoxy)-2-pyrazin-2-yl-1H-benzimidazole-5-carbaldehyde.

Reference Example 17 methyl 6-((6-(ethylsulfonyl)pyridin-3-yl)oxy)-2-pyrazin-2-yl-1H-benzimidazole-5-carboxylate,
6-((6-(ethylsulfonyl)pyridin-3-yl)oxy)-2-pyrazin-2-yl-1H-benzimidazole-5-carboxylic acid,
(6-((6-(ethylsulfonyl)pyridin-3-yl)oxy)-2-pyrazin-2-yl-1H-benzimidazole-5-yl)methanol,
6-((6-(ethylsulfonyl)pyridin-3-yl)oxy)-2-pyrazin-2-yl-1H-benzimidazole-5-carbaldehyde.

Reference Example 18 methyl 6-((6-cyanopyridin-3-yl)oxy)-2-pyridin-2-yl-1H-benzimidazole-5-carboxylate,
6-((6-cyanopyridin-3-$)_4$)oxy)-2-pyrazin-2-yl-1H-benzimidazole-5-carboxylic acid,
(6-((6-cyanopyridin-3-yl)oxy)-2-pyrazin-2-yl-1H-benzimidazole-5-yl)methanol,
6-((6-cyanopyridin-3-yl)oxy)-2-pyrazin-2-yl-1H-benzimidazole-5-carbaldehyde.

Reference Example 19

Production of methyl 5-[4-(ethylsulfonyl)phenoxy]-2-(2-pyridyl)-1-{[2-(trimethylsilyl)ethoxy]methyl}-1H-benzimidazole-6-carboxylate and methyl 6-[4-(ethylsulfonyl)phenoxy]-2-(2-pyridyl)-1-([2-(trimethylsilyl)ethoxy]methyl)-1H-benzimidazole-5-carboxylate With cooling with ice, 2-(trimethylsilyl)ethoxymethyl chloride (4 ml) and sodium hydride (40% liquid paraffin added, 0.92 g) were added to a dimethylformamide (70 ml) solution of methyl 5-[4-(ethylsulfonyl)phenoxy]-2-(2-pyridinyl)-1H-benzimidazole-6-carboxylate (6.9 g) obtained in Reference Example 10 (step 6), and stirred at room temperature for 30 minutes. With cooling with ice, aqueous saturated ammonium chloride solution was added to it, and extracted with ethyl acetate, and the organic layer was washed with water and saturated saline water. After dried, the solvent was evaporated away under reduced pressure, and the residue was purified through silica gel column chromatography (developing solvent: hexane/ethyl acetate=9/1 to 3/2) to obtain the entitled compound as a yellow oil.

INDUSTRIAL APPLICABILITY

Hetero ring-substituted benzimidazole derivatives of formula (I) and their pharmaceutically-acceptable salt of the invention have an excellent effect of glucokinase activation, and are useful in the field of medicines for remedy and/or prevention of diabetes, complications of diabetes or obesity.

The invention claimed is:
1. A compound of a formula (I):

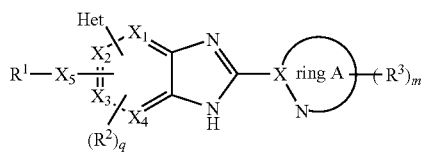

or its pharmaceutically-acceptable salt thereof, wherein:
$X_1$ to $X_4$ each represent a carbon atom;
ring A is a 6-membered heteroaryl consisting of one nitrogen atom and five carbon atoms as represented by a formula (II):

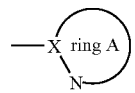

X represents a carbon atom;
Het represents a 5 or 6 membered aliphatic, saturated heterocyclic ring having 1-2 oxygen or sulfur atoms, or a 5-6 membered aliphatic, saturated heterocyclic ring having 1-2 oxygen or sulfur atoms, and in addition, 1-2 heteroatoms selected from the group consisting of O, S and N;
said 5- or 6-membered aliphatic saturated heterocyclic ring may be mono- to tri-substituted with the same or different —$C_{1-6}$ alkyl optionally substituted with halogen or lower alkoxy, —O—$C_{1-6}$ alkyl optionally substituted with halogen or lower alkoxy, oxo or thioxo;
$X_5$ represents —O—, —S—, —S(O)—, —S(O)$_2$—, —S(O)$_2$N—, —C(O)— or —NS(O)$_2$—;
$R^1$ represents aryl, —$C_{1-6}$ alkyl or —$C_{3-7}$ cycloalkyl, or represents a 5- or 6-membered heteroaryl having from 1 to 3 hetero atoms selected from the group consisting of a nitrogen atom, a sulfur atom and an oxygen atom in the ring, or a condensed group of the heteroaryl with phenyl or pyridyl;
said $R^1$ may be substituted with from 1 to 4, the same or different $R^4$ groups;

$R^2$ each independently represents formyl, —OH, —$C_{1-6}$ alkyl, —$CH_{3-a}F_a$, —$OCH_{3-a}F_a$, wherein a is an integer from 1 to 3, amino, cyano, halogen or —(CH$_2$)$_{1-6}$—OH;
$R^3$ each independently represents —$C_{1-6}$alkyl, —(CH$_2$)$_{1-6}$—OH, —C(O)—OC$_{1-6}$ alkyl, —(CH$_2$)$_{1-6}$—$C_{1-6}$ alkyl, —(CH$_2$)$_{1-6}$—NH$_2$, cyano, —C(O)—$C_{1-6}$ alkyl, halogen, —$C_{2-6}$ alkenyl, —OC$_{1-6}$ alkyl, —COOH or —OH;
each $R^4$ independently represents —$C_{1-6}$ alkyl optionally substituted with from 1 to 3, the same or different substituents of hydroxy, halogen, —OC(O)—$C_{1-6}$ alkyl or —OC$_{1-6}$ alkyl, wherein —OC(O)—$C_{1-6}$ alkyl may be substituted with from 1 to 3 halogens,
—$C_{3-7}$ cycloalkyl,
—$C_{2-6}$ alkenyl,
—C(O)—N(R$^{51}$)R$^{52}$,
—S(O)$_2$—N(R$^{51}$)R$^{52}$,
—O—$C_{1-6}$ alkyl optionally substituted with halogen or N(R$^{51}$)R$^{52}$,
—S(O)$_{0-2}$—$C_{1-6}$ alkyl,
—C(O)—$C_{1-6}$ alkyl optionally substituted with halogen, amino, CN, hydroxy, —O—$C_{1-6}$ alkyl, —$CH_{3-a}F_a$, —OC(O)—$C_{1-6}$ alkyl, —N(C$_{1-6}$ alkyl)C(O)O—$C_{1-6}$ alkyl, —NH—C(O)O—$C_{1-6}$ alkyl, phenyl, —N(R$^{51}$)R$^{52}$, —NH—C(O)—$C_{1-6}$ alkyl, —N(C$_{1-6}$ alkyl)-C(O)—$C_{1-6}$ alkyl or —NH—S(O)$_{0-2}$—$C_{1-6}$ alkyl,
—C(S)—$C_{3-7}$ cycloalkyl,
—C(S)—$C_{1-6}$ alkyl,
—C(O)—O—$C_{1-6}$ alkyl,
—(CH$_2$)$_{0-4}$—N(R$^{53}$)—C(O)—R$^{54}$,
—N(R$^{53}$)—C(O)—O—R$^{54}$,
—C(O)-aryl optionally substituted with halogen,
—C(O)-aromatic hetero ring,
—C(O)-aliphatic hetero ring,
hetero ring optionally substituted with —$C_{1-6}$ alkyl, said —$C_{1-6}$ alkyl may be substituted with halogen or —O—$C_{1-6}$ alkyl,
phenyl, said phenyl may be substituted with halogen, —$C_{1-6}$ alkyl, —O—$C_{1-6}$ alkyl,
halogen,
CN,
formyl,
COOH,
amino,
oxo,
hydroxy,
hydroxyamidino or
nitro;
$R^{51}$ and $R^{52}$ each independently represent a hydrogen atom or —$C_{1-6}$ alkyl, or $R^{51}$ and $R^{52}$, taken together with the nitrogen atom, form a 4- to 7-membered hetero ring;
$R^{53}$ represents a hydrogen atom or —$C_{1-6}$ alkyl;
$R^{54}$ represents —$C_{1-6}$ alkyl, or
the alkyls of $R^{53}$ and $R^{54}$, taken together with —N—C(O)—, form a 4- to 7-membered, nitrogen-containing aliphatic hetero ring, or
the alkyls of $R^{53}$ and $R^{54}$, taken together with —N—C(O)—O—, form a 4- to 7-membered, nitrogen-containing aliphatic hetero ring, said aliphatic hetero ring may be substituted with oxo, or said aliphatic hetero ring may have one or two double bonds in the ring;
m indicates an integer of from 0 to 2;
q indicates an integer of from 0 to 2.
2. The compound of claim 1 or a pharmaceutically acceptable salt thereof, wherein: $R^1$ is aryl, or 5- or 6-membered heteroaryl having from 1 to 3 hetero atoms selected from the group consisting of a nitrogen atom, a sulfur atom and an oxygen atom in the ring, or a condensed group of the heteroaryl with phenyl or pyridyl, said $R^1$ may be substituted with from 1 to 4, the same or different $R^4$'s.

3. The compound or its pharmaceutically-acceptable salt as claimed in claim 1, wherein $X_5$ is —O—, —S—, —S(O)— or —S(O)$_2$—.

4. The compound of claim 1 or a pharmaceutically acceptable salt thereof, wherein the formula (I) is a formula (I-1):

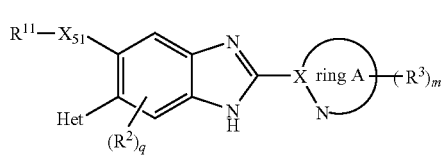

wherein:
$R^{11}$ represents phenyl, or 5- or 6-membered nitrogen-containing heteroaryl having from 1 to 4 hetero atoms selected from the group consisting of a nitrogen atom, a sulfur atom and an oxygen atom in the ring, said $R^{11}$ may be substituted with from 1 to 3, the same or different $R^4$ groups;
$X_{51}$ represents —O—, —S—, —S(O)— or —S(O)$_2$—; and the other symbols have the same meanings as above.

5. The compound of claim 1 or a pharmaceutically acceptable salt thereof, wherein the compound of formula (I) is selected from the group consisting of:
5-(1,3-dioxolan-2-yl)-6-(4-(ethylsulfonyl)phenoxy)-2-pyridin-2-yl-1H-benzimidazole,
5-(1,3-dioxolan-2-yl)-6-((6-(ethylsulfonyl)pyridin-3-yl)oxy)-2-pyridin-2-yl-1H-benzimidazole,
5-(4-(hydroxymethyl)-1,3-dioxolan-2-yl)-6-(4-(ethylsulfonyl)phenoxy)-2-pyridin-2-yl-1H-benzimidazole,
5-(1,3-dioxan-2-yl)-6-(4-(ethylsulfonyl)phenoxy)-2-pyridin-2-yl-1H-benzimidazole,
5-(3-acetyl-1,3-oxazolidin-2-yl)-6-(4-(ethylsulfonyl)phenoxy)-2-pyridin-2-yl-1H-benzimidazole,
5-(6-(4-(ethylsulfonyl)phenoxy)-2-pyridin-2-yl-1H-benzimidazol-5-yl)tetrahydrofuran-2-ol,
5-(tetrahydrofuran-2-yl)-6-(4-(ethylsulfonyl)phenoxy)-2-pyridin-2-yl-1H-benzimidazole,
5-(tetrahydrofuran-2-yl)-6-((6-(ethylsulfonyl)pyridin-3-yl)oxy)-2-pyridin-2-yl-1H-benzimidazole,
5-(6-((6-(ethylsulfonyl)pyridin-3-yl)oxy)-2-pyridin-2-yl-1H-benzimidazol-5-yl)tetrahydrofuran-2-ol,
5-(tetrahydrofuran-2-yl)-6-(4-(methylsulfonyl)phenoxy)-2-pyridin-2-yl-1H-benzimidazole,
5-(tetrahydrofuran-2-yl)-6-(6-(5-methyl-(1,2,4)oxadiazol-3-yl)-pyridin-3-yloxy)-2-pyridin-2-yl-1H-benzimidazole,
5-(tetrahydrofuran-2-yl)-6-((6-(methylsulfonyl)pyridin-3-yl)oxy)-2-pyridin-2-yl-1H-benzimidazole,
5-(4-methyltetrahydrofuran-2-yl)-6-(4-(methylsulfonyl)phenoxy)-2-pyridin-2-yl-1H-benzimidazole,
5-(6-(4-(methylsulfonyl)phenoxy)-2-pyridin-2-yl-1H-benzimidazol-5-yl)tetrahydrofuran-2-ol,
5-(6-(4-(ethylsulfonyl)phenoxy)-2-pyridin-2-yl-1H-benzimidazol-5-yl)dihydrofuran-2(3H)-one,
5-(6-((6-methylsulfonyl)pyridin-3-yl)oxy)-2-pyridin-2-yl-1H-benzimidazol-5-yl)dihydrofuran-2(3H)-one,
5-(6-(5-methyl-(1,2,4)oxadiazol-3-yl)-pyridin-3-yloxy)-2-pyridin-2-yl-1H-benzimidazol-5-yl)dihydrofuran-2(3H)-one,
5-(6-((6-(ethylsulfonyl)pyridin-3-yl)oxy)-2-pyridin-2-yl-1H-benzimidazol-5-yl)dihydrofuran-2(3H)-one,
5-(tetrahydro-2-thienyl)-6-(4-(ethylsulfonyl)phenoxy)-2-pyridin-2-yl-1H-benzimidazole, 5-(1,2-dithian-3-yl)-6-(4-(ethylsulfonyl)phenoxy)-2-pyridin-2-yl-1H-benzimidazole,
5-(1-oxidotetrahydro-2-thienyl)-6-(4-(ethylsulfonyl)phenoxy)-2-pyridin-2-yl-1H-benzimidazole,
5-(1,1-dioxidotetrahydro-2-thienyl)-6-(4-(ethylsulfonyl)phenoxy)-2-pyridin-2-yl-1H-benzimidazole,
5-(6-(4-(ethylsulfonyl)phenoxy)-2-pyridin-2-yl-1H-benzimidazol-5-yl)-3-methyl-1,3-oxazolidine-2,4-dione,
5-(6-((6-(ethylsulfonyl)pyridin-3-yl)oxy)-2-pyridin-2-yl-1H-benzimidazol-5-yl)-3-methyl-1,3-oxazolidine-2,4-dione,
5-(6-(4-(ethylsulfonyl)phenoxy)-2-pyridin-2-yl-1H-benzimidazol-5-yl)-1,3-oxazolidine-2,4-dione,
5-(6-(4-(ethylsulfonyl)phenoxy)-2-pyridin-2-yl-1H-benzimidazol-5-yl)-2,2-dimethyl-1,3-dioxolan-4-one,
4-(6-(4-(ethylsulfonyl)phenoxy)-2-pyridin-2-yl-1H-benzimidazol-5-yl)-1,3-dioxolan-2-one,
3-(6-(4-(ethylsulfonyl)phenoxy)-2-pyridin-2-yl-1H-benzimidazol-5-yl)dihydrofuran-2(3H)-one, 3-(6-((6-(ethylsulfonyl)pyridin-3-yl)oxy)-2-pyridin-2-yl-1H-benzimidazol-5-yl)dihydrofuran-2(3H)-one,
5-(tetrahydrofuran-3-yl)-6-((6-(ethylsulfonyl)pyridin-3-yl)oxy)-2-pyridin-2-yl-1H-benzimidazol, and
5-(6-((6-cyanopyridin-3-yl)oxy)-2-pyridin-2-yl-1H-benzimidazol-5-yl)dihydrofuran-2(3H)-one,
and the pharmaceutically acceptable salts thereof.

6. A pharmaceutical composition comprising the following (1) to (3):
(1) a compound of claim 1;
(2) one or more compounds selected from the following groups (a) to (h):
(a) any other glucokinase activator,
(b) a bis-guanide,
(c) a PPAR agonist,
(d) an insulin,
(e) a somatostatin,
(f) an α-glucosidase inhibitor,
(g) an insulin secretion promoter, and
(h) a DPP-IV (dipeptidyl peptidase IV) inhibitor; and
(3) a pharmaceutically-acceptable carrier.

7. A method of treating diabetes in a mammalian patient in need of such treatment comprising administering to the patient a compound in accordance with claim 1 in an amount that is effective to treat diabetes.

8. A method of treating obesity in a mammalian patient in need of such treatment comprising administering to the patient a compound in accordance with claim 1 in an amount that is effective to treat obesity.

9. A pharmaceutical composition comprised of a compound in accordance with claim 1 in combination with a pharmaceutically acceptable carrier.

* * * * *